United States Patent [19]

Rosentreter et al.

[11] Patent Number: 5,221,760
[45] Date of Patent: Jun. 22, 1993

[54] ALKENOIC ACID DERIVATIVES

[75] Inventors: Ulrich Rosentreter, Wuppertal, Fed. Rep. of Germany; Harold C. Kluender, West Haven, Conn.; Trevor S. Abram, Marlow Bucks, United Kingdom; Peter Norman, Slough, United Kingdom; Steven R. Tudhope, Windsor, United Kingdom

[73] Assignee: Bayer Aktiengesellschaft, Leverkusen, Fed. Rep. of Germany

[21] Appl. No.: 891,629

[22] Filed: Jun. 1, 1992

Related U.S. Application Data

[62] Division of Ser. No. 618,184, Nov. 26, 1990, Pat. No. 5,159,097, which is a division of Ser. No. 349,371, May 9, 1989, Pat. No. 5,041,638.

[30] Foreign Application Priority Data

May 13, 1988 [GB] United Kingdom .................. 8811423

[51] Int. Cl.$^5$ ............................................ C07C 303/00
[52] U.S. Cl. ...................................................... 558/58
[58] Field of Search ............................................ 558/58

[56] References Cited

FOREIGN PATENT DOCUMENTS 0084667 8/1983 European Pat. Off. .
2184121 6/1987 United Kingdom .

OTHER PUBLICATIONS

E. J. Corey et al., J. Am. Chem. Soc. 87, 1353 (1965).
J. L. van der Barr, F. Bickelhupt, Tetrahedron Letters 30, 2447-2553 (1974).
I. Ernst, A. J. Main, R. Menasse, Tetrahedron Letters 23, 167-170 (1982).
J. Hora, Rec. Trav. Chim. Pays-Bas 98, 45-49 (1976).
R. H. Wollenberg, Tetrahedron letters 8, 717-720.
E. J. Corey et al, Chem. Ber. 111, 1337, 1363 (1978).
D. Enders et al, Org. Synth. 65, 183 (1987).

*Primary Examiner*—Paul J. Killos
*Attorney, Agent, or Firm*—Sprung Horn Kramer & Woods

[57] ABSTRACT

An alkenoic acid derivative of the formula

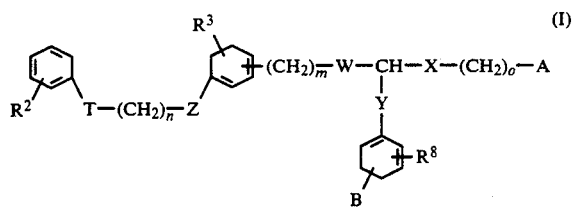

in which
X and Y are identical or different and represent sulfur, sulfoxide, sulfone, an alkylene chain, —SCH$_2$—, or oxygen or a direct bond,
W represents —CH=CH— or —CH$_2$—CH$_2$—,
o represents a number 1 to 5,
A and B are identical or different and represent carboxyl, carboxymethylene, tetrazolyl or tetrazolylmethylene, or —CO$_2$R$^9$ or —CH$_2$CO$_2$R$^9$ or —CONR$^{10}$R$^{11}$ or nitrile
n represents a number 1 to 10,
m represents a number 0 to 7,
T and Z are identical or different and represent oxygen or a direct bond and
R$^2$, R$^3$, R$^8$ are identical or different and represent hydrogen, alkyl, alkoxy, halogen, trifluoromethyl, trifluoromethoxy, cyano or nitro and
R$^9$ is lower alkyl and R$^{10}$ and R$^{11}$ are hydrogen, lower alkyl, alkylsulfonyl or arylsulfonyl or together are an alkylene chain to form a ring and pharmaceutically acceptable salts thereof. Such alkenoic acid derivatives are useful as leucotriene disease antagonists.

8 Claims, No Drawings

ALKENOIC ACID DERIVATIVES

This is a division of application Ser. No. 07/618,184, filed Nov. 26, 1990, now U.S. Pat. No. 5,159,097, which is a division of Ser. No. 349,371 filed May 9, 1989 now U.S. Pat. No. 5,041,638.

BACKGROUND OF THE INVENTION

1. Field of the Invention

The invention relates to alkenoic acid derivatives, processes for their preparation and their use in medicaments.

2. Background Information

The GB 2 184 121 describes phenethyl sulphides with leukotriene antagonistic properties. The more active compounds of the GB 2 184 121 are insufficiently stable for pharmaceutical use.

SUMMARY OF THE INVENTION

New alkenoic acid derivatives of the general formula (I)

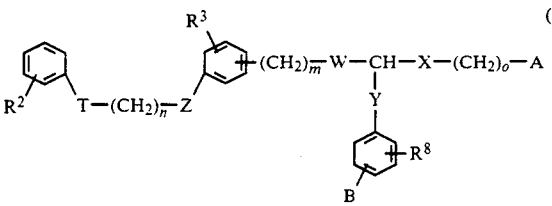

in which
- X and Y are identical or different and represent sulfur, sulfoxide, sulfone, an alkylene chain, a direct bond, $-SCH_2-$ or oxygen
- W represents $-CH=CH-$ or $-CH_2-CH_2-$
- o represents a number 1 to 5
- A and B are identical or different and represent carboxyl, carboxymethylene, tetrazolyl or tetrazolylmethylene, or $-CO_2R^9$ or $-CH_2CO_2X^9$ or $-CONR^{10}R^{11}$ or nitrile
  wherein $R^9$ is lower alkyl and
  $R^{10}$ and $R^{11}$ are hydrogen, lower alkyl, alkylsulfonyl or arylsulfonyl or together are an alkylene chain to form a ring,
- n represents a number 1 to 10,
- m represents a number 0 to 7,
- T and Z are identical or different and represent oxygen or a direct bond and
- $R^2$, $R^3$, $R^8$ are identical or different and represent hydrogen, alkyl, alkoxy, halogen, trifluoromethyl, trifluoromethoxy, cyano or nitro and their salts have been found.

Surprisingly the substances according to the invention are potent leukotriene antagonists and can be used for the therapeutic treatment of humans and animals.

DETAILED DESCRIPTION OF THE INVENTION

The compounds of the formula (I) according to the invention can also be in the form of their salts. In general, the salts which may be mentioned in this context are physiological ones with organic or inorganic bases. The intermediate esters or mixed ester acids or salts thereof can also be used as active compounds in medicaments.

Physiologically acceptable salts are preferred within the scope of the present invention. Physiologically acceptable salts of the alkenoic acid derivatives can be metal or ammonium salts of the substances according to the invention which have free carboxyl groups. Examples of those which are particularly preferred are sodium, potassium, magnesium or calcium salts, as well as ammonium salts which are derived from ammonia or organic amines such as, for example, ethylamine, di- or triethylamine, di- or triethanolamine, dicyclohexylamine, dimethylaminoethanol, arginine or ethylenediamine.

Double bonds can be either cis- or trans-configurated. The carbon between X and Y can be either R- or S-configurated.

In general, alkyl represents straight-chain or a branched hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

In general, cycloalkyl represents a cyclic hydrocarbon radical having 5 to 8 carbon atoms. The cyclopentane and the cyclohexane ring are preferred. Examples which may be mentioned are cyclopentyl, cyclohexyl, cycloheptyl and cyclooctyl.

Alkoxy generally represents a straight-chain or branched hydrocarbon radical which has 1 to 12 carbon atoms and is bonded via an oxygen atom. Lower alkoxy having 1 to 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

In general, aryl represents an aromatic radical having 6 to 12 carbon atoms. Preferred aryl radicals are phenyl, naphthyl and biphenyl.

Halogen generally represents fluorine, chlorine, bromine or iodine, preferably fluorine, chlorine or bromine, Halogen particularly preferably represents fluorine or chlorine.

Sulfoxide may be represented by the formula $>S=O$.

Sulfone may be represented by the formula

Preferred compounds of the general formula (I) are those, in which
- X and Y are identical or different and represent sulfur, sulfoxide, sulfone, a methylene group, $-SCH_2-$, oxygen, an ethylene group or a direct bond,
- W represents $-CH=CH-$ or $-CH_2CH_2-$
- o represents a number 1 to 4
- n represents a number 2 to 7,
- m represents a number 0 to 3,
- T and Z are identical or different and represent oxygen or a direct bond and
- $R^2$, $R^3$, $R^8$ are identical or different and represent hydrogen, lower alkyl, lower alkoxy, fluorine, chlorine or trifluoromethyl, A and B are identical or different and represent carboxyl, carboxylmethylene, tetrazolyl or tetrazolymethylene or —CO$_2$R$^9$ or —CH$_2$CO$_2$R$^9$ or —CONR$^{10}$R$^{11}$ or nitrile
wherein R$^9$ is lower alkyl and
R$^{10}$ and R$^{11}$ are hydrogen, lower alkyl, alkylsulfonyl or arylsulfonyl,
and their salts.

Particularly preferred compounds of the general formula (I) are those in which
X represents sulfur or a methylene group,
Y represents sulfur, a methylene group, SCH$_2$ or a direct bond,
W represents —CH=CH—,
R$^8$ and R$^3$ represent H,
R$^2$ represents H or fluorine
o represents a number 1, 2, 3 or 4
n represents a number 2, 3, 4, 5 or 6,
m represents a number 0, 1, 2 or 3
T represents oxygen or a direct bond
Z represents oxygen or a direct bond
A represents carboxyl or ester thereof
B represents para carboxyl or ester thereof
and their salts.

Examples which may be mentioned are the following alkenoic acid derivatives:

6-(4-Carboxybenzyl)-9-[3-(3-phenoxypropoxy)phenyl]-7(Z)-nonenoic acid
6-(4-Carboxybenzyl)-10-[4-(3-phenoxypropoxy)-phenyl]-7(Z)-decenoic acid
6-(4-Carboxybenzyl)-9-[4-(4-phenoxybutoxy)phenyl]-7(Z)-nonenoic acid
6-(4-Carboxybutoxy)-9-[4-(4-phenoxybutoxy)phenyl]-5-thia-7(Z)-nonenoic acid
6-(4-Carboxybenzyl)-10-[4-(3-phenoxypropoxy)-phenyl]-5-thia-7(Z)-decenoic acid
6-(4-Carboxybenzyl)-9-[3-(3-phenoxypropoxy)phenyl]-5-thia-7(Z)-nonenoic acid
6-(4-Carboxybenzyl)-9-[2-(3-phenoxypropoxy)phenyl]-5-thia-7(Z)-nonenoic acid
6-(4-Carboxybenzyl)-9-[4-(3-phenoxypropoxy)phenyl]-5-thia-7(Z)-nonenoic acid
6-(4-Carboxybenzyl)-9-[2-(3-phenoxypropoxy)phenyl]-7-(Z)-nonenoic acid
6-(4-Carboxybenzyl)-9-[4-(3-phenoxypropoxy)phenyl]-7(Z)-nonenoic acid
6-(4-Carboxybenzyl)-8-[4-(4-phenoxybutoxy)phenyl]-7(E)-octenoic acid
6-(4-Carboxybenzyl)-8-[4-(4-phenoxybutoxy)phenyl]-7(Z)-octenoic acid
6-(4-Carboxybenzyl)-8-[3-(4-phenoxybutoxy)phenyl]-7(Z)-octenoic acid
6-(4-Carboxybenzyl)-8-[3-(4-phenoxybutoxy)phenyl]-7(E)-octenoic acid
6-(4-Carboxybenzyl)-8-[4-(4-phenoxybutoxy)phenyl]-5-thia-7(E)-octenoic acid
6-(4-Carboxybenzyl)-8-[4-(4-phenoxybutoxy)phenyl]-5-thia-7(Z)-octenoic acid
6-(4-Carboxybenzyl)-8-[4-(4-phenoxybutoxy)phenyl]-5-thia-7(Z)-octenoic acid
6-(4-Carboxybenzyl)-8-[3-(4-phenoxybutoxy)phenyl]-5-thia-7(Z)-octenoic acid
6-(4-Carboxybenzyl)-8-[3-(4-phenoxybutoxy)phenyl]-5-thia-7(E)-octenoic acid
6-(4-Carboxybenzyl)-8-[2-(4-phenoxybutoxy)phenyl]-5-thia-7(E)-octenoic acid
6-(4-Carboxybenzyl)-8-[2-(4-phenoxybutoxy)phenyl]-7(E)-octenoic acid
6-(4-Carboxyphenyl)-9-[4-(3-phenoxypropoxy)phenyl]-7(Z)-nonenoic acid
6-(4-Carboxybenzyl)-8-[3-(5-phenoxypentyl)phenyl]-7(E)-octenoic acid
6-(4-Carboxybenzyl)-8-[3-(5-phenoxypentyl)phenyl]-7(Z)-octenoic acid
6-(4-Carboxybenzyl)-8-[4-(5-phenoxypentyl)phenyl]-7(E)-octenoic acid
6-(4-carboxybenzyl)-9-(3-[5-phenylpentyl]-phenyl)-7(Z)-nonenoic acid
6-4-carboxybenzyl)-9-(3-[4-phenoxybutyl]-phenyl)-7(Z)-nonenoic acid
6-(4-carboxybenzyl)-9-3-[3-(4-fluorophenoxy)-propoxy]benzyl-7(Z)-nonenoic acid Furthermore a process for the preparation of the alkenoic acid derivatives, of the formula (I)

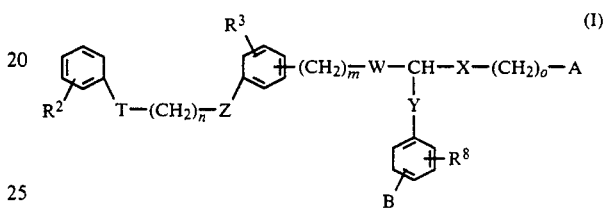

in which
R$^2$, T, Z, R$^3$, W, X, A, B, R$^8$, n, m, o and Y have the above mentioned meanings
has been found, which is characterized in that aldehydes of the general formula (II)

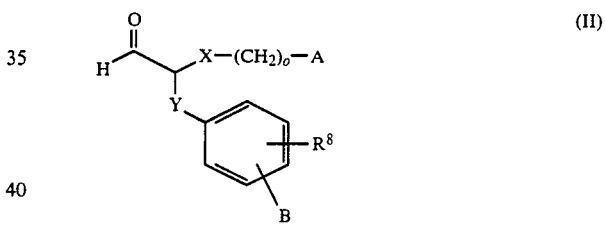

in which
X, Y, o and R$^8$ have the above mentioned meanings and
A and B are identical or different and represent CO$_2$R$^9$ or CH$_2$CO$_2$R$^9$ or CONR$^{10}$R$^{11}$ or nitrile
wherein R$^9$ represents lower alkyl and R$^{10}$ and R$^{11}$ represent lower alkyl, a methylene chain or H,
are reacted with phosphorus compounds of the general formula (III)

R$^1$—CH$_2$—U (III)

in which
R$^1$ is

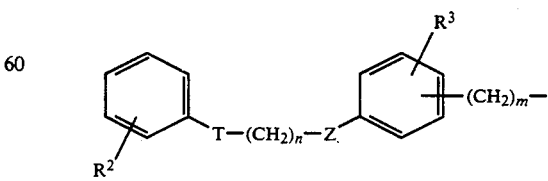

in which
R$^2$, T, n, Z, R$^3$ and m have the above mentioned meanings and

U represents a group of the formula

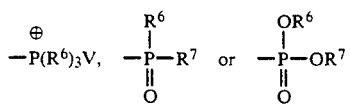

where

R⁶ and R⁷ are identical or different and denote alkyl or phenyl and

V denotes a halide anion or a tosylate anion in inert solvents in the presence of bases, whereby the esters are then optionally hydrolyzed or partially hydrolyzed.

Halide anions are preferably chlorides, bromides or iodides.

Suitable inert solvents for the process according to the invention are those conventional organic solvents which do not change under the reaction conditions. They preferably include ethers such as diethyl ether, butyl methyl ether, dioxane, tetrahydrofuran, glycol dimethyl ether or diethylene glycol dimethyl ether, or hydrocarbons such as benzene, toluene, xylene or petroleum fractions, or amides such as dimethylformamide or hexamethylphosphoric triamide, or 1,3-dimethyl-imidazolidin-2-one, 1,3-dimethyl-tetrahydro-pyridin-2-one or dimethyl sulphoxide. It is likewise possible to use mixtures of the solvents mentioned.

Suitable bases are the conventional basic compounds for basic reactions. These preferably include alkali metal hydrides such as, for example, sodium hydride or potassium hydride, or alkali metal alcoholates such as sodium methanolate, sodium ethanolate, potassium methanolate, potassium ethanolate or potassium tert.butylate, or amides such as sodium amide or lithium diisopropylamide, or organolithium compounds such as phenyllithium, butyllithium or methyllithium or sodium hexamethyldisilazane.

The choice of solvent or base depends on the stability, sensitivity to hydrolysis or CH acidity of the respective phophorus compound. Ethers such as diethyl ether, tetrahydrofuran, dimethoxyethane or dioxane, together with a co-solvent such as dimethylformamide or 1,3-dimethyl tetrahydropyridin-2-one or 1,3-dimethylimidazolid-2-one, are particularly preferably used as solvent. Alkali metal alcoholates such as potassium tert.butylate, or organollithium compounds such as phenyllithium or butyllithium or sodium hydride are particularly preferably used as bases.

The reaction is generally carried out in the temperature range from −80° C. to +70° C., preferably from −80° C. to +20° C.

The reaction may be carried out at atmospheric, elevated or reduced pressure (for example, 0.5 to 5 bar). In general, the reaction is carried out at atmospheric pressure.

When carrying out the reaction the phosphorus compounds are generally employed in an amount of from 1 to 2 moles, preferably in molar amounts, relative to 1 mole of the aldehyde. The bases are generally employed in an amount of from 1 to 5, preferably from 1 to 2 moles, relative to 1 mole of the phosphorus compound.

The process according to the invention can be carried out for example by adding the base and then the aldehyde, if appropriate in a suitable solvent, to the phosphorus compounds dissolved or suspended in a suitable solvent, and if appropriate, heating the mixture. The working up is effected in a conventional manner by extraction, chromatography and/or crystallization.

When carrying out the process according to the invention, it is likewise possible to employ the appropriate phosphoranes [(R⁶)₃P=CHR], which have previously been prepared from the appropriate phosphonium salts and bases in a separate reaction, directly in place of the phosphonium salts (W=—P(R⁶)₃⊕T⊖). However, it has proven favorable to carry out the reaction with the phosphorus compounds in the presence of bases as a onepot process.

The phosphorus compounds of the general formula (IIIa)

$$R'-CH_2-U \qquad (IIIa)$$

where

R¹ and U have the abovementioned meanings are new.

Depending on the meaning of Z, the compounds can be prepared as illustrated, for example, by the following equations:

Process A - First Variant (Z = direct bond) (T = O or a direct bond)

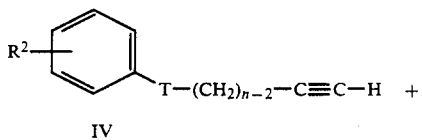

IV

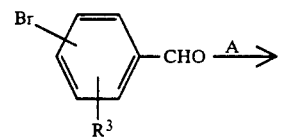

V

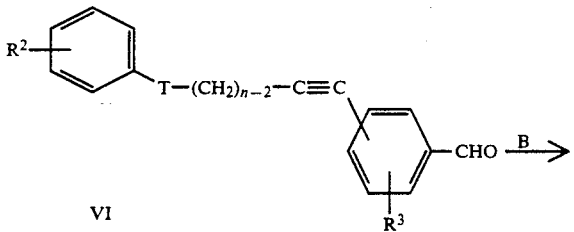

VI

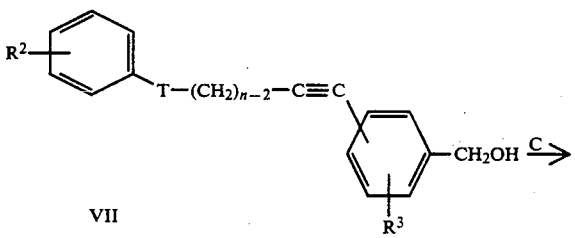

VII

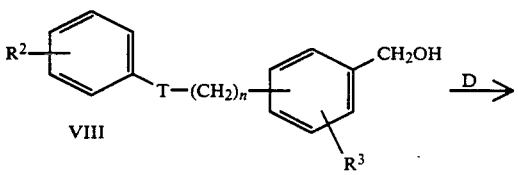

VIII

-continued
Process A - First Variant

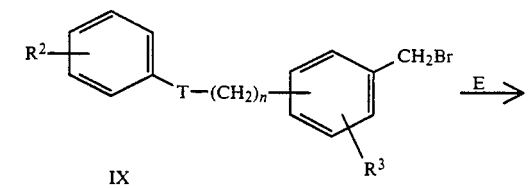

IX

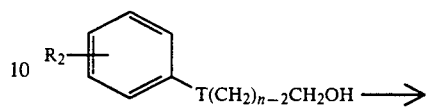

X

PROCESS A—FIRST VARIANT

In the first reaction step [A] of this variant the acetylene compounds (IV) are reacted with a bromobenzaldehyde (V) in solvents such as triethylamine, acetonitrile, pyridine or mixtures thereof, preferably in triethylamine, in the presence of copper (I) salts and palladium (O) compounds preferably in the presence of copper (I) halides, such as for example copper iodide and bis-(triphenylphosphine)-palladium(II)-chloride, in a temperature range of from $-40°$ C. to $+80°$ C., preferably from $0°$ C. to $+40°$ C. In the second reaction step [B] the formyl compound (VI) is reduced to the hydroxyl compounds (VII) in solvents such as alcohols, for example, methanol, ethanol, propanol or isopropanol, or ethers such as diethyl ether, tetrahydrofuran or dioxane, or in bases such as triethylamine, pyridine or dimethylformamide, or water or in mixtures of the stated solvents, using complex hydrides, such as, for example, boron hydrides or aluminium hydrides, preferably sodium hydridoborate or lithium aluminium hydride as reducing agents, in a temperature range of from $-40°$ C. to $+60°$ C., preferably from $0°$ C. to $+40°$ C.

In the third reaction step [C] the compounds (VII) are hydrogenated in inert solvents such as alcohols, for example, methanol, ethanol, propanol or isopropanol, or hydrocarbons such as benzene, toluene or xylene, or in others such as diethyl ether or tetrahydrofuran, or ethyl acetate, preferably in methanol, in the presence of noble metal catalysts such as palladium or platinum, in a temperature range of from $-30°$ C. to $+80°$ C., preferably from $0°$ C. to $+40°$ C., under a pressure of from 1 bar to 50 bars, preferably from 1 bar to 20 bars. Steps B and C may be reversed in order. In the fourth step [D] the hydrogenated compounds (VIII) are brominated by reacting them with brominating agents such as for example phosphorus tribromide, sulphonyl bromide, hydrogen bromide or tetrabromomethane/triphenylphosphine in inert solvents, such as ether, for example diethyl ether or tetrahydrofuran, or hydrocarbons such as benzene or toluene or preferably chorinated hydrocarbons such as methylene chloride or chloroform, in a temperature range of from $-20°$ C. to $+60°$ C., preferably from $0°$ C. to $+40°$ C. In the fifth reaction step [E] the brominated compounds (IX) are reacted with triphenylphosphine in inert solvents such as acetonitrile or hydrocarbons such as benzene, toluene or xylene, or benzonitrile or dimethylformamide or dimethyl sulphoxide or an alcohol such as methanol, ethanol, propanol or isopropanol or without solvent, in a temperature range of from $0°$ C. to $+200°$ C., preferably from $+20°$ C. to $+180°$ C., to give the phosphonium salts (X).

Process A - second variant
(Z = direct bond)   (T = O or a direct bond)

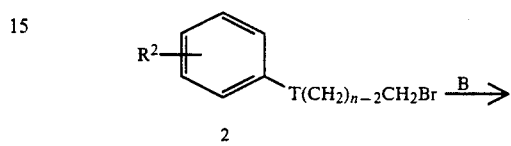

1

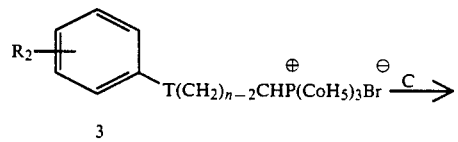

2

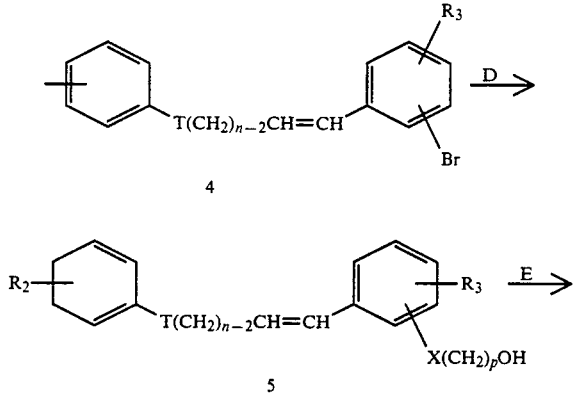

3

4

5

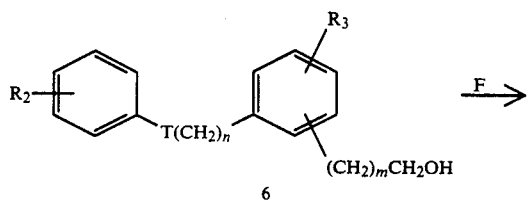

6

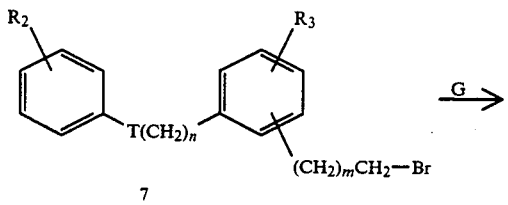

7

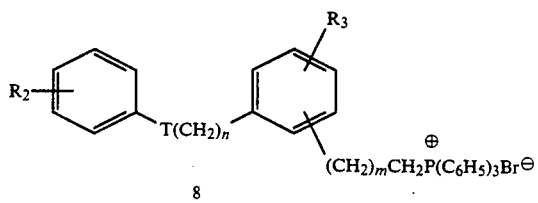

8

In the first reaction step [1] are brominated by reacting them with brominating agents such as for example those listed in Process A-First variant-step D.

[B] Bromides (2) are reacted with triphenylphosphine as in Process A-First variant-step E.

[C] Is a process generating the reactive phosphorane as detailed earlier in the reaction of compound III and reacting it with a bromobenzaldehyde of the desired substitution pattern.

[D] Where X denotes a direct bond. Reaction of the bromide (4) with a suitable base preferably t-butyllithium in an inert solvent (tetrahydrofuran) at low temperature followed by addition of a suitable electophile such as paraformaldehyde (V, p=1) or ethylene oxide (V, p=2) gives the primary alcohols.

Alternatively X denotes a triple bond and reaction with an optionally protected hydroxyalkyne such as the tetrahydropyranyl ether of propargylalcohol using the process step [A] of process A-First variant.

[E] Is a hydrogenation as described in step C of process A-First Variant.

[F] and [G] are identical to [A] and [B] respectively.

carbonate, potassium carbonate, sodium hydroxide, potassium hydroxide, sodium ethanolate or potassium tert. butylate, in a temperature range of from 0° C. to +200° C., preferably from +20° C. to 180° C. In the second step [B] the phenyl ethers XIII are reacted with tosyl chloride in inert solvents such as ether, for example diethylether, tetrahydrofuran or dioxane, or hydrocarbons such as benzene or toluene, or chlorinated hydrocarbons such as chloroform or methylene chloride, or ethylacetate, acetone or acetonitrile, preferably in methylene chloride, in the presence of bases such as triethylamine, diisopropylamine, pyridine or dimethylaminopyridine, preferably in the presence of pyridine, in a temperature range of from −30° C. to +50° C., preferably from −10° C. to +30° C. In the third reaction step [C] the tosyl compounds (XIV) are reacted with triphenylphosphine in suitable solvents such as hydrocarbons, for example, benzene or toluene, benzonitrile, acetonitrile, dimethylformamide or dimethylsulphoxide or without solvent, preferably in acetonitrile, in a temperature range from 0° C. to +200° C., preferably from +20° C. to +180° C., to give the phosphonium salts (XV).

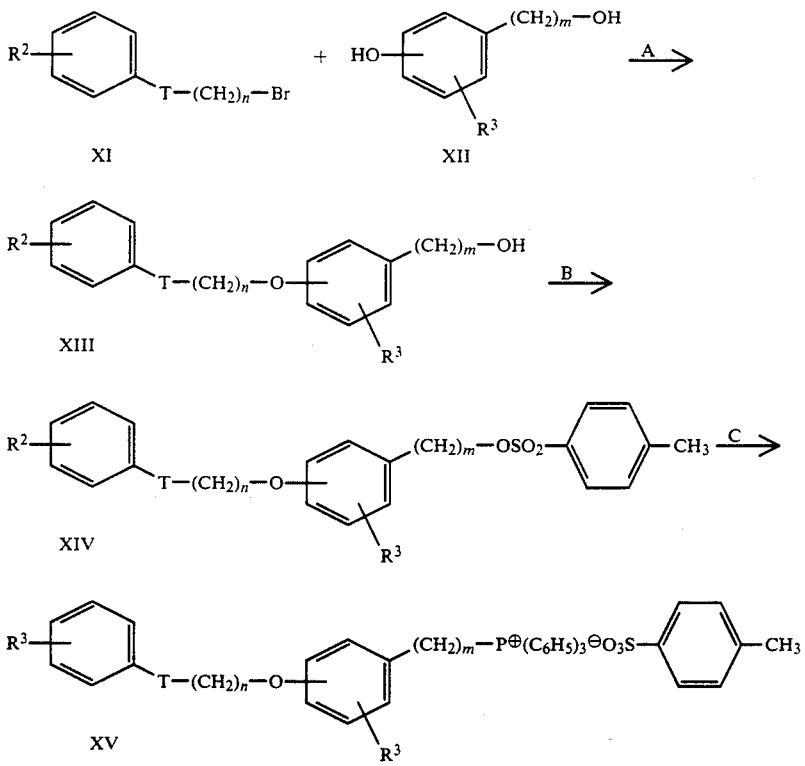

PROCESS VARIANT B

In the first reaction step [A] of this variant the bromine compounds (XI) are reacted with the phenols (XII) in suitable solvents such as water, or alcohols such as for example methanol, ethanol, propanol or isopropanol, or ethers such as diethyl ether, tetrahydrofuran, dioxane or dimethyloxyethane, or dimethylformamide or dimethylsulphoxide, preferably in isopropanol, in the presence of bases such as alkali metal hydroxides, carbonates or alcoholates, such as, for example, sodium The aldehydes of the general formula (II) are new.

Depending on the meaning of X and Y they can be prepared as illustrated for example by the following equations:

Process C (X = CH₂ and Y = CH₂, S)

-continued
Process C

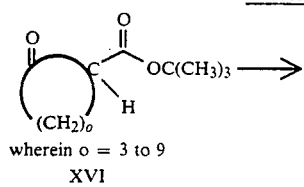

wherein o = 3 to 9
XVI

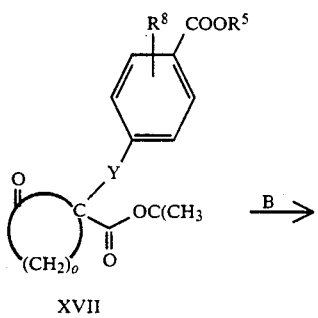

XVII

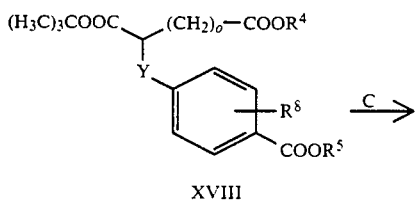

XVIII

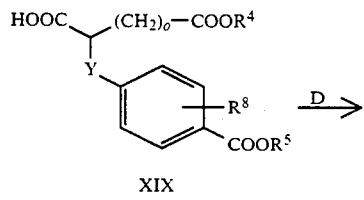

XIX

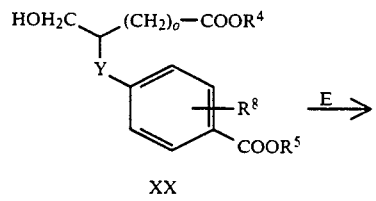

XX

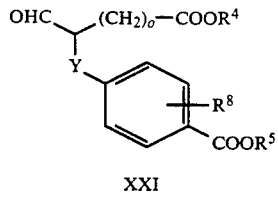

XXI

PROCESS VARIANT C

In the first reaction step [A] of this variant the ketone (XVI) is reacted with 4-chloromethylbenzoic acid esters in inert solvents such as ether, for example, diethylether, tetrahydrofuran or dioxane, or dimethylformamide, or dimethylsulphoxide, or mixtures thereof, preferably in dimethylformamide, in the presence of bases such as alkali metal hydrides, amides or alcoholates, such as sodium hydride, potassium hydride, lithium diisopropylamide, potassium ethylate, sodium ethylate, potassium methylate or potassium tert, butylate, preferably in the presence of sodium hydride, in a temperature range of from −40° C. to +60° C., preferably from −20° C. to +30° C. In the second reaction step [B] the cyclohexanones (XVIII) are reacted in suitable solvents such as dimethylformamide or alcohols, for example, methanol, ethanol, propanol or isopropanol, or water, or mixtures therefore, preferably in dimethylformamide or ethanol, in the presence of bases such as alkali metal hydroxides, alkali metal carbonates of alkali metal alcoholates, such as sodium hydroxide, potassium hydroxide, sodium carbonate, sodium methanolate, sodium ethanolate, potassium ethanolate or potassium tert. butanolate, preferably in the presence of potassium tert. butanolate, in a temperature range of from 0° C. to +150° C., preferably from +20° C. to +100° C., to give the triesters XVIII. In the third reaction step [C] the triesters (XVIII) are saponified in suitable solvents such as alcohols such as, for example, methanol, ethanol, propanol or isopropanol, or ethers, such as methyl ether, tetrahydrofuran or dioxane, or chlorinated hydrocarbons such as methylene chloride or chloroform, or carboxylic acids such as acetic acid or trifluoroacetic acid or mixtures thereof, preferably in trifluoroacetic acid, in the presence of acids such as mineral acids, for example hydrochloric acid, hydrobromic acid or sulphuric acid, or carboxylic acids such as acetic acid or trifluoroacetic acid, preferably in the presence of acetic acid, particularly preferably using trifluoroacetic acid, both as the solvent and the acid, in a temperature range of from −20° C. to +60° C., preferably from 0° C. to +30° C., to give the carboxylic acids XIX. In the fourth step [D] the carboxylic acids (XIX) are reduced in suitable solvents such as ethers, for example, diethylether, tetrahydrofuran or dioxane, or chlorinated hydrocarbons such as methylene chloride or chloroform, or mixtures thereof, preferably in tetrahydrofuran, using boron compounds as reducing agents, such as, for example, borane or the borane dimethylsulphide complex, in a temperature range of from −40° C. to +60° C., preferably from −20° C. to +30° C. to give the hydroxyl compounds (XX). In the fifth reaction step [E] the hydroxy compounds (XX) are oxidized in suitable solvents such as ether, for example, diethyl ether, dioxane or tetrahydrofuran, or chlorinated hydrocarbons such as methylene chloride or chloroform, or dimethyl sulphoxide, or mixtures thereof, preferably in dichloromethane, using oxidizing agents such as pyridinium chlorochromate, chromium (VI) salts, dimethyl sulphoxide/pyridine/SO$_3$, preferably using pyridinium chlorochromate, if appropriate in the presence of bases such as triethylamine, di isopropylamine, pyridine or dimethylaminopyridine, preferably in the presence of triethylamine, in a temperature range of from −20° C. to +60° C., preferably from 0° C. to +30° C., to give the aldehydes (XXI).

Process D
(X = S, Y = CH$_2$)

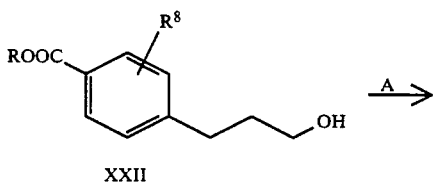

XXII

-continued
Process D
(X = S, Y = CH₂)

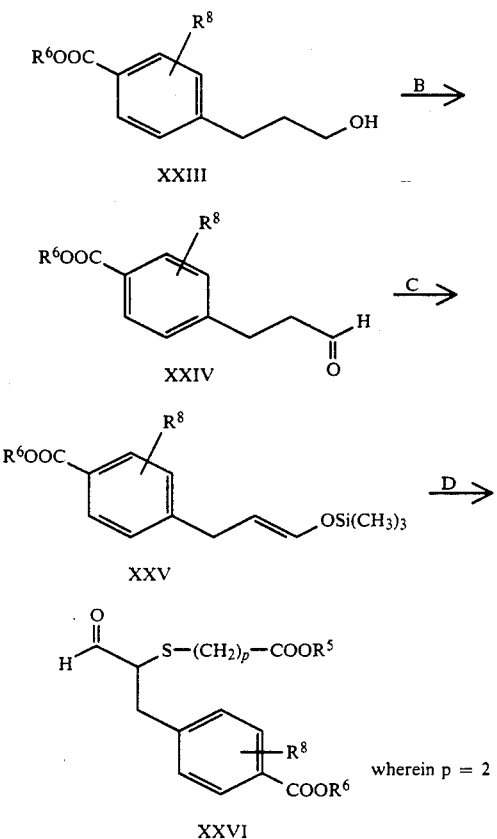

wherein p = 2 or 3

PROCESS VARIANT D

In the first reaction step [A] of this variant the benzoic acid mixture (XXII) is converted into the ester (XXIII) in suitable solvents such as alcohols, for example, methanol, ethanol, propanol or isopropanol, or water, or mixtures thereof, preferably in methanol, in the presence of acids such as mineral acids, for example, hydrochloric acid, hydrobromic acid or sulphuric acid or carboxylic acids such as acetic acid or trifluoroacetic acid, or preferably in the presence of thionyl chloride, in a temperature range of from −40° C. to +60° C., preferably from −20° C. to +40° C. In the second reaction step [B] the esters (XXIII) are oxidized in suitable solvents such as ether, for example, diethyl ether, tetrahydrofuran or dioxane, or dimethyl sulphoxide, or chlorinated hydrocarbons such as methylene chloride or chloroform, or mixtures thereof, preferably in methylene chloride, using oxidizing agents such as bromine (VI) salts, pyridinium chlorochromate, dimethyl sulphoxide/oxalyl chloride or dimethyl sulphoxide/pyridine/SO₃, preferably using dimethyl sulphoxide/oxalyl chloride as oxidizing agents, in the presence of bases such as triethylamine, diisopropylamine, pyridine or dimethylaminopyridine, preferably in the presence of triethylamine, in a temperature range of from −80° C. to +40° C., preferably from −60° C. to +20° C. to give the aldehydes (XXIV). In the third reaction step [C] the aldehydes (XXIV) are converted into the silicon compounds (XXV) in suitable solvents such as hydrocarbons such as benzene, toluene or xylene, or dimethyl sulphoxide, or amides such as dimethyl formamide or hexamethylphosphoric acid triamide, or mixtures thereof, preferably in dimethyl formamide, in the presence of bases such as triethylamine, diisopropylamine, pyridine or dimethylaminopyridine, preferably in the presence of triethylamine, in a temperature range of from 0° C. to +200° C., preferably from +20° C. to +180° C. In the fourth reaction step these silicon compounds (XXV) are converted with 4,4'-dithiodibutyric acid dimethyl ester or 3,3'-dithiodipropanoic acid dimethyl ester in the presence of sulfuryl chloride or chlorine or bromine into the aldehydes (XVI) in suitable solvents such as ether, for example, diethylether, tetrahydrofuran or dioxane, or hydrocarbons such as benzene or toluene, or chlorinated hydrocarbons such as methylene chloride or chloroform, or mixtures thereof, preferably in methylene chloride, if appropriate in the presence of bases, such as triethylamine or diisopropylamine or pyridine, in a temperature range of from −80° C. to +20° C., preferably from −70° C. to 0° C.

Process E
(X = CH₂, Y = direct bond)

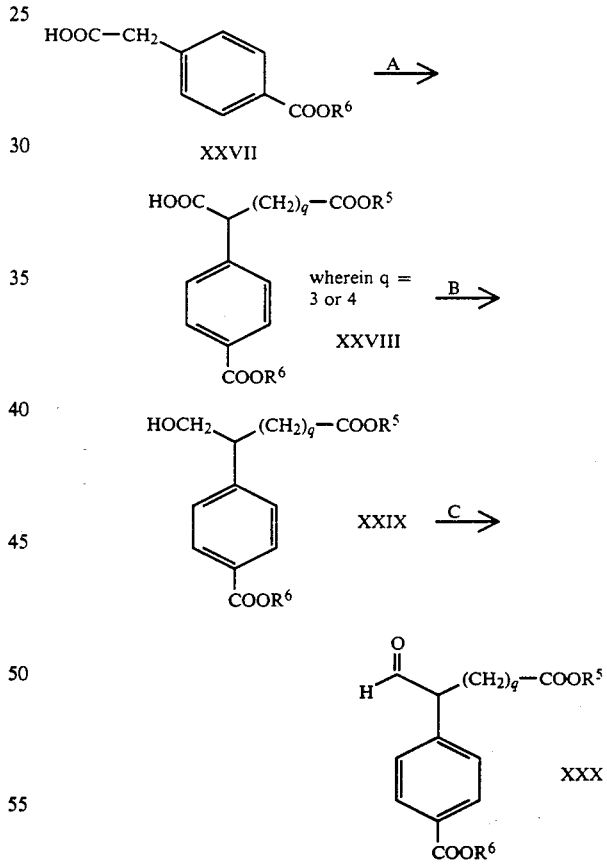

PROCESS VARIANT E

In this variant benzoic acid (XXVII) is reacted in suitable solvents such as ether, for example, diethyl ether, tetrahydrofuran, dioxane, diethylene glycol monomethylether or diethylene glycol diethyl ether, or amides such as dimethyl formamide or hexamethylphosphoric acid triamide, 1,3-dimethylimidazolidin-2-one or 1,3-dimethyltetrahydropyridin-2-one, or mixtures thereof, preferably in tetrahydrofuran, in the presence of organometallic compounds as the base, such as, for example, organic lithium, sodium or potassium compounds, preferably butyllithium, methyllithium, phenyllithium, sodium naphthalide, potassium naphthalide, lithium diisopropylamide or lithium hexamethyldisilazane, preferably in the presence of lithium diisopropylamide as the base, in a temperature range of from −80° C. to +60° C., preferably from −50° C. to +30° C., to give the compounds (XVIII), which are then reduced in the second reaction step [B] in suitable solvents such as ether, for example, diethyl ether, tetrahydrofuran or dioxane, or chlorinated hydrocarbons such as methylene chloride or chloroform, or mixtures thereof, preferably in tetrahydrofuran, using boranes as reducing agents, preferably using borane or borane dimethyl sulphide complex, in a temperature range of from −40° C. to +60° C., preferably from −20° C. to +30° C., to give the hydroxy compounds (XXIX). In the third reaction step [C] the hydroxy compounds (XXIX) are oxidized in suitable solvents such as ether, for example, diethyl ether, tetrahydrofuran or dioxane, or chlorinated hydrocarbons such as methylene chloride or chloroform, or dimethyl sulphoxide, or mixtures thereof, preferably in dichloromethane, using oxidizing agents such as chromium VI salts, pyridinium chlorochromate, dimethyl sulphoxide/oxalyl chloride or dimethyl sulphoxide/pyridine/SO$_3$, preferably using pyridinium chlorochromate as the oxidizing agent, if appropriate in the presence of bases such as triethylamine, diisopropylamine or pyridine, preferably in the presence of triethylamine, in a temperature range of from −80° C. to +60° C., preferably from −60° C. to +30° C., to give the aldehydes (XXX).

Process F (X = CH$_2$ or direct bond, Y = S or X = S, Y = CH$_2$ or direct bond)

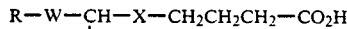

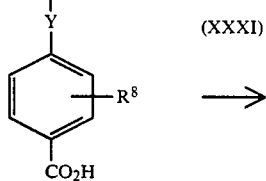

(X' = CH$_2$ or direct bond, Y' = SO or SO$_2$ or X' = SO or SO$_2$, Y' = CH$_2$ or direct bond)

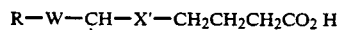

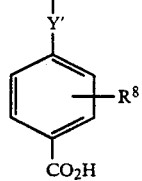

PROCESS VARIANT F

X'=CH$_2$ or direct bond, Y'=SO$_2$ or X'=SO$_2$, Y'=CH$_2$ or direct bond

In this variant acid (XXXI) is reacted in suitable solvents such as alcohols, water, acetone or acetonitrile with an oxidizing agent such as hydrogen peroxide, nitric acid, peracids, oxygen, ozone, organic peracids, potassium permangerate, potassium persulfate, sodium hypochlorite, hypochlorous acid, rutherium tetroxide, oxides of nitrogen, anodic oxidation or with special mixture such as oxone in a usual temperature range of from −20° C. to +30° C., although for specially unsuitable substances even lower temperature ranges (−78° C.) may be necessary. The product of this process is sulfone (XXXII, X' or Y'=SO$_2$).

PROCESS VARIANT G

X'=CH$_2$ or direct bond, Y'=SO or X'=SO, Y'=CH$_2$ or direct bond

In this variant acid (XXXI) is reacted as in variant E, but with less oxidizing agent and/or at a lower temperature or with oxidizing agents such as hydroperoxides, manganese dioxide, selenium dioxide, peracids, chromic acid or iodosobenzene. The product of this process is sulfoxide (XXXII, X' or Y'=SO).

Process H
(W = CH$_2$CH$_2$, R contains no double bonds but may contain aryl)

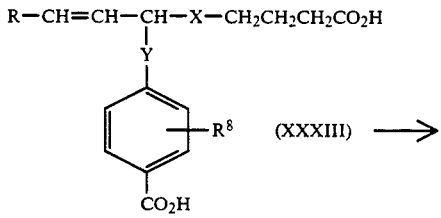

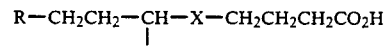

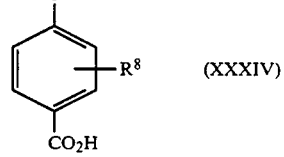

In this process acid XXXIII is reacted in suitable solvents such as alcohols, water, benzene, toluene, ethers such as diethylether, tetrahydrofuran, dioxane or esters such as ethyl acetate or hydrocarbons such as hexane or amines such as triethylamine or ammonia with a suitable reducing agent such as hydrogen in the presence of a metal catalyst such as oxides or soluble complexes of paladium, platinum, rutherium or nickel or with a metal such as lithium or sodium or with hydrazine or aryl aralkoxy substituted hydrazines. The product of this reaction is acid (XXXIV) in which W or the generic structure (I) is —CH$_2$CH$_2$—. The usual temperature range for this process is from −20° C. to +30° C.

Process I
For o = 1 to 6

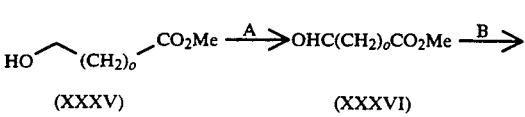

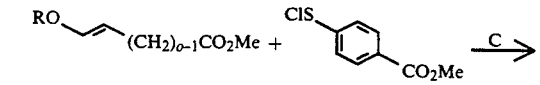

-continued
Process I

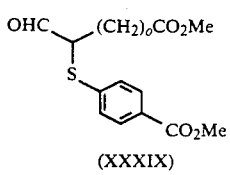

(XXXIX)

This process variant is directly analogous to that described in process D and offers an alternative to process C for the case where Y=S. However, it is applicable for rather more than o=3 or 4 as in process C.

The three steps are as described:

[A] is equivalent to step E of process C

[B] is equivalent to step C of process D when R=trimethylsilyl.

Alternatively R=alkyl e.g. methyl and step B is performed by addition of the aldehyde to a solution of an alkoxymethylene ylide. The latter is generated from an alkoxymethylene triphenylphosphonium salt as described earlier for the reaction of compound III with II.

[C] is equivalent to step D or process D.

Process J
X = CH$_2$, bond or S
Y = bond

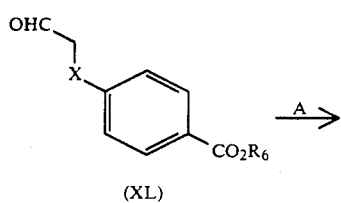

(XL)

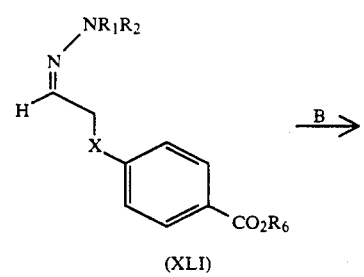

(XLI)

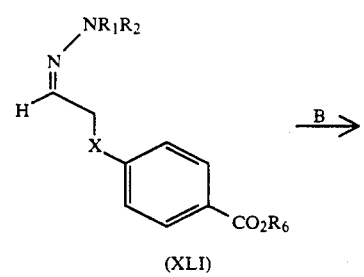

(XLII)

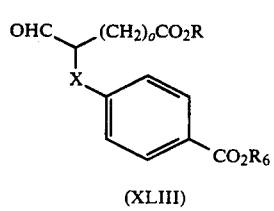

(XLIII)

Process K
X = S or CH$_2$
Y = bond

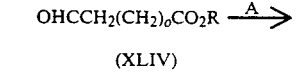

(XLIV)

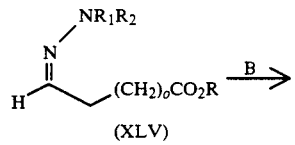

(XLV)

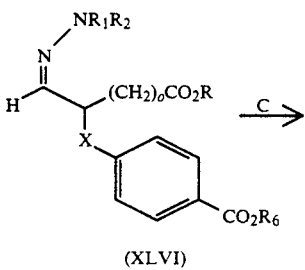

(XLVI)

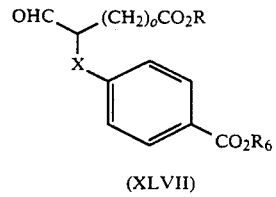

(XLVII)

These variants of a similar process offer two routes to aldehydes XLIII or XLVII.

Step A is identical in both processes namely the reaction of an aldehyde XL or XLIV with a dialkylaminohydrazine such as dimethylhydrazine (E. J. Corey and D. Enders, Chem. Ber., 111,1337, 1363, (1978), or (R) (or (S)) 1-amino-2-methoxymethylpyrrolidine (D. Enders et al. Org. Syn., 65, 183, (1987)). The use of these chiral hydrazones (RAMP or SAMP) allows the subsequent step to proceed with virtually complete enantioselectivity so that the product of step B may be a single enantiomer. Thus obviating the need for resolution of products such as XLIII or XLVII by other means. Step A is best achieved by mixing of the aldehyde and hydrazine in the absence of solvent and heating to 60°-70° C. for an appropriate time (1 day) under an inert atmosphere.

Step B is effected in suitably inert solvents such as diethylether or tetrahydrofuran at reduced temperature, preferably 0° C., with an appropriate organometallic base such as butyllithium or lithium diisopropylamide followed by the addition of an appropriate electrophile (RO$_2$C(CH$_2$)$_n$Hal, R$_6$O$_2$C C$_6$H$_4$CH$_2$Hal or RO$_2$C C$_6$H$_4$SCl) to give the alkylated product XLII or XLVI.

Step C is an oxidative cleavage of the hydrazones to give the aldehydes XLIII or XLVII using e.g. ozone in a suitable solvent (dichloromethane) at low temperature (−78° C.) when the chiral hydrazones are used. The dimethyl hydrazones may be cleaved with sodium periodate in aqueous solution or by methylation with methyl iodide followed by addition of acid.

Process L
(X = O, Y = direct bond)

-continued
Process L

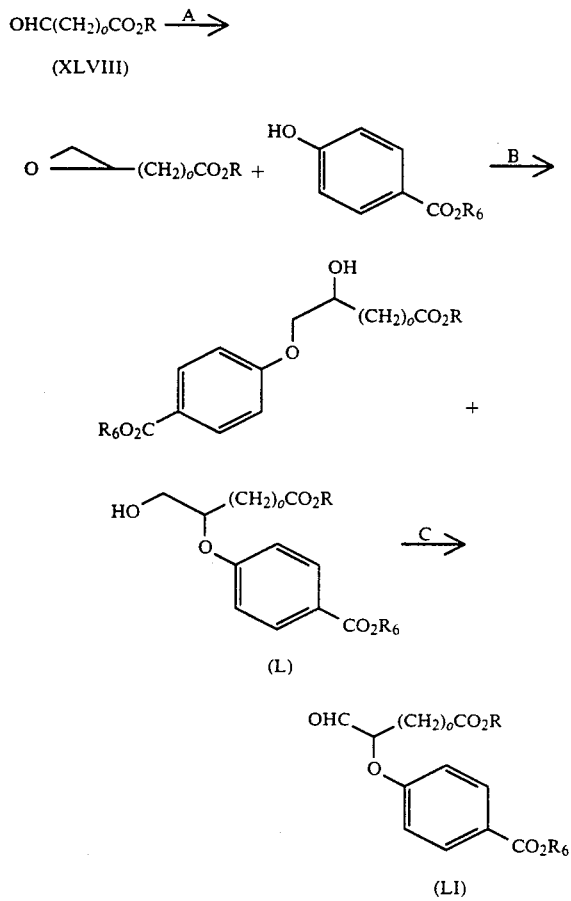

Process M
(X = O, Y = direct bond)

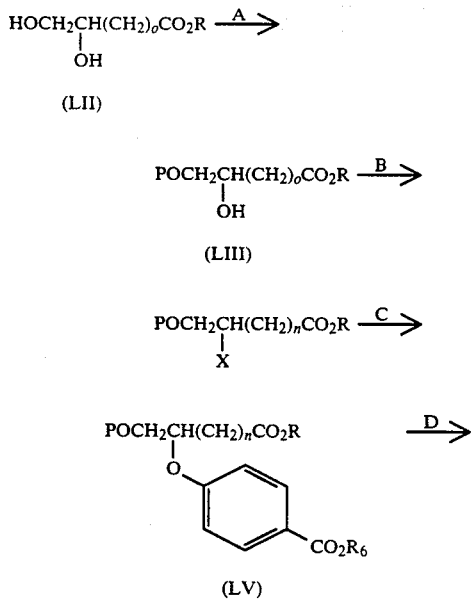

-continued
Process M

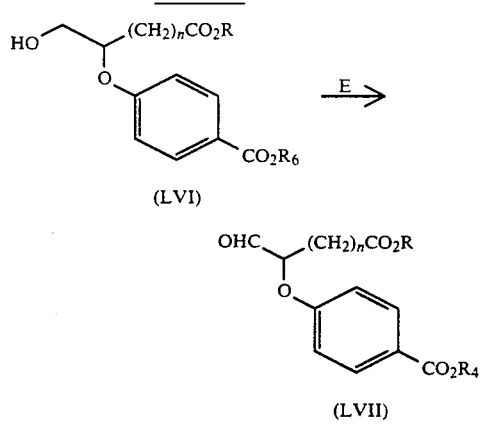

These processes illustrate two ways of preparing an aldehyde LI or LVII where X=oxygen.

In the first instance an ω-oxoalkanoate (XLVIII) [or as ω-oxoalkenoate is reacted with sulphonium methylide (E. J. Corey et al, *J. Am. Chem. Soc.* 87, 1353, (1965))] in a suitable inert solvent to give an epoxide XLIX.

The epoxide undergoes nucleophilic ring opening with a phenol in a variety of solvents such as methanol to give two regioisomers from which the desired isomer L is readily obtained by chromatography. The yield and ratio of the two isomers may be manipulated by altering the solvent and by use of a variety of catalysts.

Step C is a simple oxidation as already detailed in process E step C.

Alternatively a diol LII is monoprotected with a suitable protecting group such as tetrahydropyranylether, t-butyldimethylsilyl ether, tert-butyldiphenylsilylether to give a secondary alcohol LIII. Step B involves the conversion of the alcohol into a suitable leaving group X such as tosylate or halide (preferably bromide or iodide) by methods already detailed in other processes.

Step C involves replacement of the leaving group by a phenoxy group essentially as described in Step A of process B.

Step D involves selective removal of the protecting group P by a mild method appropriate to the given P.
Step E is a simple oxidation as above.

PROCESS N (B=ortho or meta $CO_2H$ or ortho or meta or para $CH_2CO_2H$, $CHN_4$, $CONR^{10}R^{11}$)

All the processes illustrate the preparation of β-disubstituted aldehydes with a para alkoxycarbonyl group. Clearly in all these cases it is possible to use a meta, or ortho, disubstituted benzoate instead of the para disubstituted compound.

Similarly the alkoxycarbonyl group can be replaced by an alkoxycarbonylmethyl group to give a product where $A=CH_2CO_2H$. The introduction of a tetrazole group is best effected by use of a suitable monosubstituted benzonitrile to give intermediates where A=nitrile. This is then converted to a tetrazole by reaction with sodium azide in the presence of a salt of a suitable tertiary base (triethylamine or morpholine hydrochloride) in an inert solvent (dimethylformamide) at elevated temperature.

The introduction of amides or sulphonamides is best effected by a judicious choice of esters at the aromatic and aliphatic carboxyl groups so that either carboxyl group may be selectively liberated. The said carboxyl group can then be reacted with an aryl, or alkyl, sulphonamide in the presence of a dimide such as dicyclohexylcarbodiimide in a suitably inert solvent. Alternatively the carboxylic acid can be suitably activated by e.g. reaction with diphenyl phosphinic chloride and then treated with the desired amine to give an amide.

The compounds of the general formula (I) according to the invention have pharmacological properties and in particular they are antagonists for leucotriene diseases: asthma, circulatory diseases, respiratory diseases. They can therefore be used as pharmaceuticals.

The new active compounds can be converted in a known manner into the customary formulations, such as tablets, dragees, pills, granules, aerosols, syrups, capsules, emulsions, suspensions and solutions, using inert non-toxic, pharmaceutically suitable excipients or solvents. The therapeutically active compound should in each case be present in a concentration of about 0.5 to 98% preferably 1 to 90%, by weight of the total mixture, that is to say in amounts which suffice to achieve the dosage range indicated.

The formulations are prepared, for example, by extending the active compounds with solvents and/or excipients, optionally with the use of emulsifiers and/or dispersing agents, and, for example, when using water as a diluent, organic solvents can optionally be used as auxiliary solvents.

Examples of auxiliary substances which may be mentioned are: water, non-toxic organic solvents, such as paraffins (for example, petroleum fractions), vegetable oils (for example, groundnut oil/sesame oil), alcohols (for example, ethyl alcohol and glycerol), excipients, such as, for example, ground natural mineral (for example, kaolins, aluminas, talc and chalk), ground synthetic mineral (for example, highly disperse silica and silicates) and sugars (for example, sucrose, lactose and glucose), emulsifiers (for example, polyoxyethylene fatty acid esters), polyoxyethylene fatty alcohol ethers (for example, lignin, sulphite waste liquors, methylcellulose starch and polyvinylpyrrolidone) and lubricants (for example, magnesium stearate, talc, stearic acid and sodium sulphate).

Administration is effected in the customary manner, preferably orally, by inhalation or parenterally, particularly perlingually or intravenously. In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl sulphate and talc, can be used concomitantly in the production of tablets. In the case of aqueous suspensions, the active compounds can be mixed with various flavor-improving agents or colorants in addition to the abovementioned auxiliary substances.

In the case of parenteral use, solutions of the active compounds, using suitable liquid excipients, can be employed.

In general, it has proved advantageous, in the case of intravenous administration, to administer amounts of about 0.001 to 1 mg/kg, preferably about 0.01 to 0.5 mg/kg, of body weight to achieve effective results, and in the case of oral administration, the dosage is about 0.01 to 20 mg/kg, preferably 0.1 to 10 mg/kg of body weight.

Nevertheless, it may be necessary, under certain circumstances, to deviate from the amounts mentioned, and in particular to do so as a function of the body weight or of the nature of the administration method, of the individual reaction towards the medicament, the nature of its formation, and the time or interval over which the administration takes place. Thus, it can in some cases suffice to use the minimum amount, whereas in other cases the upper limit mentioned must be exceeded. In the case of administration of larger amounts, it may be advisable to divide these into several individual administrations over the course of the day.

PREPARATION EXAMPLES

EXAMPLE 1

5-Phenoxy-1-pentyne

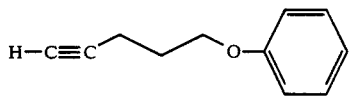

A 2.81 g (58.5 mmol) portion of sodium hydride (50% in oil) was washed with dry hexane and then dried in vacuo. The residue was slurried in 20 ml of anhydrous tetrahydrofuran under argon with 0° C. bath cooling and a solution of 5.51 g (58.5 mmol) of phenol in 20 ml tetrahydrofuran was added dropwise. After vigorous gas evolution had ceased a 10 ml portion of anhydrous hexamethylphosphoryltriamide was added followed by a solution of 4.85 g (47.3 mmol) of 5-chloro-1-pentyne in 7 ml tetrahydrofuran. The resulting grey solution was refluxed for 3 days. The resulting mixture was cooled, diluted with hexane and washed with water. It was then washed with aqueous potassium carbonate to remove the residual phenol. The resulting solution was dried over magnesium sulfate and evaporated in vacuo. The orange oily residue was distilled using an aspirator vacuum to yield 6.48 g pure product as a colorless oil.

bp.: 115°–118° C. (23 mm).

Yield: 86% of theory.

TLC-R$_f$: 0.62 (methylenechloride).

NMR (CDCl$_3$, 300 MHz): 1.94–2.06 [3] m, 2.35–2.44 [2] m, 4.05 [2] t, J=7 Hz, 6.86–6.97 [3] m, 7.1–7.3 [2] m.

EXAMPLE 2

4-(5-Phenoxy-1-pentyn-1-yl)benzaldehyde

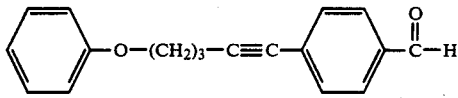

A solution of 2.08 g (13.0 mmol) of 5-phenoxy-1-pentyne and 2.00 g (10.81 mmol) of 4-bromobenzaldehyde in 7.0 ml of dry triethylamine was stirred under argon as 0.758 g (1.08 mmol) of bis(triphenylphosphine)palladium(II) was added followed by 103 mg (0.54 mmol) of copper(I)iodide. The reaction mixture turned dark and became warmed as it was stirred over 15 minutes, It was then stirred overnight under argon. It was diluted with ethyl acetate and then washed with 2% sulfuric acid, then water and finally saturated sodium chloride. The resulting solution was dried over a mixture of magnesium sulfate and Norite (decolorizing active carbon), and then filtered and evaporated in vacuo. The orange solid residue was dissolved in minimum benzene and chromatographed on silica gel using 3% ethyl acetate in hexane elution to yield 2.21 g of purified product as a tan solid.

Yield: 77% of theory.

TLC-R$_f$: 0.36 (ethyl acetate:hexane 2:8).

NMR (CDCl$_3$, 60 MHz): 2.1 [2] t, J=7, 2.2 [2] , J=6, 2.7 [2] t, J=7, 4.1 [2] t, J =6, 6.8–7.8 [9] m, 10.1 [1] s.

EXAMPLE 3

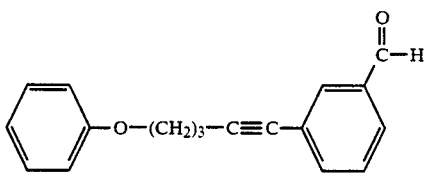

3-(5-Phenoxy-1-pentyn-1-yl)benzaldehyde

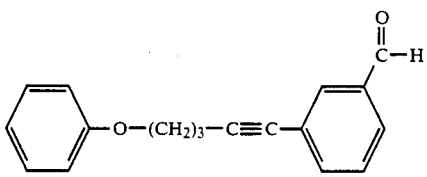

This compound was prepared in a manner analogous to that used for the para isomer (Example 2), 2.00 g (10.8 mmol) of 3-bromobenzaldehyde, 2.087 g (13.0 mmol) of 5-phenoxy-1-pentyne, 7 ml triethylamine, 0.758 g (1.08 mmol) of the palladium compound and 104 mg (0.55 mmol) of copper(I)iodide were used. The reaction was found by analysis to be essentially complete after 16 hours ambient temperature. The crude product which was in the form of an orange oil was chromatographed using 5% ethyl acetate in hexane to yield 1.924 g of a purified product in the form of a yellow oil.

Yield: 67.3% of theory.

TLC-R$_f$: 0.24 (ethyl acetate:hexane 1:9).

NMR (CDCl$_3$, 60 MHz): 2.1 [2] t, 2.2 [2] t, 4.1 [2] t, J=6, 6.8–7.8 [9] m, 10.1 [1] s.

EXAMPLE 4

4-(5-Phenoxy-1-pentyn-1-yl)benzyl alcohol

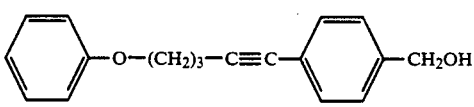

A solution of 2.02 g of 4-(5-phenoxy-1-pentyn-1-yl)benzaldehyde in 5 ml of absolute ethanol was stirred with 0° C. bath cooling and 640 mg of sodium borohydride was added in portions. After stirring for 55 minutes the reaction mixture was quenched by the addition of water and then evaporated in vacuo. The residue was mixed cautiously with 2% sulfuric acid and extracted twice with ethyl acetate. The combined extracts were washed with saturated sodium chloride and then a sodium hydrogen carbonate solution. They were dried over magnesium-sulfate and evaporated in vacuo to yield 2.06 g of the 4-(Phenoxy-1-pentyn-1-yl)-benzyl alcohol which was sufficiently pure to use without purification.

Yield: 100% of theory.

TLC-R$_f$: 0.12 (ethyl acetate:hexane 2:8)

NMR (CDCl$_3$, 60 MHz): 2.09 [2] t, 2.12 [2] t, 2.7 [2] t, 4.1 [2] t, J=6 Hz, 4.6 [2] s, 6.8–7.4 [9] m.

EXAMPLE 5

3-(5-Phenoxy-1-pentyn-1-yl)benzyl alcohol

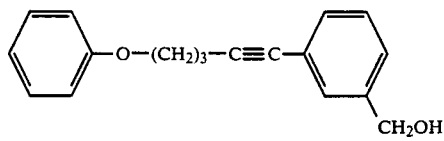

This compound was prepared in a manner analogous to that used for the para isomer (Example 4). Thus 1.924 g of the meta aldehyde were treated with 924 mg of sodium borohydride in 50 ml of absolute ethanol at 0° C. for 1 hour. The yield of the 3-(Phenoxy-1-pentyn-1-yl)benzyl alcohol was 1.89 g of a yellow oil which was used without further purification.

Yield: 93% of theory.

TLC-R$_f$: 0.20 (ethyl acetate:hexane 1:3).

NMR (CDCl$_3$, 60 Mhz): 2.1 [2] t, 2.14 [2] t, 2.7 [2] t, 4.1 [2] t, J=6, 4.6 [2] s, 6.8–7.4 [9] m.

EXAMPLE 6

4-(5-Phenoxypent-1-yl)benzyl alcohol

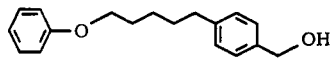

A solution of 0.54 g of 4-(5-phenoxy-1-pentyn-1-yl)benzyl alcohol in 100 ml methanol was treated with 230 mg of 5% palladium on charcoal and 58 PSI hydrogen for 3.5 hours The product mixture was filtered using celite and the filtrate was evaporated in vacuo to yield 0.53 g of the compound in the heading in the form of a light tan solid which was used without purification.

Yield: 98% of theory.

NMR (CDCl$_3$, 60 MHz): 1.6 [6] m, 2.6 [2] t, J=6, 3.2 [1] bs, 3.8 [2] t, J=6, 4.5 [2] s, 6.8–7.3 [9] m.

EXAMPLE 7

3-(5-Phenoxypent-1-yl)benzylalcohol

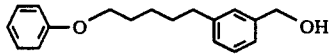

This compound was prepared in a manner analogous to that used for the para isomer (Example 6). Thus 1.856 g of 3-(5-phenoxy-1-pentyn-1-yl)benzyl alcohol in 100 ml of CH$_3$OH was treated with 333 mg 5% palladium on charcoal and 30 PSI hydrogen for 1.25 hours. The product mixture was filtered in the customary manner through celite and the filtrate was evaporated in vacuo to yield 1.89 g of the 3-(5-Phenoxypent-1-yl)benzyl alcohol in the form of a tan solid.

Yield: 100% of theory

NMR (CDCl$_3$, 60 MHz): 1.6 [6] m, 2.3 [1] bs, 2.6 [2] t, 3.9 [2] t, J=6, 4.6 [2] s, 6.8–7.3 [9] m.

EXAMPLE 8

4-(5-Phenoxypent-1-yl)benzyl bromide

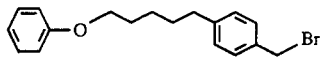

A solution of 518 mg (1.92 mmol) 4-(5-phenoxypent-1-yl)benzyl alcohol in 3.5 ml of dry methylene chloride was stirred under argon as 826 mg (2.49 mmol) of carbon tetrabromide were added followed by 653 mg (2.49 mmol) of triphenylphosphine. The reaction mixture turned yellow and heated briefly to reflux. The resulting mixture was stirred under argon for 1.5 hours and it was then evaporated in vacuo. The residue was dissolved as far as possible in a small quantity of warm benzene and chromatographed on silica gel using 2.5% ethyl acetate in hexane elution. The insoluble benzene material was shown by tlc to be a non-usable product. The product which was still not pure was rechromatographed using cyclohexane to apply the material to the column. 376 mg of a usable pure product plus a smaller amount (56 mg) of a mixed fraction consisting mostly of the product along with a more polar contaminant were isolated.

Yield: 59% of theory were obtained.
TLC-$R_f$: 0.33 (ethyl acetate:hexane 5:95)
NMR (CDCl$_3$, 60 MHz): 1.5–2.0 [6] m, 2.6 [2] t, J=6, 3.9 [2] t, J=6, 4.4 [2] s, 6.8–7.4 [9] m.

EXAMPLE 9

2-[4-(4-Phenoxybutoxy)phenyl]ethanol

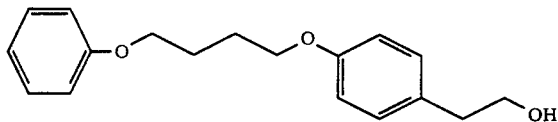

A mixture of 10.31 g (45 mmol) of 4-phenoxybutylbromide, 6.22 g (45 mmol) of 2-(4-hydroxyphenyl)ethanol and 6.22 g (45 mmol) of pulverized potassium carbonate in 45 ml of isopropanol was refluxed for 24 hours. The resulting mixture was cooled, mixed with water and then extracted three times with ethyl acetate. The combined extracts were washed with water and then with saturated aqueous sodium bicarbonate. They were dried over sodium sulfate and evaporated in vacuo. The residue was chromatographed on 500 g of silica gel (Merck Si60, 0.04–0.063 mm) using methylene chloride/methanol (98:2) as eluent. The product-containing fractions were evaporated in vacuo to yield 2-[4-(Phenoxybutoxy)phenyl]ethanol in the form of 9.08 g of crystals.

mp: 102° C.
Yield: 70.5% of theory.
TLC-$R_f$: 0.43 (methylenechloride:ethanol 97:3).
NMR (CDCl$_3$, 300 MHz): 2.0 [4]m, 2.8 [2] tr, J=7 Hz, 3.8 [2] q, J=7 Hz, 4.0 [4] q, J=7 Hz, 6.8–7.0 [5] m, 7.15 [2] d, J=8 Hz, 7.3 [2] tr, J=7 Hz.

EXAMPLES 10–16

Analogue of Example 9 were prepared:

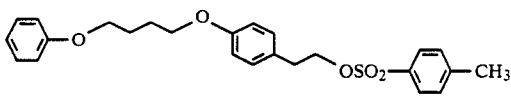

| Nr. | n | m | mp [°C.] | yield [%] | TLC-$R_f$ Solvent |
|---|---|---|---|---|---|
| 10 | 3 | para 3 | 56 | 86.9 | 0.53 CH$_2$Cl$_2$:CH$_3$OH 95:5 |
| 11 | 3 | para 2 | 77 | 80.8 | 0.75 CH$_2$Cl$_2$:CH$_3$OH 95:5 |
| 12 | 3 | meta 2 | — | 56.6 | 0.44 CH$_2$Cl$_2$:CH$_3$OH 97:3 |
| 13 | 3 | ortho 2 | — | 89.5 | 0.43 CH$_2$Cl$_2$:CH$_3$OH 97:3 |
| 14 | 4 | para 1 | 106 | 77.0 | 0.31 CHCl$_3$ |
| 15 | 4 | meta 1 | 47–48 | 96.0 | 0.32 CHCl$_3$ |
| 16 | 4 | ortho 1 | 33–34 | 74.0 | 0.51 CHCl$_3$ |

EXAMPLE 17

2-[4-(4-Phenoxybutoxy)phenyl]ethyl-1-tosylate

A suspension of 4.87 g (17 mmol) of 2-[4-(4-phenoxybutoxy)phenyl]ethanol in 15 ml of methylenechloride was stirred under nitrogen with 12 ml of dry pyridine for 30 min and then cooled to −10° C. before 3.89 g (20.4 mmol) of p-toluenesulfonyl chloride were added. The resulting mixture was stirred for 2.5 hours at 0° C. and then mixed with water and extracted twice with ethyl acetate. The combined extracts were washed with saturated aqueous sodium chloride and were then dried over sodium sulfate and evaporated in vacuo. The solid residue was chromatographed on 73 g of silica gel using methylene chloride as eluent. The product containing fractions were combined and evaporated in vacuo. After trituration with hexane, 6.28 g of the crystalline compound in the heading were obtained.

mp: 108° C.
Yield: 83.8% of theory.
TLC-$R_f$: 0.55 (methylene chloride).
NMR (CDCl$_3$, 300 MHz): 2.0 [4] m, 2.45 [3] s, 2.9 [2] tr, J=8 Hz, 3.95–4.1 [4] m, 4.2 [2] tr, J=8 Hz, 6.75 [2] d, J=8 Hz, 6.85–6.95 [3] m, 7.0 [2] d, J=8 Hz, 7.25–7.35 [4] m, 7.7 [2] d, J=8 Hz.

EXAMPLES 18–21

Using the procedure of example 17 and the compounds of examples 10 to 13 as starting material the following compounds were prepared:

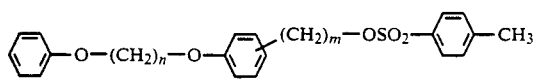

| Nr. | n | m | Yield (%) | TLC-$R_f$ |
|---|---|---|---|---|
| 18 | 3 | para 3 | 83.0 | 0.57 $CH_2Cl_2$ |
| 19 | 3 | para 2 | 98.9 | 0.57 $CH_2Cl_2$ |
| 20 | 3 | meta 2 | 92.7 | 0.55 $CH_2Cl_2$ |
| 21 | 3 | ortho 2 | 89.1 | 0.62 $CH_2Cl_2$ |

EXAMPLES 22-25

Using the procedure of example 3 and the compounds of examples 7, 14, 15 and 16 as starting materials the following compounds were prepared:

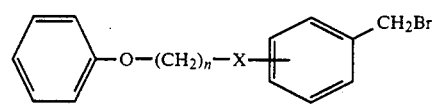

| Nr. | n | X | mp [°C.] | yield [%] | TLC-$R_f$* |
|---|---|---|---|---|---|
| 22 | 4 | O-para | 49-50 | 88.0 | 0.32 |
| 23 | 4 | O-meta | 47-49 | 73.0 | 0.33 |
| 24 | 4 | O-ortho | 68-70 | 84.0 | 0.37 |
| 25 | 5 | meta | — | 78.0 | 0.32 |

*The solvent was ethyl acetate:hexane (5:95)

EXAMPLE 26

2-[4-(4-Phenoxybutoxy)phenyl]ethyltriphenylphosphonium tosylate

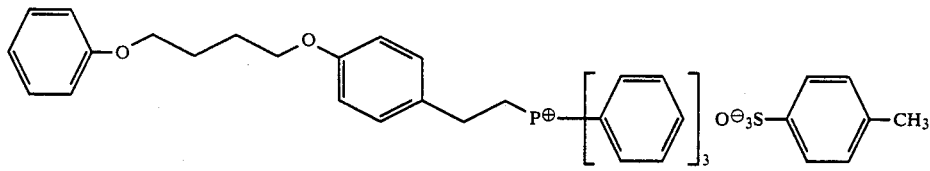

A solution of 4.85 g (11 mmol) of 2-[4-(4-phenoxybutoxy)phenyl]ethyl-1-tosylate and 2.89 g (11 mmol) of triphenylphosphine in 20 ml of acetonitrile was refluxed for 4 days. The solution was cooled and then the solvent was removed by evaporation in vacuo to yield 7.7 g of compound in the heading in the form of a solid which was sufficiently pure to be used as obtained.

Yield: 99.6% of theory

NMR (CDCl$_3$, 300 MHz): 1.95 [4] broad s, 2.3 [3] s, 2.85 -3.0 [2] m, 3.65-3.8 [2] m, 3.95 [2] broad s, 4.0 [2] broad s, 6.7 [2] d, J=8 Hz, 6.85-6.95 [3] m, 7.0 [2] d, J=8 Hz, 7.1 [2] d, J=8 Hz, 7.25 [2] tr, J=8 Hz, 7.6-7.8 [17] m.

EXAMPLE 27 TO 35

The Witting salts of the following table were prepared using the procedure of example 26 and the compounds of examples 8 and 18 to 25. Examples 27 to 30 were prepared exactly according to the process of example 26 and example 31 to 35 were prepared in refluxing benzene rather than acetonitrile and were then crystallized from benzene before use.

| Nr. | n | X | m | Y | Reflux time (h) | mp (°C.) | Yield (%) |
|---|---|---|---|---|---|---|---|
| 27 | 3 | O para | 3 | Tos | 65 | —* | 100** |
| 28 | 3 | O para | 2 | Tos | 72 | —* | 100** |
| 29 | 3 | O meta | 2 | Tos | 168 | —* | 100** |
| 30 | 3 | O ortho | 2 | Tos | 240 | —* | 100** |
| 31 | 4 | O para | 1 | Br | 24 | 55 | 65 |
| 32 | 4 | O meta | 1 | Br | 24 | 127-128 | 100 |
| 33 | 4 | O ortho | 1 | Br | 24 | 152 | 31 |
| 34 | 5 | — meta | 1 | Br | 75 | 151 | 100 |
| 35 | 5 | — para | 1 | Br | 15 | 201-202 | 88 |

*Many of these tosylates were solids, but were not recrystallized, so that a sharp melting point was not obtained.
**The residue was used without purification. If purification had been carried out, the yield would probably have been somewhat less than 100%.

EXAMPLE 27

NMR (CDCl$_3$, 300 MHz): 1.75-1.9 [4] m, 2.2 [2] quintet, J=8 Hz, 2.3 [3] s, 2.8 [2] tr, J=8 Hz, 3.4-3.55 [2] m, 4.05-4.2 [4] m, 6.8 [2] d, J=8 Hz, 6.85-6.95 [3] m, 7.0-7.05 [4] m, 7.25 [2] tr, J=8 Hz, 7.55-7.85 [17] m.

EXAMPLE 28

NMR (CDCl$_3$, 300 MHz): 2.15-2.3 [2] m, 2.3 [3] s, 2.8-3.0 [2] m, 3.65-3.8 [2] m, 4.0-4.2 [4] m, 6.7 [2] d, J=8 Hz, 6.85-6.95 [3] m, 7.05-7.15 [4] m, 7.3 [2] tr, J=8 Hz, 7.6-7.9 [17] m.

EXAMPLE 29

NMR (CDCl$_3$, 300 MHz): 2.15 [2] quintet, J=8 Hz, 2.3 [3] s, 2.9-3.05 [2] m, 3.7-3.85 [2] m, 4.1 [4] tr, J=8 Hz, 6.7 [2] d, J=8 Hz, 6.8 [1] s, 6.85-6.95 [3] m, 7.0-7.1 [3] m, 7.25 [2] tr, J=8 Hz, 7.6-7.8 [17] m.

EXAMPLE 30

NMR (CDCl$_3$, 300 MHz): 2.15 [2] quintet, J=8 Hz, 2.3 [3] s, 2.9-3.0 [2] m, 3.55-3.7 [2] m, 3.95 [2] tr, J=8 Hz, 4.1 [2] tr, J=8 Hz, 6.75-6.85 [4] m, 6.9 [1] tr, J=8 Hz, 7.0 [2] d, J=8 Hz, 7.1-7.25 [4] m, 7.55-7.8 [17] m.

EXAMPLE 36

2-(4-Methoxycarbonylbenzyl)-2-(tert.butoxycarbonyl)-cyclohexanone

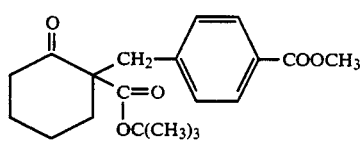

2-Tert.butoxycarbonylcyclohexanone was prepared according to the procedure of J. L. van der Barr and F. Bickelhaupt, *Tetrahedron*, 30, 2447-2553, (1974). A solution of 49.5 g (0.25 mol) of this material in 150 ml of dry dimethylformamide was stirred at 0° C. to 5° C. as a total of 7.8 g (0.25 mol) of sodium hydride (80% suspension in oil) was added in portions so that the evolution of gas did not become too vigorous. When the evolution of gas had ceased, a solution of 46.1 g (0.25 mol) of methyl 4-(chloromethyl)benzoate and 41.5 g (0.25 mol) of potassium iodide in 100 ml of dry dimethylformamide was added dropwise as stirring at 0° C. was continued. The mixture was stirred for a further 30 minutes at 0° C. and then allowed to come to room temperature. It was then poured into ice water and extracted twice with ethyl acetate. The combined extract was washed with 10% sodium thiosulfate and then with a saturated aqueous sodium chloride solution. It was dried over sodium sulfate and evaporated in vacuo. The 80 g of residue were heated in portions in a Kugelrohr still under a high vacuum to remove the volatile components. The combined non-volatile residues were crystallized from petroleum ether to yield 31.5 g of a white crystalline product.

mp: 60°–63° C.

Yield: 36% of theory.

TLC-$R_f$:0.36 (petroleum ether/ether 8:2).

NMR (CDCl$_3$, 300 MHz): 1.35 [9] s, 1.35–1.45 [1] m, 1.55–1.75 [3] m, 2.0 [1] m, 2.35 [1] dq, J=14 Hz, 3 Hz, 2.5 [2] m, 2.9 [1] d, J=14 Hz, 3.3 [1] d, J=14 Hz, 3.9 [3] s, 7.25 [2] d, J=8 Hz, 7.9 [2] d, J=8 Hz.

EXAMPLE 37

7-(4-Ethoxycarbonylphenyl)-6-tert. butoxycarbonyl heptanic acid ethyl ester

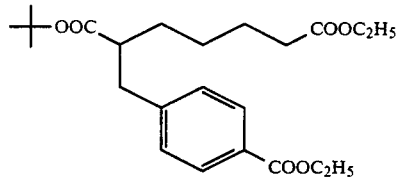

17.3 g (0.05 mol) of 2-(4-methoxycarbonylbenzyl)-2-tert.-butoxycarbonyl-cyclohexanone are heated under reflux together with 5.6 g of potassium tert. butylate in 100 ml of absolute ethanol for 1 hour. After the mixture has cooled it is diluted with water and extracted twice with ethyl acetate. The combined ethyl acetate phases are dried with sodium sulphate and concentrated by evaporation. 18 g of an oily product are thus obtained which is sufficiently pure to be used for further reactions.

Yield: 88.6% of theory.

$R_f$-value: 0.19 (petroleum: ether 8:2).

NMR (CDCl$_3$, 300 MHz): 1.25 [3] tr, J=8 Hz, 1.3 [9] s, 1.4 [3] tr, J=8 Hz, 1.3–1.5 [3] m, 1.55–1.7 [3] m, 2.25 [2] tr, J=8 Hz, 2.55–2.65 [1] m, 2.75 [1] dd, J=14 Hz, J=8 Hz, 2.95 [1] dd, J=14 Hz, J=10 Hz, 4.1 [2] q, J=8 Hz, 4.35 [2] q, J=8 Hz, 7.25 [2] J=8 Hz, 7.95 [2] d, J=8 Hz.

EXAMPLE 38

6-Tert. butoxycarbonyl-7-(4-methoxycarbonylphenyl) heptanoic acid methyl ester

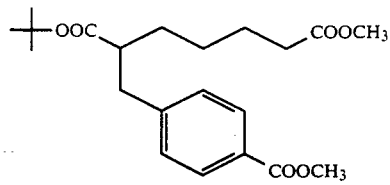

49.5 g (0.25 mol) of 2-tert. butoxycarbonylcyclohexanone are dissolved in 150 ml of absolute dimethylformamide under nitrogen and 9.0 g (0.3 mol) of an 80% sodium hydride suspension in spindle oil are added in portions at 0° to 5° C. When the evolution of hydrogen has ended a solution of 46.1 g (0.25 mol) of 4-chloromethylbenzoic acid methyl ester and 41.8 g (0.25 mol) of potassium iodide in 100 ml of absolute dimethylformamide are added dropwise at 0° C. The reaction mixture is subsequently stirred for 30 minutes at 0° C. and is then heated to room temperature and 50 of methanol are added. Then the reaction mixture is poured into ice water and extracted with 600 ml of ethylacetate. The organic phase is washed with a 10% thiosulphate solution and a saturated sodium chloride solution and is dried with sodium sulphate and concentrated by evaporation. The residue is concentrated further in portions in a Kugelrohr distillation apparatus under a high vacuum (air bath temperature: 150° C.) and then chromatographed on 1.7 kg of silica gel (Merck 5:60, 0.04–0.064 mm) using petroleum ether/ether 8/207/3 as the mobile solvent. A fraction is thus obtained which yields 35 g of a solid product after evaporation.

Yield: 37% of theory.

$R_f$-value: 0.18 (petroleumether:ether 80:20).

NMR (CDCl$_3$, 300 MHz): 1.3 [9] s, 1.3–1.75 [6] m, 2.3 [2] tr, J=8 HZ, 2.55–2.65 [1] m, 2.75 [1] dd, J=14 Hz, J=8 Hz, 2.95 [1] dd, J=14 Hz, J=10 Hz, 3.65 [3] s, 3.9 [3] s, 7.25 [2] d, J=8 Hz, 7.9 [2] d, J=8 Hz.

EXAMPLE 39

6-Carboxy-7-(4-ethoxycarbonylphenyl)heptanoic acid ethyl ester

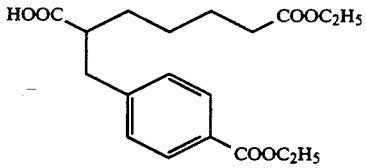

18 g (44.3 mmol) of 7-(4-ethoxycarbonylphenyl)-6-tert.-butoxycarbonylheptanoic acid ester are dissolved in 100 ml of trifluoroacetic acid and the solution is stirred vigorously for 1 hour. The trifluoroacetic acid is distilled off in vacuo and the residue is dissolved in ethyl acetate and washed with a saturated bicarbonate solution. The organic phase is dried with sodiumsulphate and concentrated by evaporation. 14.3 g of an oily product are thus obtained, which is sufficiently pure to be used for further reaction.

Yield: 92% of theory.

$R_f$-value: 0.48 (dichloromethane:methanol 95:5).

NMR (CDCl₃, 300 MHz): 1.25 [3] tr, J=8 Hz, 1.4 [3] tr, J=8 Hz, 1,3–1.75 [6] m, 2.25 [2] tr, J=8 Hz, 2.7 [1] m, 2.8 [1] dd, J=14 Hz, J=8 Hz, 3.05 [1] dd, J=14 Hz, J=10 Hz, 4.1 [2] q, J=8 Hz, 4.35 [2] q, J=8 Hz, 7.25 [2] d, J=8 Hz, 7.95 [2] dd, J=8 Hz.

EXAMPLE 40

6-Carboxy-7-(4-methoxycarbonylphenyl)heptanoic acid methyl ester

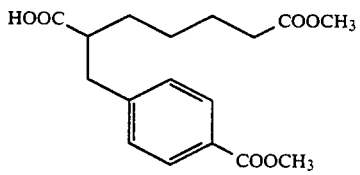

35 g (95 mmols) of 6-tert. butoxycabonyl-7-(4-methoxycarbonylphenyl)heptanoic acid methyl ester are reacted following the same procedure as Example 39. In this manner 26.7 g of a solid, m.p. 59°–60° C., are obtained which is sufficiently pure to be used for further reactions.

Yield: 89.6% of theory.

R_f-value: 0.45 (dichloromethane:methanol 95:5).

EXAMPLE 41

7-(4-Ethoxycarbonylphenyl)-6-hydroxymethylheptanoic acid ethyl ester

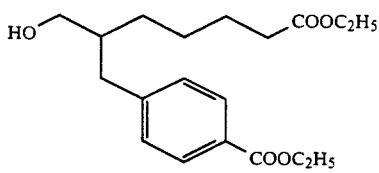

14 g (40 mmol) of 6-carboxy-7-(4-ethoxycarbonylphenyl)heptanoic acid methyl ester are dissolved under nitrogen in 60 ml of absolute tetrahydrofuran. 180 ml (50 mmol) of borane in tetrahydrofuran (content determined by titration) are added dropwise at −10° C. When the dropwise addition has ended the mixture is stirred for 2 hours while cooling with ice and is then diluted cautiously with a saturated bicarbonate solution at 0° C. and extracted twice with ethyl acetate. The combined organic phases are dried with sodium sulphate and concentrated by evaporation. 11.9 g of a yellow oily product are obtained, which is sufficiently pure to be used for further reactions.

Yield: 88.5% of theory.

R_f-value: 0.58 (dichloromethane:methanol 95:5).

NMR (CDCl₃, 300 MHz): 1.25 [3] tr, J=8 Hz, 1.4 [3] tr, J=8 Hz, 1.3–1.85 [7] m, ,3 [2] tr, J=8 Hz, 2.65 [1] dd, J=14 Hz, J=8 Hz, 2.75 [1] dd, J=14 Hz, J=8 Hz, 3.5 [2] d, J=6 Hz, 3.6 [1] tr, J=6 Hz, 4.1 [2] q, J =8 Hz, 4.35 [2] q, J=8 Hz, 7.25 [2] d, J=8 Hz, 7.95 [2] d, J=8 Hz.

EXAMPLE 42

6-Hydroxymethyl-7-(4-methoxycarbonylphenyl)heptanoic acid methyl ester

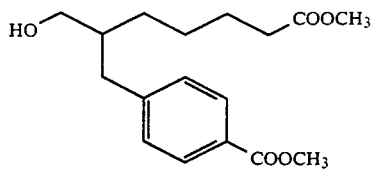

26.7 g (83 mmol) of 6-carboxy-7-(4-methoxycarbonylphenyl)heptanoic acid methyl ester are reacted following the same procedure as in Example 41, 22 g of an oily product are thus obtained which can be used without any further purification.

Yield: 88% of theory.

R_f-value: 0.55 (dichloromethane:methanol 95:5).

NMR (CDCl₃, 300 MHz): 1.3–1.85 [7] m, 2.3 [2] tr, J=8 Hz, 2.65 [1] dd, J=14 Hz, J=8 Hz, 2.75 [1] dd, J=14 Hz, J=10 Hz, 3.5 [2] d, J=8 Hz, 3.7 [3] s, 3.9 [3] s, 7.25 [2] d, J=8 Hz, 7.9 [2] d, J=8 Hz.

EXAMPLE 43

7-(4-Ethoxycarbonylphenyl)-6-formyl-heptanoic acid ethyl ester

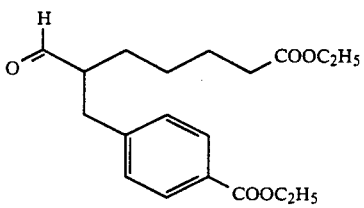

10 g (30 mmol) of 7-(4-ethoxycarbonylphenyl)-6-hydroxymethylheptanoic acid ethyl ester are dissolved in 100 ml of methylene chloride of analytical purity and methylene chloride containing 6.45 g (30 mmol) of pyridinium chlorochromate is added under cooling with tapwater. After stirring for 2 hours at room temperature 3.25 g (15 mmol) of pyridinium chlorochromate are once again added and the mixture is stirred for 1 hour. The reaction mixture (including the oily residue) is applied to a chromatographic column filled with 500 g of silica gel (Merck Si 60, 0.04– 0.063 mm) and elution is carried out under a slightly elevated pressure using methylene chloride as the mobile solvent. A fraction is thus obtained which, after being evaporated in vacuo, yields 7.7 g of an oily product.

Yield: 77% of theory.

R_f-value: 0.3 (petroleum ether:ether 60:40).

NMR (CDCl₃, 300 MHz): 1.25 [3] tr, J=8 Hz, 1.4 [3] tr, J=8 Hz, 1,4–1.75 [6] m, 2.3 [2] tr, J=8 Hz, 2.6–2.7 [1] m, 2.75 [1] dd, J=14 Hz, J=8 Hz, 3.05 [1] dd, J=14 Hz, J=8 Hz, 4.1 [2] q, J=8 Hz, 4.35 [2] q, J =8 Hz, 7.2 [2] d, J=8 Hz, 7.95 [2] d, J=8 Hz, 9.65 [1] d, J=3 Hz.

EXAMPLE 44

6-Formyl-7-(4-methoxycarbonylphenyl)heptanoic acid methyl ester

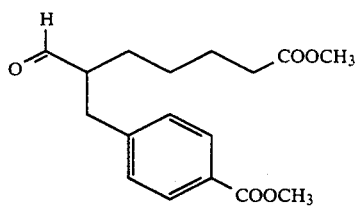

20 g (64.9 mmol) of 6-hydroxymethyl-7-(4-methoxycarbonylphenyl)heptanoic acid methyl ester are oxidized and chromatographed following the same procedure as in Example 43. 8.4 g of an oily product are thus obtained.

Yield: 42.3% of theory.

$R_f$-value: 0.12 (hexane:ether 70:30).

NMR (CDCl$_3$, 250 MHz): 1.35–1.8 [6] m, 2.3 [2] tr, J=8 Hz, 2.6–2.7 [1] m, 2.75 [1] dd, J=14 Hz, J=8 Hz, 3.05 [1] dd, J=14 Hz, J=8 Hz, 3.65 [3] s, 3.9 [3] s, 7.25 [d] 2, J=8 Hz, 7.95 [2] d, J=8 Hz, 9.65 [1] d, J=3 Hz.

EXAMPLE 45

6-(4-Ethoxycarbonylbenzyl)-7-(E), 9(E), 11(Z), 14(Z)-eicosatetraenoic acid ethyl ester

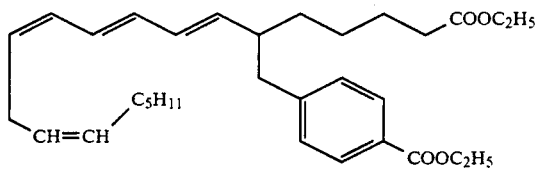

0.19 g (0.6 mmol) of 2(E), 4(Z), 7(Z)-tridecatrienylphosphonic acid diethyl ester (J. C. Buck, F. Ellis, P. North, *Tetrahedron Letters*, 4161–4162, (1982)) are dissolved under nitrogen in 2 ml of absolute tetrahydrofuran. Then at −70° C. 0.31 ml (0.5 mmol) of n-butyllithium in hexane (content titrated) are added dropwise. After stirring for 30 mins. at −70° C. 0.9 g of absolute 1,3-dimethyltetrahydropyrimidin-2-one (DMPU) are added dropwise, after which 0.17 g (0.5 mmol) of 7-(4-ethoxycarbonylphenyl)-6-formylheptanoic acid ethyl ester in 1 ml of absolute tetrahydrofuran are added dropwise at −70° C. The reaction solution is subsequently stirred at −70° C. for 15 minutes and is then heated slowly to room temperature. It is then diluted with a saturated sodium chloride solution and extracted with ethyl acetate. The organic phase is dried with sodium sulphate and concentrated by evaporation in vacuo. The residue is subjected to flash chromatography on 10 g of silica gal (Merck Si 60, 0.04–0.063 mm) using hexane/ether 80/20 as the mobile solvent. A fraction is thus obtained which after evaporation yields 0.13 g of an oily product.

Yield: 52% of theory.

$R_f$-value: 0.4 (hexane:ether 80:20).

HPLC: Retention time: 13.07 minutes, Lichrosorb RP 18 7 μm) 25×4 mm, acetonitrile:water 80:20, 4.0 ml/min. 280 nm NMR (CDCl$_3$, 200 MHz): 0.9 [3] tr, J=8 Hz, 1.25 [3] tr, J=8 Hz, 1.4 [3] tr, J=8 Hz, 1.2–1.45 [10] m, 1.5–1.65 [2] m, 2.0 [2] q, J=8 Hz, 2.25 [2] tr, J=8 Hz, 2.25–2.4 [1] m, 2.6–2.8 [2] m, 2.9 [2] tr, J=8 Hz, 4.1 [2] q, J=8 Hz, 4.35 [2] q, J=8 Hz, 5.26–5.46 [3] m, 5.46 [1] dd, J=14.8 Hz, J=8.9 Hz, 5.95 [1] dd, J=14.9 Hz, J =10.4 Hz, 5.98 [1] dd, J=10.8 Hz, J=10.8 Hz, 6.13 [1] dd, J =14.6 Hz, J=10.5 Hz, 6.36 [1] dd, J=14.5 Hz, J=11.2 Hz, 7.2 [2] d, J=8 Hz, 7.95 [d, J=8 Hz.

EXAMPLE 46

6-(4-Carboxybenzyl)-7-(E), 9(E), 11(Z), 14(Z)-eicosatetraenoic acid

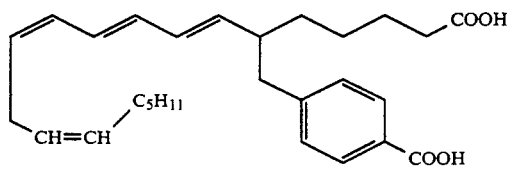

50 mg (0.1 mmol) of 6-(4-ethoxycarbonylbenzyl)7(E), 9(E), 11(Z), 14(Z)-eicosatetraenoic acid ethyl ester are dissolved in 1 ml of methanol and the solution is added to a mixture of 10 ml of methanol and 1 ml of 45% sodium hydroxide solution and the mixture is stirred at room temperature. Ether is then added in such a quantity that a clear solution is formed. The reaction solution is left to stand for 4 hours at room temperature and is then diluted with ice water and brought to pH=6 with a sodium citrate buffer (3.5 g of trisodium citrate-5,5-hydrate dissolved in 20 ml of 1 n hydrochloric acid). The cloudy aqueous solution is extracted twice with methylene chloride and the combined organic phases are dried with sodium sulphate and concentrated by evaporation. 32.6 mg of a solid residue are thus obtained as the product.

Yield: 88% of theory, $R_f$-value: 0.56 (dichloromethane:methanol 95:5),

HPLC:Retention time:12.06 minutes, Lichrosorb RP-18 (7 μm) 25×4 mm, acetonitrile:water:glacial acetic acid 70:30:0.1, adjusted to pH=5.6 with concentrated NH$_3$, 1.0 ml/min., 280 nm.

EXAMPLE 47

2-(4-Methoxycarbonylphenylthio)-2-tert.butoxycarbonylcyclohexanone

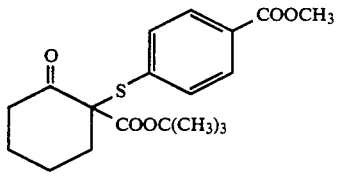

A solution 10.8 g (53.2 mmol) of 4-methoxycarbonylphenylsulphenic acid chloride in 20 ml of methylene chloride (analytically pure) is added dropwise to a solution of 11.4 g (57 mmol) of 2-tert.butoxycarbonylcyclohexanone and 7.5 g (75 mmol) of triethylamine in 150 ml of methylene chloride. When the dropwise addition has ended the mixture is subsequently stirred for 15 mins. and is then diluted with methylene chloride and the organic phase is washed with 2N sulphuric acid and a saturated bicarbonate solution, dried with sodium sulphate and concentrated by evaporation. 20.5 g of a crude product are thus obtained, which is chromatographed on 2 kg of silica gel (Merck Si 60, 0.04–0.063 nm) using petroleum ether/ether 8:20 as the mobile solvent. A fraction is thus obtained which, after being concentrated by evaporation, yields 11 g of a solid product.

Yield: 52.4% of theory.

R$_f$-value: 0.24 (petroleum ether/ether 80:20).

NMR (CDCl$_3$, 300 MHz): 1.4 [9] s, 1.5–1.9 [4] m, 1.95–2.05 [1] m, 2.4–2.55 [2] m, 2.65 [1] d tr, J=14 Hz, J=3 Hz, 3.9 [3] s, 7.55 [2] d, J=8 Hz, 7.95 [2] d, J=8 Hz.

EXAMPLE 48

6-(Methoxycarbonylphenylthio)-6-tert.butyloxycarbonylhexanoic acid methyl ester

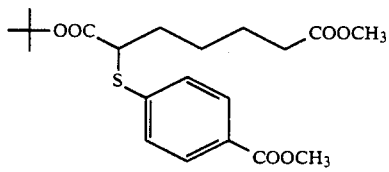

1 g (30.2 mmol) of 2-(4-methoxycarbonylphenylthio)2-tert.butoxycarbonylcyclohexanone is dissolved, together with 0.37 g (3.3 mmol) of potassium tert. butylate, in 100 ml of methanol of reagent purity and the solutions is left to stand for 2 hours at room temperature. It is then diluted with 500 ml of ethyl acetate and the organic phase is washed with water and a saturated sodium chloride solution, dried with sodium sulphate and concentrated by evaporation. After drying in a high vacuum 11.3 g of an oily product are obtained, which is sufficiently pure to be used for further reactions.

Yield: 94.2% of theory.

R$_f$-value: 0.22 (petroleum ether:ether 80:20).

NMR (CDCl$_3$, 300 MHz): 1.3 [9] s, 1.3–1.55 [2] m, 1.6 [2] quintet, J=8 Hz, 1.6–1.75 [1] m, 1.8–1.95 [1] m, 2.25 [2] tr, J=8 Hz, 3.6 [3] s, 3.65 [1] dd, J=8 Hz, J=7 Hz, 3.85 [3] s, 7.5 [2] d, J=8 Hz, 7.85 [2] d, J=8 Hz.

EXAMPLE 49

6-Carboxy-6-(4-methoxycarbonylphenylthio)hexanoic acid methyl ester

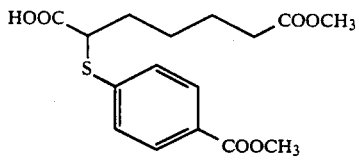

11.3 g (28.5 mmol) of 6-(4-methoxycarbonylphenylthio)-6-tert. butoxycarbonyl-hexanoic acid methylester are dissolved in 75 ml of trifluoroacetic acid and the solution is stirred vigorously for 20 minutes at room temperature. The trifluoroacetic acid is then evaporated in vacuo, the residue is dissolved in ethyl acetate and washed 3 times with water. The organic phase is dried with sodium sulphate and concentrated by evaporation. After drying under a high vacuum 9.7 g of an oily product are obtained, which is sufficiently pure to be used for further reactions.

Yield: 10% of theory.

R$_f$-value: 0.45 (dichloromethane:methanol 95:5).

NMR (CDCl$_3$, 300 MHz): 1.4–1.6 [2] m, 1.65 [2] quintet, J=8 Hz, 1.75–1.9 [1] m, 1.9–2.05 [1] m, 2.35 [2] tr, J=8 Hz, 3.65 [3] s, 3.8 [1] tr, J=8 Hz, 3.9 [3] s, 7.45 [2] d, J=8 Hz, 7.95 [2] d, J=8 Hz.

EXAMPLE 50

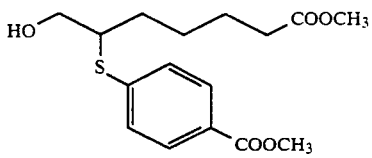

7-Hydroxy-6-(4-methoxycarbonylphenylthio)-heptanoic acid methyl ester 200 ml (67 mmol) of borane in tetrahydrofuran (content determined) are added dropwise under nitrogen at −10° C. to a solution of 9.6 g (28.2 mmol) of 6-carboxy-6-(4-methoxycarbonylphenylthio)hexanoic acid methyl ester in 40 ml of absolute tetrahydrofuran. When the dropwise addition has ended the mixture is stirred for 3 hours at 0° C. Then it is diluted catiously with saturated bicarbonate solution at 0° C., extracted twice with ethyl acetate and the combined organic phases are dried with sodium sulphate and concentrated by evaporation. 10.65 g of a crude product are thus obtained, which is chromatographed on 1 kg of silica gel (Merck Si 60, 0.04–0.063 nm) using methylene chloride/methanol 99.5/0.5 to 98/2) as the mobile solvent. A fraction is thus obtained which yields 3.2 g of an oily product after concentration by evaporation.

Yield: 34.8% of theory.

R$_f$-value: 0.73 (methylene chloride/methanol 95:5).

NMR (CDCl$_3$, 300 MHz): 1.45–1.85 [6] m, 2.3 ([2] tr, J=8 Hz, 3.35 [1] quintet, J=8 Hz, 3.6–3.75 [2] m, 3.65 [3] s, 3.9 [3] s, 7.4 [2] d, J=8 Hz, 7.95 [2] d, J=8 Hz.

EXAMPLE 51

6-Formyl-6-(4-methoxycarbonylphenylthio)hexanoic acid methyl ester

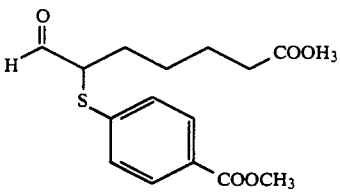

0.54 g (2.5 mmol) of pyridinium chlorochromate are added to a solution of 0.65 g (2 mmol) of 7-hydroxy-6-(4-methoxycarbonylphenylthio)heptanoic acid methyl ester in 5 ml of methylene chloride. The reaction mixture is stirred for 1 hour at room temperature. Then the reaction mixture (including the black, oily residue) is poured onto a column filled with 30 g of silica gel (Merck Si 60, 0.04–0.063 mm) and elution is carried out using methylene chloride as the mobile solvent. A fraction is thus obtained which after evaporation yields 0.32 g of an oily product.

Yield: 50% of theory.

R$_f$-value: 0.33 (methylene chloride:methanol 99:1).

NMR (CDCl$_3$, 200 MHz): 1.4–2.0 [6] m, 2.35 [2] tr, J=8 Hz, 3.6–3.7 [1] m, 3.65 [3] s, 3.9 [3] s, 7.4 [2] d, J=8 Hz, 7.95 [2] d, J=8 Hz, 9.35 [1] d, J=7 Hz.

EXAMPLE 52

10-Formyl-6-(4-methoxycarbonylphenylthio)-7(E), 9(E)-decadienoic acid methyl ester

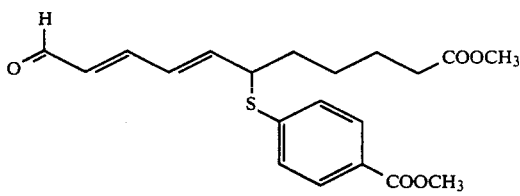

1.4 ml (2 mmol) of n-butyllithium in hexane (content titrated) are added dropwise to a solution of 1.16 g (3 mmol) of freshly distilled 1-(tri-n-butylstannyl)-4-ethoxybutadiene (R. H. Wollenberg, *Tetrahedron Letters*, 717–720, (1978) in 16 ml of absolute tetrahydrofuran under nitrogen at −70° C. The temperature of the reaction solution is allowed to rise to −40° C. over a period of 15 minutes, the solution is then cooled again to −70° C. and a solution of 0.66 g (2 mmol) of 6-formyl-6-(4-methoxycarbonylphenylthio)hexanoic acid methyl ester in 8 ml of absolute tetrahydrofuran is added dropwise at this temperature. The mixture is stirred for 1 hour at −70° C., the cold reaction solution is poured into a saturated bicarbonate solution and the mixture is extracted with ethyl acetate. The organic phase is dried with sodium sulphate and concentrated by evaporation. The oily residue is dissolved in 30 ml of a tetrahydrofuran/water 95:5 mixture and 0.2 g of p-toluenesulphonic acid hydrate is added. After stirring the mixture for 20 hours at room temperature 0.2 g of p-toluenesulphonic acid hydrate and 1 ml water are again added and the mixture is stirred for a further 3 hours. Then a further 0.2 g of p-toluenesulphonic acid hydrate is added and the mixture is stirred at room temperature for 4 hours. The mixture is worked up by diluting it with ethylacetate and extracting the diluted mixture twice with 2 n sodium hydroxide solution. The organic phase is dried with sodium sulphate and concentrated by evaporation. The residue is chromatographed with hexane/ether (80/20 to 60/40) on 80 g of silica gel (Merck Si 60, 0.04–0.063 nm). A fraction is thus obtained which, after being concentrated by evaporation, yields 100 mg of an oily product.

Yield: 13.3% of theory.

$R_f$-value: 0.13 (hexane:ether 60:40).

Retention time: 10.4 minutes, Lichrosorb Si 50 (5 μm) 25×4 mm, n-hexane/ether 60/40, 280 nm.

NMR (CDCl$_3$, 200 MHz): 1.4–1.9 [6] m, 2.35 [2] tr, J=8 Hz, 3.65 [3] s, 3.8 [1] q, J=8 Hz, 3.9 [3] s, 6.05 [1] dd, J=15 Hz, J=8 Hz, 6.0–6.25 [2] m, 7.0 [1] dd, J=15 Hz, J=10 Hz, 9.5 [1] d, J=8 Hz.

EXAMPLE 53

6-(4-Methoxycarbonylphenylthio)-7(E), 9(E), 11(Z), 14(Z)-eicosatetraenoic acid methyl ester

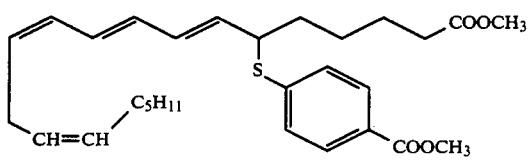

0.3 ml (0.43 mmol) of n-butyllithium in hexane (content titrated) are added dropwise to a solution of 0.36 g (0.65 mmol) of 3(Z)-nonenyltriphenyl-phosphonium tosylate (I. Ernest, A. J. Main, R. Menasse, *Tetrahedron Letters*, 23, 167–170 (1982)) in 3 ml of absolute tetrahydrofuran at −30° C. under nitrogen. The reaction solution is subsequently stirred for 10 minutes at −20° C. and is then cooled to −70° C. At −70° C. 0.38 ml of 1,3-dimethyltetrahydropyrimidin-2-one (DMPU) are first added dropwise, followed by a solution of 100 mg (0.266 mmol) of 10-formyl-6-(4-methoxycarbonylphenylthio)-7(E), 9(E)-decadienoic acid methylester in 1 ml of absolute tetrahydrofuran. The reaction solution is heated slowly to roomtemperature, diluted with a saturated bicarbonate solution and extracted with ethylacetate. The organic phase is washed with a saturated sodium chloride solution, dried with sodium sulphate and concentrated by evaporation. The residue is chromatographed with hexane/ether 80/20 on 20 g of silica gel (Merck Si 60, 0.04–0.063 mm). A fraction is thus obtained which, after evaporation, yields 63 mg of an oily product.

Yield: 48.9% of theory.

$R_f$-value: 0.59 (hexane:ether 60:40).

HPLC: Retention time 14.2 minutes, Lichrosorb RP 18 (7 μm) 25×4 mm, acetonitrile/water 80/20, 2.0 ml/min., 280 nm.

NMR (CDCl$_3$, 300 MHz): 0.9 [3] tr, J=8 Hz, 1.2–1.4 [8] m, 1.45 [2] m, 1.6–1.85 [4] m, 2.05 [2] q, J=8 Hz, 2.3 [2] tr, J=8 Hz, 2.9 [2] tr, J=8 Hz, 3.65 [3] s, 3.8 [1] d tr, J=8 Hz, J=9 Hz, 3.9 [3] s, 5.25–5.5 [3] m, 5.55 [1] d, J=14 Hz, J=9 Hz, 5.97 [1]1] tr, J=11 Hz, 6.03–6.17 [2] m, 6.41 [1] dd, J=13.8 Hz, J=10.9 Hz, 7.35 [2] d, J=8 Hz, 7.90 [2] d, J=8 Hz,

EXAMPLE 54

6-(4-Carboxyphenylthio)-7(E), 9(E), 11(Z), 14(Z)-eicosane-tetraenoic acid

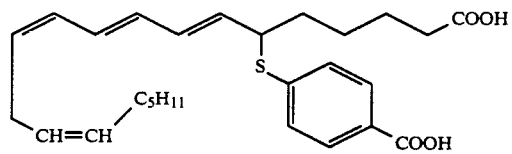

33 mg of 6-(4-methoxycarbonylphenylthio)-7(E), 9(E), 11(Z), 14(Z)-eicosatetraenoic acid methylester are dissolved in 1 ml of methanol and the solution is added to a mixture of 8 ml of methanol and 1 ml of 45% sodium hydroxide solution. The clear solution is left to stand for 4 hours at room temperature, is then diluted with ice water and brought to a pH of 6 with a citrate buffer (7 g of trisodium citrate-5,5-hydrate dissolved in 20 ml of 1 n hydrochloric acid). The cloudy aqueous solution is extracted twice with methylene chloride and the combined organic phases are dried with sodium sulphate and concentrated by evaporation, 25 mg of a solid product are thus obtained.

Yield: 80% of theory.

$R_f$-value: 0.1 (methylene chloride:methanol 95:5).

HPLC: Retention time 11.99 mins., Lichrosorb RP 18 (8 μm) 25×4 mm, acetonitrile/water/glacial acetic acid 70/30/0.1, adjusted to pH 5.6 with concentrated NH$_3$, 1.0 ml/min, 280 nm.

EXAMPLE 55

3-(4-Methoxycarbonylphenyl)propanol

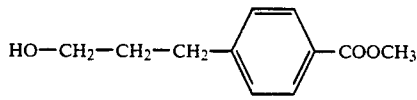

154.7 g (1.3 mol) of thionyl chloride are added dropwise to 1 l of methanol at −20° C. and 100 g (0.556 mol) of 3-(4-carboxyphenyl)propanol (J. Hora, Rec. Trav. Chim. Pays-Bas, 98, 45–49 (1976)) are then added at 0° C. The reaction solution is stirred overnight at room temperature and is then concentrated by evaporation in vacuo, diluted with ethyl acetate and washed twice with 2 n sodium hydroxide solution. The organic phase is dried with magnesium sulphate and concentrated by evaporation. 95.2 g of an oily product are thus obtained, which is sufficiently pure for use in further reactions.

Yield: 88.3% of theory.

$R_f$-value: 0.12 (toluene:ethylacetate 9:1).

NMR (CDCl$_3$, 300 MHz): 1.9 [2] quintet, J = 8 Hz, 2.3 [2] tr, J = 8 Hz, 3.65 [ ] tr, J = 8 Hz, 3.9 [3] s, 7.25 [d, J = 8 Hz, 7.95 [2] d, J = 8 Hz.

EXAMPLE 56

3-(4-Methoxycarbonylphenyl)propanal

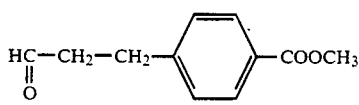

24.1 ml (0.34 mol) of absolute dimethylsulphoxide purity in 60 ml of methylene chloride of reagent purity are added dropwise to a solution of 14.5 ml (0.17 mol) of oxalylchloride in 285 ml of methylene chloride. The reaction solution is subsequently stirred for 15 mins. at −60° C. and then a solution of 22 g (0.113 mol) of 3-(4-methoxy-carbonylphenyl)-propanol in 60 ml of methylene chloride is added dropwise at −60° C. The reaction solution is subsequently stirred for 15 minutes at −60° C. and then 79 ml (0.56 mol) of triethylamine are added dropwise at −60° C. The reaction mixture is allowed to reach room temperature, washed with water, dried with sodium sulphate and concentrated by evaporation. The residue is chromatographed with toluene/ethylacetate 9/1 on 800 g of silica gel (Merck Si 60, 0.04–0.063 mm). A fraction is thus obtained which, after being concentrated by evaporation, yields 20.31 g of an oily product.

Yield: 93.5% of theory.

$R_f$-value: 0.43 (toluene/ethylacetate 9:1).

NMR (CDCl$_3$, 250 MHz): 2.3 [2] tr, J = 8 Hz, J = 0.5 Hz, 3.0 [2] tr, J = 8 Hz, 3.9 [3] s, 7.3 [2] d, J = 8 Hz, 8.0 [2] d, J = 8 Hz, 9.8 [1] tr, J = 0.5 Hz.

EXAMPLE 57

3-(4-Methoxycarbonylphenyl)-1-trimethylsilyloxy-1-propene

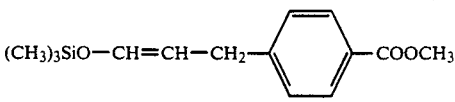

9.61 g (50 mmol) 3-(4-Methoxycarbonylphenyl)-propanal are dissolved, together with 8.3 ml (68 mmol) of trimethylchlorosilane and 18.1 ml (0.13 mol) of triethylamine, in 15 ml of absolute dimethyl formamide and the solution is heated under reflux for 2 hours under nitrogen. After cooling, the reaction mixture is diluted with a saturated bicarbonate solution and extracted with petroleum ether. The organic phase is washed 3 times with a saturated bicarbonate solution, dried with sodium sulphate and concentrated by evaporation. The residue is distilled under a high vacuum (distillation apparatus silylated). 11.06 g of a pale yellow, oily product are thus obtained in the form of a mixture of the cis- and trans-isomers.

Boiling point: 150° C. at 0.5 mm.

Yield: 83.7% of theory.

NMR (CDCl$_3$, 300 MHZ): 3.15 [0.84] d, J = 8 Hz, trans-Isomer, 3.35 [1.16] d, J = 8 Hz, cis-Isomer, 3.75 [3] s, 4.05 [0.58] q, J = 8 Hz, cis-Isomer, 5.0 [0.42] d tr, J = 14 Hz, J = 8 Hz, trans-Isomer, 6.2 [2] m, 7.1 [2] m, 7.8 [2] m.

EXAMPLE 58

6-Formyl-7-(4-methoxycarbonylphenyl)-5-thiaheptanoic acid methyl ester

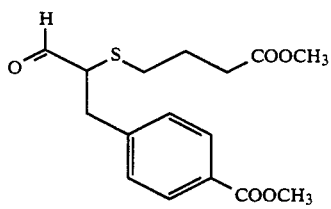

A solution of 1.7 g (12.5 mmol) of freshly distilled sulphuryl chloride in 10 ml of methylene chloride is added dropwise to a solution of 3.33 g (12.5 mmol) of 4,4'-dithiobutyric acid dimethyl ester in 10 ml of methylene chloride under nitrogen at −70° C. The reaction solution is stirred for 20 minutes at 0° C., cooled again to −70° C. and a solution of 6.61 g (25 mmol) of 3-(4-methoxycarbonylphenyl)-1-trimethylsilyloxy-1-propene in 20 ml of methylene chloride is added dropwise. The reaction solution is subsequently stirred for 1 hour at −70° C. is then poured into 300 ml of a saturated bicarbonate solution, shaken vigorously and extracted with ethyl acetate. The organic phase is washed with a saturated sodium chloride solution, dried with sodium sulphate and concentrated by evaporation. 8.2 g of an oily residue are thus obtained, which residue is chromatographed on 200 g of silica gel (Merck Si 60, 0.04–0.063 nm) with n-hexane/ether 60/40 as the mobile solvent. A fraction is thus obtained which, after being concentrated by evaporation, yields 3.3 g of an oily product.

Yield: 40.6% of theory.

$R_f$-value: 0.52 (toluene:ethyl acetate 80:20).

NMR (CDCl₃, 300 MHz): 1.8–1.95 [2] m, 2.35 [2] tr, J=8 Hz, 2.45 [2] tr, J=8 Hz, 2.95 [1] dd, J=14 Hz, J=6 Hz, 3.2 [1] dd, J=14 Hz, J=8 Hz, 3.45 [1] ddd, J=8 Hz, J=6 Hz, J=3 Hz, 3.65 [3] s, 3.9 [3] s, 7.3 [2] d, J=8 Hz, 8.0 [2] d, J=8 Hz, 9.3 [1] d, J=3 Hz.

EXAMPLE 59

10-Formyl-6-(4-methoxycarbonylbenzyl)-5-thia-7(E), 9(E)-decadienoic acid methyl ester

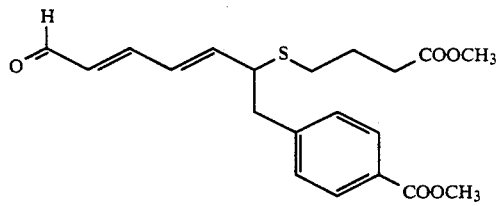

1.1 ml (1.6 mmol) of n-butyllithium in hexane (content titrated) is added dropwise to a solution of 0.94 g (2.4 mmol) of freshly distilled 1-(tri-n-butylstannyl-4-ethoxybutadiene (R. H. Wollenberg, Tetrahedron Letters, 717–720, (1978)) in 13 ml of absolute tetrahydrofuran at −70° C. under nitrogen. The temperature of the reaction solution is allowed to rise to −40° C. over a period of 15 minutes the solution is cooled again to −70° C. and a solution of 0.53 g of (1.6 mmol) of 6-formyl-7-(4-methoxycarbonylphenyl)-5-thiaheptanoic acid methyl ester is added dropwise thereto. The reaction solution is subsequently stirred for 1 hour at −70° C. and is then poured into a saturated bicarbonate solution and extracted 3 times with ethylacetate. The combined organic phases are dried with sodium sulphate and concentrated by evaporation. The residue is dissolved in 30 ml of tetrahydrofuran 1.6 ml of water and 0.2 g of p-toluene-sulphonic acid hydrate are added and the mixture is stirred at roomtemperature for 1.5 hours. It is then diluted with ethylacetate, extracted twice with 2 n sodium hydroxide solution, and the combined organic phases are dried with sodium sulphate and concentrated by evaporation. The residue is chromatographed on 100 g of silica gel (Merck Si 60, 0.04–0.63 mm) using n-hexane/ether/triethylamine 50/50/0.5 as the mobile solvent. A fraction is thus obtained which, after being concentrated by evaporation, yields 0.11 g of the product.

Yield: 18.1% of theory.

R_f-value: 0.24 (n-hexane/ether 1:1).

NMR (CDCl₃, 300 MHz): 1.75–1.95 [2] m, 2.3–2.55 [4] m, 2.9–3.1 [2] m, 3.55 [1] q, J=8 Hz, 3.65 [3] s, 3.9 [3] s, 6.02 [1] dd, J=14 Hz, J=8 Hz, 6.08 [1] dd, J=14 Hz, J=8 Hz, 6.16 [1] dd, J=14 Hz, J=10 Hz, 7.05 [1] dd, J=14 Hz, J=8 Hz, 7.25 [2] d, J=8 Hz, 7.95 [2] d, J=8 Hz, 9.55 [1] d, J=8 Hz.

EXAMPLE 60

6-(4-Methoxycarbonylbenzyl)-5-thia-7(E), 9(E), 11(Z) 14(Z)-eicosatetraenoic acid methyl ester

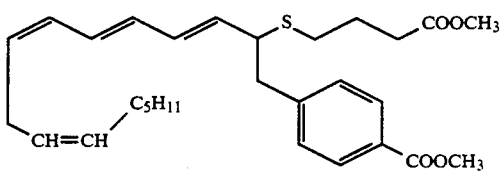

0.17 ml (0.266 mmol) of n-butyllithium in hexane (content titrated) are added dropwise to a solution of 0.18 g (0.32 mmol) of 3(Z)-nonenyltriphenylphosphonium tosylate (I. Ernest, A. J. Main, P. Menasse, Tetrahedron Letters, 23, 167–170 (1982) in 3 ml of absolute tetrahydrofuran at −30° C. The reaction solution is subsequently stirred for 10 minutes at −30° C., is then cooled to −70° C. and 0.5 ml of absolute 1,3-dimethyl-tetrahydropyrimidin-2-one (DMPU) is added dropwise at this temperature. Then a solution of 0.1 g (0.266 mmol) of 10-formyl-6-(4-methoxycarbonylbenzyl)-5-thia-7(E), 9(E)-decadienoic acid methyl ester in 0.6 ml of absolute tetrahydrofuran is added dropwise at −70° C. After stirring the mixture for 1 hour at −70° C. 0.2 ml of methanol is added, the reaction solution is allowed to warm to room temperature, slowly diluted with water and extracted with ethylacetate. The organic phase is washed with water and a saturated sodium chloride solution, dried with sodium sulphate and concentrated by evaporation. The residue is chromatographed on 22 g of silica gel (Merck Si 60, 0.04–0.063 mm) using n-hexane/ether 80/20 as the mobile solvent. A fraction is thus obtained which, after being concentrated by evaporation, yields 7.4 mg of the product.

Yield: 5.7% of theory.

R_f-value: 0.29 (hexane:ether 70:30).

NMR (CDCl₃, 300 MHz): 0.9 [3] tr, J=8 Hz, 1.2–1.4 [6] m, 1.8–1.95 [2] m, 2.05 [2] q, J=8 Hz, 2.3–2.55 [4] m, 2.85–3.05 [4] m, 3.5 [1] d, tr, J=9 Hz, J=8 Hz, 3.65 [3] s, 3.9 [3] s, 5.27–5.45 [3] m, 5.48 [1] dd, J=14.7 Hz, J=9.4 Hz, 5.94–6.04 [2] m, 6.15 [1] dd, J=14.6 Hz, J=10.7 Hz, 6.43 [1] dd, J=14.5 Hz, J=11.2 Hz, 7.25 [2] d, J=8 Hz, 7.95 [2] d, J=8 Hz.

EXAMPLE 61

6-(Carboxybenzyl)-5-thia-7(E), 9(E), 11(Z), 14(Z)-eicosatetraenoic acid

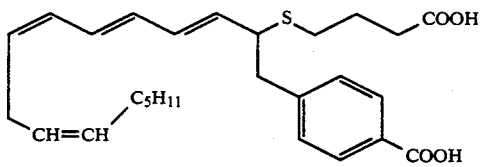

7.4 mg of 6-(4-methoxycarbonylbenzyl)-5-thia-7(E), 9(E), 11(Z), 14(Z)-eicosatetraenoic acid methyl ester are saponified following the same procedure as in Example 54, 5.6 mg of the product are thus obtained.

Yield: 81.8% of theory.

R_f-value: 0.6 (methylene chloride:methanol 9:1).

HPLC: Retention time 10.5 minutes, Lichrosorb RP 18 (7 μm), 25×4 mm, acetonitrile/water/glacial acetic acid 70/30/0.1, adjusted to pH 5.6 with concentrated NH₃, 1.0 ml/min., 280 nm.

EXAMPLE 62

6-Carboxy-6-(4-methoxycarbonylphenyl)hexanoic acid methyl ester

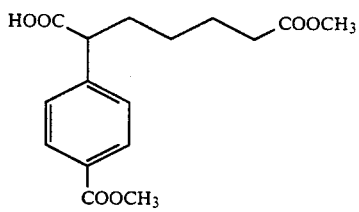

15.4 ml (0,11 mol) diisopropylamine are dissolved in 200 ml of absolute tetrahydrofuran under nitrogen and 71.5 ml (0.11 mol) of n-butyllithium in hexane (content titrated) are added dropwise at 0° C. Then a solution of 9.29 g of 4-methoxycarbonylphenylacetic acid in 20 ml of absolute tetrahydrofuran is added dropwise at 0° C., then 15 ml of absolute 1,3-dimethyltetrahydropyrimidin-2-one (DMPU) are added dropwise at 0° C. and the reaction solution is stirred for 1 hour at this temperature. Then a solution of 13.37 g (67.9 mmol) of 1-(4-bromobutyl)-4-ethyl-2,6,7-trioxabicyclo[2.2.2]octane (prepared analogously as described by E. J. Corey, N. Raju, Tetrahedron Letters, 24, 5571-5574 (1983)) in 10 ml of absolute 1,3-dimethyl-tetrahydropyrimidine (DMPU) is added dropwise at 0° C. and the reaction solution is subsequently stirred at 0° C. for 1.5 hours. It is then diluted with 2 n sulphuric acid and extracted 3 times with ethyl acetate. The combined organic phases are dried with sodium sulphate and concentrated by evaporation, the residue is dissolved in 200 ml of methanol and 11.8 ml (95.8 mmol) of 1,5-diazabicyclo(4,3,0)non-5-ene (DBN) are added. The mixture is left to stand at room temperature for 18 hours, the methanol is then substantially evaporated in vacuo and the residue is dissolved in ethyl acetate. The ethyl acetate solution is washed once with 2 n sulphuric acid and 3 times with a saturated sodium chloride solution, dried with sodium sulphate and concentrated by evaporation. The residue is chromatographed with methylene chloride/methanol 95/5 and kg of silica gel (Merck Si 60, 0.04-0.63 mm). A fraction is thus obtained which after being concentrated by evaporation, yields 6.8 g of an oily product.

Yield: 46% of theory.

$R_f$ value: 0.63 (methylene chloride:methanol 9:1).

NMR (CDCl$_3$, 300 MHz): 1.2-1.4 [2] m, 1.55-1.7 [2] quintet, J=8 Hz, 1.7-1.85 [1] m, 2.0-2.15 [1] m, 2.3 [2] tr, J=8 Hz, 3.6 [1] tr, J=8 Hz, 3.65 [3] s, 3.9 [3] s, 7.4 [2] d, J=8 Hz, 8.0 [2] d, J=8 Hz.

EXAMPLE 63

7-Hydroxy-6-(methoxycarbonylphenyl)heptanoic acid methyl ester

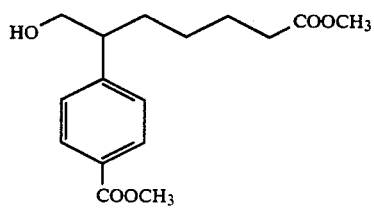

73.5 ml (22 mmol) of borane in tetrahydrofuran (content determined) are added dropwise at −10° C., under nitrogen to a solution of 6.8 g (22 mmol) of 6-carboxy-6-(4-methoxycarbonylphenyl)hexanoic acid methyl ester in 100 ml of absolute tetrahydrofuran. The reaction solution is allowed to warm to room temperature and is subsequently stirred for 2 hours. It is worked up by cooling it to 0° C. and diluting it cautiously with water. It is extracted twice with ethyl acetate and the combined organic phases are washed with a saturated bicarbonate solution and a saturated sodium chloride solution, dried with sodium sulphate and concentrated by evaporation. The residue is chromatographed with methylene chloride/methanol 99/1 to 95/5 on 600 g of silica gel (Merck Si 60, 0.04-0.063 mm). A fraction is thus obtained which after being concentrated by evaporation, yields 3.51 g of an oily product.

Yield: 54.1% of theory.

$R_f$ value: 0.65 (methylene chloride:methanol 95:5).

NMR (CDCl$_3$, 300 MHz): 1.15-1.3 [2] m, 1.5-1.7 [3] m, 1.7-1.85 [1] m, 2.25 [2] tr, J=8 Hz, 2.85 [1] quintet, J=8 Hz, 3.65 [3] s, 3.75 [2] d, J=8 Hz, 3.9 [3] s, 7.3 [2] d, J=8 Hz, 8.0 [2] d, J=8 Hz.

EXAMPLE 64

6-Formyl-6-(4-methoxycarbonylphenyl)hexanoic acid methyl ester

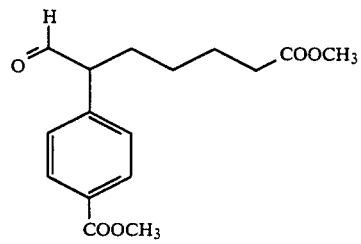

3.59 g (16.6 mmol) of pyridinium chlorochromate are added to a solution of 3.5 g (11.9 mmol) of 7-hydroxy-6-(methoxycarbonylphenyl)heptanoic acid methyl ester in 35 ml of methylene chloride of reagent purity. The reaction mixture is stirred for 1.5 hours at room temperature and then chromatographed with methylene chloride on 100 g of silica gel (silica gel Si 60, 0.04-0.063 mm). A fraction is thus obtained which, after being concentrated by evaporation, yields 2.64 g of an oily crude product. On chromatographing the crude product a second time on 150 g of silica gel (Merck Si 60, 0.04-0.063 mm) using n-hexane/ether 70/30 as the mobile solvent a fraction is obtained which, after being concentrated by evaporation, yields 1.42 g of a clean, oily product.

Yield: 40.9% of theory.

$R_f$ value: 0,16 (n-hexane:ether 60:40).

NMR (CDCl$_3$, 300 MHz): 1.2-1.4 [2] m, 1.55-1.85 [3] m, 2.05-2.2 [1] m, 2.3 [2] tr, J=8 Hz, 3.6 [1] tr d, J=8 Hz, J=0.5 Hz, 3.65 [3] s, 3.9 [3] s, 7.3 [2] d, J=8 Hz, 8.05 [2] d, J=8 Hz, 9.7 [1] d, J=0.5 Hz.

EXAMPLE 65

6-(4-Methoxycarbonylphenyl)-7(E), 9(E), 11(Z), 14(Z)-eicosatetraenoic acid methyl ester

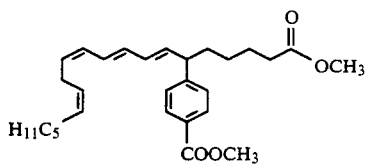

0.19 g (0.6 mmol) of 2(E), 4(Z), 7(Z)-tridecatrienyl-phosphonic acid diethyl ester (S. C. Buck, F. Ellis, P. North, Tetrahedron Letters, 4161-4162, (1982)) are dissolved in 2 ml of absolute tetrahydrofuran under nitrogen. Then 0.325 ml (0.5 mmol) of n-butyllithium in hexane (content titrated) are added dropwise at −70° C. After stirring for 30 minutes at −70° C., 0.9 ml of absolute 1,3-dimethyltetrahydropyrimidin-2-one (DMPU) are added dropwise, then 0.25 g (0.856 mmol) of 6-formyl-6-(4-methoxycarbonylphenyl)hexanoic acid methyl ester dissolved in 1 ml of absolute tetrahydrofuran are added dropwise at −70° C. The reaction mixture is allowed to reach room temperature very slowly, is diluted with a saturated bicarbonate solution and is extracted twice with ethyl acetate. The combined organic phases are washed with a saturated sodium chloride solution and concentrated by evaporation. The residue is chromatographed with n-hexane/ether 90/10 on 10 g of silica gel (Merck Si 60, 0.04-0.063 mm). A fraction is thus obtained which, after being concentrated by evaporation, yields 19 mg of an oily product. A second, more polar fraction yields, after being concentrated by evaporation, 80 mg of the aldehyde starting material.

Yield: 5% of theory.

R$_f$-value: 0.61 (n-hexane:ether 60:40).

HPLC: Retention time 7.53 minutes, Lichrosorb RP 18 (7 μm) 25×4 mm, acetonitrile: water 80:20, 4.0 ml/min., 280 nm.

NMR (CDCl$_3$, 300 MHz): 0.9 [3] tr, J=8 Hz, 1.2-1.4 [8] m, 1.65 [2] quintet, J=8 Hz, 1.75 [2] q, J=8 Hz, 2.05 [2] q, J=8 Hz, 2.3 [2] tr, J=8 Hz, 2.95 [2] tr, J=8 Hz, 3.35 [1] q, J=8 Hz, 3.65 [3] s, 3.9 [3] s, 5.28-5.47 [3] m, 5.79 [1] dd, J=14.3 Hz, J=7.8 Hz, 6.0 [1] tr, J=11 Hz, 6.05-6.23 [2] m, 6.44 [1] dd, J=13.5 Hz, J=11.5 Hz, 7.25 [2] d, J=8 Hz, 8.0 [2] d, J=8 Hz.

EXAMPLE 66

6-(4-Carboxyphenyl)-7(E), 9(E), 11(Z), 14(Z)-eicosatetraenoic acid

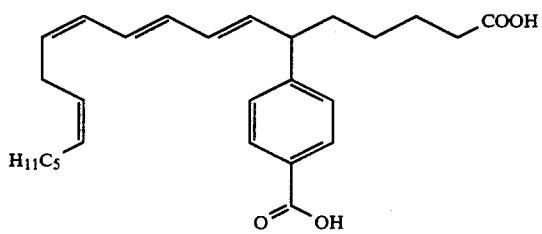

A solution of 19 mg of 6-(4-methoxycarbonyl-phenyl)7(E), 9(E), 11(Z), 14(Z)-eicosatetraenoic acid methyl ester in 1 ml of methanol is added to a solution of 0.2 ml of 45% sodium hydroxide solution in 2 ml of methanol. Such a quantity of ether (about 1 ml) is added dropwise with stirring until a clear solution is formed. This solution is left to stand for 3.5 hours at room temperature is then diluted with ice water and is brought to a pH of 3 with 2 n sulphuric acid. The cloudy aqueous phase is extracted with ethyl acetate and the ethyl acetate phase is washed with water, dried with sodium sulphate and concentrated by evaporation, 16 mg of a solid residue are thus obtained as the product.

Yield: 89.8% of theory.

R$_f$-value: 0.18 (methylene chloride:methanol 95:5).

HPLC: Retention time 12.63 minutes, Lichrosorb RP 18 (7 μm) 25×4 mm, acetonitrile:water:glacial acetic acid 70:30:1, adjusted to a pH of 5.6 with concentrated NH$_3$, 1.0 ml/min., 280 nm.

EXAMPLE 67

6-(4-Methoxycarbonylbenzyl)-9-[3-(3-phenoxypropox-y)phenyl]-7(Z)-nonenoic acid methyl ester

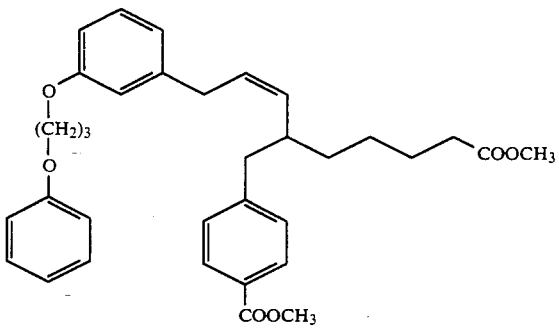

0.79 ml (1 mmol) of n-butyllithium in hexane (content titrated) are added dropwise under nitrogen at −28° C. to a solution of 0.826 g (1.2 mmol) of 2-[3-(3-phenoxy-propoxy)phenyl]ethyltriphenylphosphonium tosylate in 11 ml of absolute tetrahydrofuran. The mixture is subsequently stirred at −25° C. for 15 minutes, then cooled to −70° C. and 1.8 ml of absolute 1,3-dimethyltetrahy-dropyrimidin-2-one are added at −70° C. Then a solution of 0.31 g (1 mmol) of 6-formyl-7-(4-methoxycar-bonylphenyl) heptanoic acid methyl ester in 2 ml of absolute tetrahydrofuran is added dropwise at −70° C. After stirring for 30 mins. at −70° C. 0.5 ml of methanol is added dropwise and the reaction mixture is allwed to warm slowly to 0° C. It is then stirred for 1 hour at 0° C., diluted with ethyl acetate and washed with water and a saturated sodium chloride solution. The organic phase is dried with sodium sulphate and concentrated by evaporation. The residue is chromatographed with n-hexane/ether 75/25 on 50 g of silica gel (Merck Si 60, 0.04-0.063 mm). A fraction is thus obtained which, after evaporation yields 0.27 g of the product in the form of a pale yellow oil.

Yield: 49.6% of theory.

R$_f$-value: 0.36 (n-hexane:ether 70:30).

NMR (CDCl$_3$, 300 MHz): 1.3-1.7 [6] m, 2.2-2.3 [4] m, 2.55 [1] dd, H≡13 Hz, J=8 Hz, 2.65-2.8 [2] m, 3.0 [1] dd, J=14 Hz, J=8 Hz, 3.15 [1] dd, J=14 Hz, J=8 Hz, 3.65 [3] s, 3.9 [3] s, 4.1 [2] tr, J=8 Hz, 4.15 [2] tr, J=8 Hz, 5.2 [1] tr, J=10 Hz, 5.5 [1] d, tr, J=10 Hz, J=7 Hz, 6.45 [1] d, J=8 Hz, 6.55 [1] s, 6.7 [1] dd, J=8 Hz, J=1 Hz, 6.85-6.95 [3] m, 7.05 [1] tr, J=8 Hz, 7.2 [2] d, J=8 Hz, 7.25-7.3 [2] m, 7.9 [2] d, J=8 Hz.

EXAMPLE 68

6-(4-Carboxybenzyl)-9-[3-(3-phenoxypropoxy)phenyl]-7(Z)-nonenoic acid

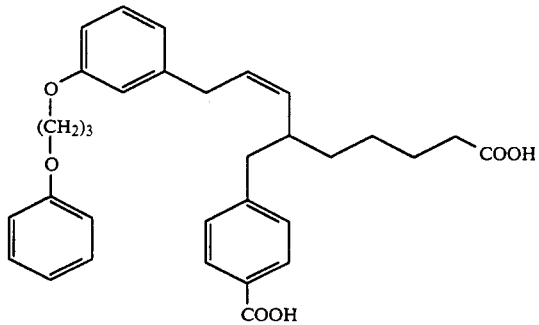

3.2 ml of 45% sodium hydroxide solution are added at 0° C. to a solution of 0.24 g (0.44 mmol) of the product of Example 67 in 19 ml of methanol. After heating the reaction solution to room temperature such a quantity of methylene chloride (about 3 ml) is added with stirring until a clear solution is formed. The reaction solution is left to stand for 6 hours at room temperature and is then diluted with water, brought to a pH of 3 with 2 n sulphuric acid and extracted twice with ethyl acetate. The combined organic phases are dried with sodium sulphate and concentrated by evaporation.

Yield: 92.2% of theory.

NMR (CDCl$_3$, 300 MHz): 1.3-1.7 [6] m, 2.25 [2] quintet, J=8 Hz, 2.3 [2] tr, J=8 Hz, 2.55 [1] d, J=13 Hz, J=8 Hz, 2.65-2.8 [2] m, 3.0 [1] dd, J=14 Hz, J=8 Hz, 3.15 [1] dd, J=14 Hz, J=8 Hz, 4.1 [2] tr, J=8 Hz, 4.15 [2] tr, J=8 Hz, 5.2 [1] tr, J=10 Hz, 5.55 [1] d, tr, J=10 Hz, J=7 Hz, 6.5 [1] d, J=8 Hz, 6.55 [1] s, 6.7 [1] dd, J=8 Hz, J=1 Hz, 7.85-7.95 [3] m, 7.1 [1] tr, J=8 Hz, 7.2-7.3 [4] m, 7.95 [2] d, J=8 Hz.

EXAMPLE 69

6-(4-Methoxycarbonylbenzyl)-10-[4-(3-phenoxypropoxy)phenyl]-7(Z)-decenoic acid methyl ester

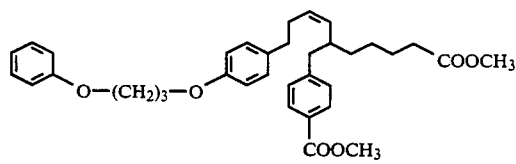

0.84 g (1.2 mmol) of 3-[4-(4tosylate are reacted with -phenoxy-butoxy)phenyl] propyltriphenylphosphonium 0.31 g (1 mmol) of 6-formyl-7-(4-methoxycarbonylphenyl)heptanoic acid methyl ester following the same procedure as in Example 67. 0.12 g of a solid product are thus obtained.

Yield: 18% of theory.

NMR (CDCl$_3$, 300 MHz): 1.15-1.7 [6] m, 1.9-2.15 [2] m, 2.2-2.6 [8] m, 2.7 [1] dd, J=14 Hz, J=7 Hz, 3.65 [3] s, 3.9 [3] s, 4.1-4.2 [4] m, 5.05 [1] tr, J=10 Hz, 5.35 [1] d, tr, J=14 Hz, J=10 Hz, 6.8 [2] d, J=8 Hz, 6,9-7.0 [5] m, 7.2 [2] d, J=8 Hz, 7.25-7.3 [2] m, 7.95 [2] d, J=8 Hz.

EXAMPLE 70

6-(4-Carboxybenzyl)-10-[4-(4-phenoxypropoxy)-phenyl]-7(Z)-decanoic acid

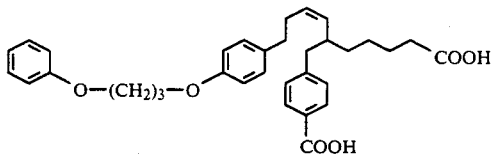

0.11 g of the product described in Example 69 are saponified following the same procedure as in Example 68. 0.1 g of a solid product are obtained.

Yield: 95.7% of theory.

NMR (CDCl$_3$, 300 MHz): 1.1-1.7 [6] m, 1.9-2.15 [2] m, 2.15-2.6 [8] m, 2.65 [1] dd, J=14 Hz, J=7 Hz, 4.05-4.15 [4] m, 5.05 [1] tr, J=10 Hz, 5.35 [1] d, tr, J=14 Hz, J=10 Hz, 6.8 [2] d, J=8 Hz, 6.85-7.0 [5] m, 7.2 [2] d, J=8 Hz, 7.2-7.3 [2] m, 8.0 [2] d, J=8 Hz.

EXAMPLE 71

6-(4-Methoxycarbonylbenzyl)-9-[4-(4-phenoxybutoxy)-phenyl]-7(Z)-nonenoic acid methyl ester

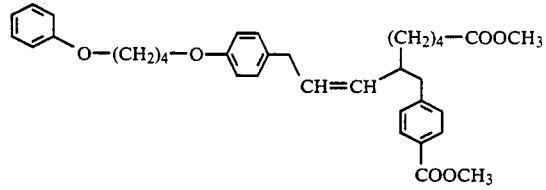

0.843 g (1.2 mmol) of 2-[4-(4-phenoxybutoxy)phenyl]ethyltriphenylphosphonium tosylate are reacted with 0.31 g (1 mmol) of 6-formyl-7-(4-methoxycarbonylphenyl)heptanoic acid methyl ester following the same procedure as in Example 67. 0.32 g of the product are thus obtained.

Yield: 57.3% of theory.

R$_f$-value: 0.17 (n-hexane:ether 8:2).

NMR (CDCl$_3$, 300 MHz): 1.3-1.7 [6] m, 1.9-2.0 [4] m, 2.3 [2] tr, J=8 Hz, 2.55 [1] dd, J=13 Hz, J=8 Hz, 2.65-2.8 [2] m, 2.95-3.15 [2] m, 3.65 [2] s, 3.9 [3] s, 3.95-4.05 [4] m, 5.2 [1] tr, J=10 Hz, 5.45 [1] d tr, J=10 Hz, J=7 Hz, 6.7-6.8 [3] m, 6.9-7.0 [3] m, 7.2-7.35 [5] m, 7.95 [2] d, J=8 Hz.

EXAMPLE 72

6-(4-Carboxybenzyl)-9-[4-(4-phenoxybutoxy)phenyl]-7(Z)-nonenoic acid

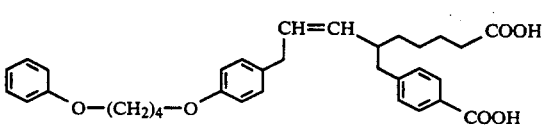

0.27 g of the product described in Example 70 are saponified following the same procedure as in Example 68. 0.24 g of a solid product is obtained.

Yield: 93.6% of theory.

R$_f$-value: 0.2 (methylene chloride:methanol 95:5).

NMR (CDCl$_3$, 300 MHz): 1.3-1.7 [6] m, 1.9-2.0 [4] m, 2.25 [2] tr, J=8 Hz, 2.55 [1] dd, J=13 Hz, J=8 Hz, 2.65-2,8 [2] m, 2.95-3.15 [2] m, 3.95-4.05 [4] m, 5.2 [1] tr, J=10 Hz, 5.45 [1] d tr, J=10 Hz, J=7 Hz, 6.7-6.8 [9] m, 6.85-6.95 [3] m, 7.15-7.3 [5] m, 7.95 [2] d, J=8 Hz.

EXAMPLE 73

6-(4-Methoxycarbonylbenzyl)-9-[4-(4-phenoxybutoxy)-phenyl]-5-thia-7(Z)-nonenoic acid methyl ester

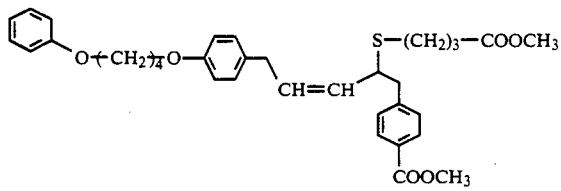

0.843 g (1.2 mmol) of 2-[4-(4-phenoxybutoxy)phenyl]ethyltriphenylphosphonium tosylate are reacted with 0.32 g (1 mmol) of 6-formyl-7-(4-methoxycarbonylphenyl)-5-thiaheptanoic acid methylester following the same procedure as in Example 67. 0.22 g of the product are thus obtained.

Yield: 38% of the theory.

$R_f$-value: 0,44 (n-hexane:ether 60:40).

NMR (CDCl$_3$, 300 MHz): 1.8-2.0 [6] m, 2.4 [2] tr, J=8 Hz, 2.45-2.6 [2] m, 2.8 [1] dd, J=14 Hz, J=8 Hz, 3.0-3.1 [3] m, 3.65 [3] s, 3.9 [3] s, 3.9-4.05 [5] m, 5.2 [1] tr, J=10 Hz, 5.55 [1] d tr, J=10 Hz, J=7 Hz, 6.7 [3] s, 6.85-6.95 [3] m, 7.2-7.3 [5] m, 7.95 [2] d, J=8 Hz.

EXAMPLE 74

6-(4-Carboxybenzyl)-9-[4-(4-phenoxybutoxy)phenyl]-5-thia-7(Z)-nonenoic acid

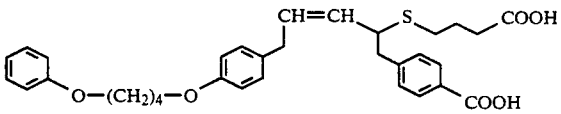

0.1 g of the product obtained in Example 72 is saponified following the same procedure as in Example 68. 90 mg of a solid product are thus obtained.

Yield: 96% of theory.

$R_f$-value: 0.5 (methylene chloride:methanol 9:1).

NMR (CDCl$_3$, 300 MHz): 1.8-2.0 [6] m, 2.35-2.65 [4] m, 2.8 [1] d, J=13 Hz, J=8 Hz, 3.0-3.15 [3] m, 3.9-4.05 [5] m, 5.35 [1] tr, J=10 Hz, 5.6 [1] d tr, J=10 Hz, J=8 Hz, 6.7 [3] s, 6.85-6.95 [3], 7.2-7.3 [5] m, J=8 Hz.

EXAMPLE 75

6-(4-Methoxycarbonylbenzyl)-10-[4-(3-phenoxypropoxy)phenyl]-5-thia-7(Z)-decenoic acid methyl ester

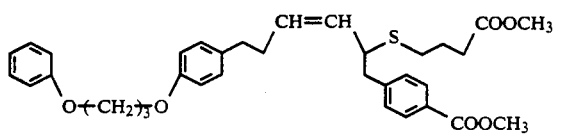

0.84 g (1.2 mmol) of 3-[4-(3-phenoxypropoxy)-phenyl]propyltriphenylphosphonium tosylate are reacted with 0.32 g (1 mmol) of 6-formyl-7-(4-methoxycarbonylphenyl)-5-thiaheptanoic acid methyl ester following the same procedure as in Example 67, 0.21 g of the product are thus obtained.

Yield: 36.4% of theory.

$R_f$-value: 0.43 (hexane:ether 60:40).

NMR (CDCl$_3$, 300 MHz): 1.75-1.9 [2] m, 1.9-2.5 [10] m, 2.7 [1] dd, J=14 Hz, J=10 Hz, 2.95 [1] dd, J=14 Hz, J=7 Hz, 3.65 [3] s, 3.8 [1] tr d, J=10 Hz, J=7 Hz, 3.9 [3] s, 4.1-4.2 [4] m, 5.2 [1] tr, J=10 Hz, 5.45 [1] d tr, J=10 Hz, J=8 Hz, 6.8 [2] d, J=8 Hz, 6.85-7.0 [5] m, 7.15-7.3 [4] m, 7.95 [2] d, J=8 Hz.

EXAMPLE 76

6-(4-Carboxybenzyl)-10-[4-(3-phenoxypropoxy)-phenyl]-5-thia-7(Z)-decenoic acid

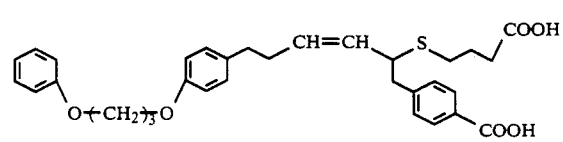

0.17 g of the product obtained in Example 74 are saponified following the same procedure as in Example 68. 0.15 g of the product are thus obtained.

Yield: 92.7% of theory.

$R_f$-value: 0.3 (methylene chloride:methanol 95:5).

EXAMPLE 77

6-(4-Methoxycarbonylbenzyl)-9-[3-(3-phenoxypropoxy)phenyl]-5-thia-7(Z)-nonenoic acid methyl ester

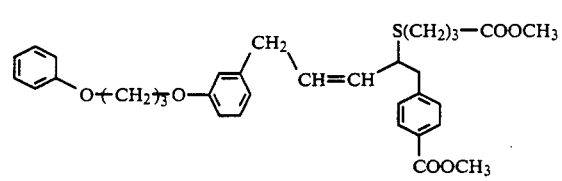

0.84 g (1.2 mmol) of 2-[3-(3-phenoxypropoxyphenyl]ethyltriphenylphosphonium tosylate are reacted with 0.32 g (1 mmol) of 6-formyl-7-(4-methoxycarbonylphenyl)-5-thiaheptanoic acid methyl ester following the same procedure as in example 67, 0.17 g of the product are thus obtained.

Yield: 30.2% of theory.

$R_f$-value: 0.18 (n-hexane:ether 7:3).

NMR (CDCl$_3$, 300 MHz): 1.9 [2] quintet, J=8 Hz, 2.25 [2] quintet, J=8 Hz, 2.35 [2] tr, J=8 Hz, 2.4-2.6 [2] m, 2.8 [1] dd, J=14 Hz, J=10 Hz, 3.05 [1] dd, J=14 Hz, J=8 Hz, 3.1-3.2 [2] m, 3.65 [3] s, 3.9 [3] s, 3.9-4.0 [1] m, 4.1 [2] tr, J=8 Hz, 4.15 [2] tr, J=8 Hz, 5.35 [1] tr, J=10 Hz, 5.6 [1] d, tr, J=10 Hz, J=8 Hz, 6.4 [1] d, J=8 Hz, 6.55 [1] s, 6.7 [1] dd, J=8 Hz, J=1 Hz, 6.9-7.0 [3] m, 7.05 [1] tr, J=8 Hz, 7.25-7.35 [4] m, 7.95 [2] d, J=8 Hz.

EXAMPLE 78

6-(4-Carboxybenzyl)-9-[3-(3-phenoxypropoxy)phenyl]-5-thia-7(Z)-nonenoic acid

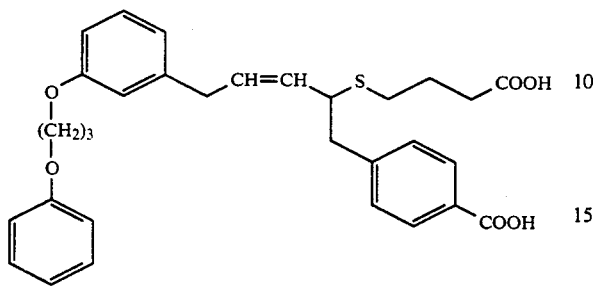

0.15 g of the product described in Example 76 are saponified following the same procedure as in Example 68. 0.13 g of the solid product are thus obtained.

Yield: 80.5% of theory.

$R_f$-value: 0.3 (methylenechloride: methanol 95:5).

NMR (CDCl$_3$, 300 MHz): 1.8-1.95 [2] m, 2.25 [2] quintet, J=8 Hz, 2.35-2.65 [4] m, 2.8 [1] dd, J=14 Hz, J =10 Hz, 3.05 [1] dd, J=14 Hz, J=8 Hz, 3.05-3.2 [2] m, 3.95 [1] tr, d, J=10 Hz, J=8 Hz, 4.05-4.2 [4] m, 5.4.[1] tr, J=10 Hz, 5.65 [1] d tr, J=10 Hz, J=8 Hz, 6.4 [1] d, J=8 Hz, 6.5 [1] s, 6.7 [1] dd, J=8 Hz, J=1 Hz, 6.85-6.95 [3] m, 7.1 [1] tr, J =8 Hz, 7.2-7.3 [4] m, 8.0 [2] d, J=8 Hz.

EXAMPLE 79

6-(4-Methoxycarbonylbenzyl)-9-[2-(3-phenoxypropoxy)phenyl]-5-thia-7(Z)-nonenoic acid methyl ester

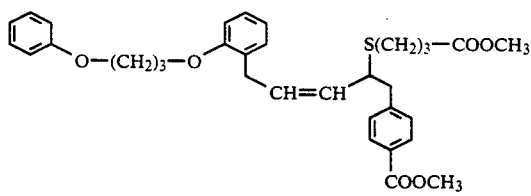

0.84 g (1.2 mmol) of 2-[2-(3-phenoxypropoxy)phenyl-]ethyltriphenylphosponium tosylate are reacted with 0.32 g (1 mmol) of 6-formyl-7-(4-methoxycarbonyl-phenyl)-5-thiaheptanoic acid methyl ester following the same procedure as in Example 67. 0.18 of the product are thus obtained.

Yield: 32% of theory.

$R_f$-value: 0.16 (n-hexane:ether 7:3).

NMR (CDCl$_3$, 300 MHz): 1.85 [2] quintet, J=8 Hz, 2.25 [2] quintet, J=8 Hz, 2.35 [2] tr, J=8 Hz, 2.4-2.6 [2] m, 2.7 [1] dd, J=14 Hz, J=10 Hz, 3.0 [1] dd, J=14 Hz, J=8 Hz, 3.05 [1] dd, J=14 Hz, J=8 Hz, 3.2 [1] dd, J=14 Hz, J=8 Hz, 3.65 [3] s, 3.9 [3] s, 3.95 [1] tr, d, J=10 Hz, J=8 Hz, 4.1-4.2 [4] m, 5.4 [1] tr, J=8 Hz, 5.65 [1] d, tr, J=10 Hz, J=8 Hz, 6.15-7.0 [6] m, 7.1 [1] tr, J=8 Hz, 7.2-7.35 [4] m, 7.9 [2] d, J=8 Hz.

EXAMPLE 80

6-(4-Carboxybenzyl)-9-[2-(3-phenoxypropoxy)phenyl]-5-thia-7(Z)-nonenoic acid

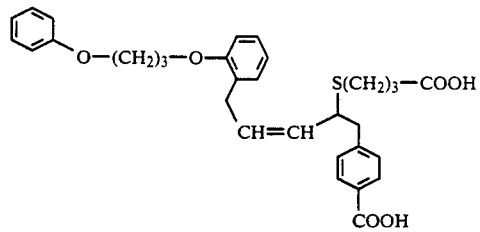

0.17 g of the product obtained in Example 78 are saponified following the same procedure as in Example 68.90 mg of a solid product are thus obtained.

Yield: 55.7% of theory.

$R_f$-value: 0.32 (methylenechloride:methanol 95:5).

NMR (CDCl$_3$, 300 MHz): 1.8-1.95 [2] m, 2.25 [2] quinetet, J=8 Hz, 2.35-2.6 [4] m, 2.8 [1] dd, J=14 Hz, J=10 Hz, 3.0 [1] dd, J=14 Hz, J=8 Hz, 3.1 [1] dd, J=14 Hz, J=8 Hz, 3.25 [1] dd, J=14 Hz, J=8 Hz, 3.95 [1] tr, d, J=10 Hz, J=8 Hz, 4.1-4.2 [4] m, 5.35 [1] tr, J=10 Hz, 5.7 [1] d, tr, J=10 Hz, J=8 Hz, 6.2-7.0 [6] m, 7.1 [1] tr, d, J=8 Hz, J=1 Hz, 7.2-7.35 [4] m, 8.0 [2] d, J=8 Hz.

EXAMPLE 81

6-(4-Methoxycarbonylbenzyl)-9-[4-(3-phenoxypropoxy)phenyl]-5-thia-7(Z)-nonenoic acid methyl ester

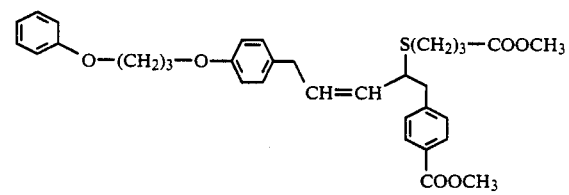

0.84 g 81.2 mmol) of 2-[4-(3-phenoxypropoxy)phenyl-]ethyltriphenylphosphoniumtosylate are reacted with 0.32 g (1 mmol) of 6-formyl-7-(4-methoxycarbonyl-phenyl)5-thiaheptanoic acid methyl ester following the same procedure as in Example 67. 0.11 g of the product are thus obtained.

Yield: 19.5% of theory.

$R_f$-value: 0.16 (n-hexane:ether 7:3).

NMR (CDCl$_3$, 300 MHz): 1.9 [2] quintet, J=8 Hz, 2.25 [2] quintet, J=8 Hz, 2.35-2.65 [4] m, 2.8 [1] dd, J=14 Hz, J=10 Hz, 3.0-3.1 [3] m, 3.7 [3] s, 3.9 [3] s, 3.9-4.0 [1] m, 4.05-4.2 [4] m, 5.3 [1] tr, J=10 Hz, 5.6 [1] tr, d, J=10 Hz, J=8 Hz, 6.2 [3] s, 6.9-7.0 [3] m, 7.25-7.4 [5] m, 7.95 [2] d, J=8 Hz.

EXAMPLE 82

6-(4-Carboxybenzyl)-9-[4-(3-phenoxypropoxy)phenyl]-5-thia-7(Z)-nonenoic acid

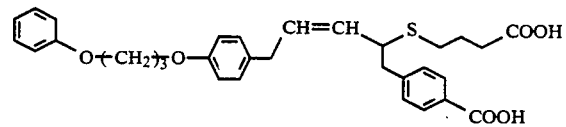

80 mg of the product obtained in Example 80 are saponified following the same procedure as in Example 68. 70 mg of the product are thus obtained.

Yield: 92.2% of theory.

NMR (CDCl$_3$, 300 MHz): 1.9 [2] quintet, J=8 Hz, 2,25 [2] quintet, J=8 Hz, 2.4 [2] tr, J=8 Hz, 2.45-2.65 [2] m, 2.8 [1] dd, J=14 Hz, J=10 Hz, 3.0-3.1 [3] m, 3.95 [1] tr, d, J=10 Hz, J=8 Hz, 4.1-4, [4] m, 5.3 [1] tr, J=10 Hz, 5.55 [1] d, tr, J=10 Hz, J=8 Hz, 6.15-6.25 [3] m, 6.9-7.0 [3] m, 7.25-7.3 [4] m, 8.0 [2] d, J=8 Hz.

EXAMPLE 83

6-(4-Methoxycarbonylbenzyl)-9-[2-(3-phenoxypropoxy)phenyl]-7(Z)-nonenoic acid methyl ester

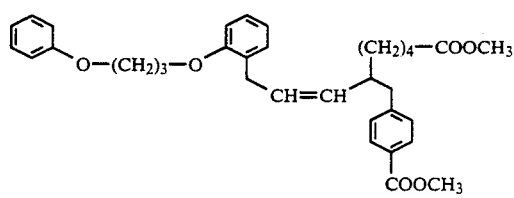

0.84 g (1.2 mmol) of 2-[2-(3-phenoxypropoxy)phenyl]ethyltriphenylphosphonium tosylate are reacted with 0.31 g (1 mmol) of 6-formyl-7-(4-methoxycarbonylphenyl)heptanoic acid methyl ester following the same procedure as in Example 67. 0.28 g of the product are thus obtained.

Yield: 51.4% of theory.

R$_f$-value: 0.31 (n-hexane:ether 7:3).

NMR (CDCl$_3$, 300 MHz): 1.2-1.65 [6] m, 2.3-2.4 [4] m, 2.55 [1] dd, J=14 Hz, J=10 Hz, 2.65-2.8 [2] m, 3.0 [1] dd, J=14 Hz, J=8 Hz, 3.15 [1] dd, J=14 Hz, J=8 Hz, 3.65 [3] s, 3.9 [3] s, 4.1-4.2 [4] m, 5.2 [1] tr, J=10 Hz, 5.55 [1] tr, d, J=10 Hz, J=8 Hz, 6.7-7.0 [6] m, 7.05-7.15 [1] m, 7.2 [2] d, J=8 Hz, 7.25 [2] d, J=8 Hz, 7.9 [2] d, J=8 Hz.

EXAMPLE 84

6-(4-Carboxybenzyl)-9-[2-(3-phenoxypropoxy)phenyl]-7-(Z)-nonenoic acid

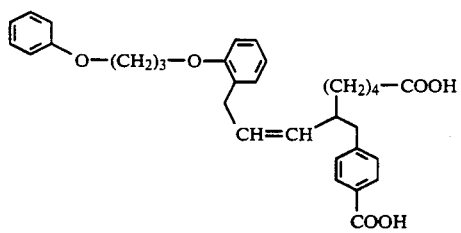

0.25 g of the product obtained in Example 78 are reacted following the same procedure as in Example 68. 0.21 g of the product are thus obtained.

Yield: 88.6% of theory.

R$_f$-value: 0.44 (methylenechloride:methanol 95:5).

NMR (CDCl$_3$, 300 MHz): 1.2-1.7 [6] m, 2.2-2.4 [4] m, 2.55 [1] dd, J=14 Hz, J=10 Hz, 2.65-2.8 [2] m, 3.0 [1] dd, J=14 Hz, J=8 Hz, 3.15 [1] dd, J=14 Hz, J=8 Hz, 4.05-4.2 [4] m, 5.2 [1] tr, J=10 Hz, 5.55 [1] d, tr, J=10 Hz, J=8 Hz, 6.7-7.0 [6] m, 7.05-7.35 [5], 7.95 [2] d, J=8 Hz.

EXAMPLE 85

6-(4-Methoxycarbonylbenzyl)-9-[4-(3-phenoxypropoxy)phenyl]-7(Z)-nonenoic acid methyl ester

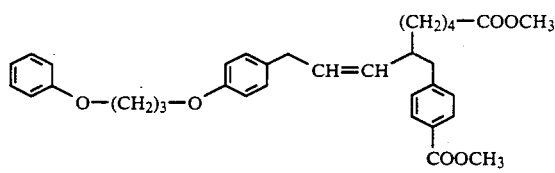

0.84 g (1.2 mmol) of 2-[4-(3-phenoxypropoxy)phenyl]ethyltriphenylphosphoniumtosylate are reacted with 0.31 g (1 mmol) of 6-formyl-7-(4-methoxycarbonylphenyl)heptanoic acid methylester following the same procedure as in Example 67. 0.12 g of the product are thus obtained.

Yield: 22% of theory.

R$_f$-value: 0.26 (n-hexane:ether 7:3).

NMR (CDCl$_3$, 300 MHz): 1.2-1.7 [6] m, 2.2-2.4 [4] m, 2.55 [1] dd, J=14 Hz, J=10 Hz, 2.65-2.8 [2] m, 2.9-3.1 [2] m, 3.65 [3] s, 3.9 [3] s, 4.1-4.2 [4] m, 5.2 [1] tr, J=10 Hz, 5.5 [1] d, tr, J=10 Hz, J=8 Hz, 6.7-6.8 [3] m, 6.9-7.0 [3] m, 7.15-7.3 [5] m, 7.9 [2] d, J=8 Hz.

EXAMPLE 86

6-(4-Carboxybenzyl)-9-[4-(3-phenoxypropoxy)phenyl]-7(Z)-nonenoic acid

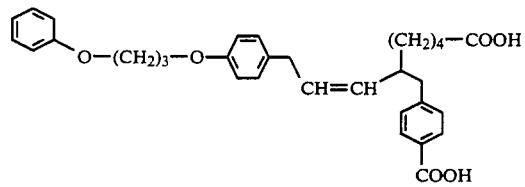

0.11 g of the product obtained in Example 80 are reacted following the same procedure as in Example 68. 0.1 g of the product are thus obtained.

Yield: 95.8% of theory.

NMR (CDCl$_3$, 300 MHz): 1.2-1.7 [6] m, 2.25 [2] quintet, J=8 Hz, 2.35 [2] tr, J=8 Hz, 2.55 [1] dd, J=14 Hz, J=10 Hz, 2.65-2.8 [2] m, 2.95-3.1 [[2] m, 4.05-4.15 [4] m, 5.2 [1] tr, J=10 Hz, 5.5 [1] d, tr, J=10 Hz, J=8 Hz, 6.7-6.8 [3] m, 6.85-6.95 [3] m, 7.2-7.3 [5] m, 8.0 [2] d, J=8 Hz.

EXAMPLES 87 AND 88

6-(4-Methoxycarbonylbenzyl)-8-[4-(4-phenoxybutoxy)phenyl]-7(E)-octenoic acid methyl ester (trans-isomer)

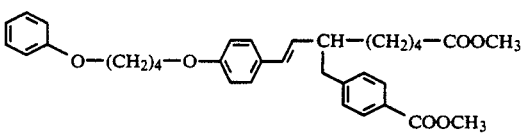

and 6-(4-Methoxycarbonylbenzyl)-8-[4-(4-phenoxybutoxy)-phenyl]-7(Z)-octenoic acid methylester (cis-isomer)

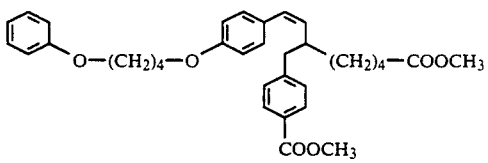

0.79 ml (1 mmol of n-butyllithium in hexane (content titrated) are added dropwise at −25° C., under nitrogen to a solution of 0.72 g (1.2 mmol) of 4-(4-phenoxybutoxy)benzyltriphenylphosphonium bromide in 10 ml of absolute tetrahydrofuran. The reaction solution is subsequently stirred for 10 minutes at −25° C. and cooled to −70° C. Then at −70° C. 1.8 ml of absolute DMPU are added dropwise followed by a solution of 0.31 g (1 mmol) of 6-formyl-7-(4-methoxycarbonylphenyl)heptanoic acid methyl ester in 2 ml of absolute tetrahydrofuran. The mixture is subsequently stirred at −70° C. for 30 minutes, 0.5 ml of methanol are then added and the mixture is heated slowly to 0° C. After stirring for 30 mins. at 0° C. the mixture is diluted with water and extracted with ethylacetate. The organic phase is washed with water and a saturated sodium chloride solution, dried with sodium sulphate and concentrated by evaporation. The residue is chromatographed with hexane/ether 9/1 and 8/2 on 50 g of silica gel (Merck Si 60, 0.04–0.063 mm). 2 fractions are thus obtained, the second of which contains the pure trans-isomer. The first fraction contains a mixture of the cis- and the trans-isomer and after being concentrated by evaporation is once again chromatographed with hexane/ether 70/30 on 250 g of silica gel. 2 fractions are thus obtained of which the first, after being concentrated by evaporation, yields 60 mg of the pure cis-isomer. After concentration by evaporation of the second fraction, together with the second fraction from the first chromatographic process, 0.29 g of the pure trans-isomer are obtained.

Yield: 11% of theory of the cis-isomer, 53% of theory of the trans-isomer.

R$_f$-value: 0.27 for the cis-isomer (n-hexane:ether 7:3), 0.21 for the trans-isomer (n-hexane:ether 7:3).

NMR (CDCl$_3$, 300 MHz) of the cis-isomer: 1.2–1.7 [6] m, 1.95–2.0 [4] m, 2.25 [2] tr, J=8 Hz, 2.6–2.8 [2] m, 2.85–3.9 [1] m, 3.65 [3] s, 3.9 [3] s, 4.0–4.1 [4] m, 5.3 [1] tr, J=10 Hz, 6.4 [1] d, J=10 Hz, 6.7–7.0 [7] m, 7.1–7.3 [4] m, 7.9 [2] d, J=8 Hz. of the trans-isomer: 1.2–1.7 [6] m, 1.95–2.0 [4] m, 2.25 [2] tr, J=8 Hz, 2.35–2.45 [1] m, 2.65–2.85 [2] m, 3.65 [3] s, 3.9 [3] s, 4.0–4,1 [4] m, 5.8 [1] dd, J=14 Hz, J=8 Hz, 6.15 [1] d, J=14 Hz, 6.85–6.95 [3] m, 7.2–7.35 [6] m, 7.95 [2] d, J=8 Hz.

EXAMPLE 89

6-(4-Carboxybenzyl)-8-[4-(4-phenoxybutoxy)phenyl]-7(E)-octenoic acid

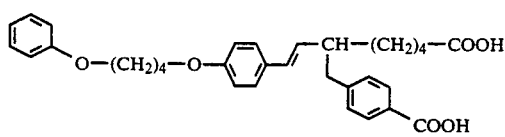

0.24 g of the product obtained in Example 87 (trans-isomer) are saponified following the same procedure as in Example 68. 0.2 g of the product are thus obtained.

Yield: 87.8% of theory.

NMR (CDCl$_3$, 300 MHz): 1.2–1.7 [6] m, 1.95 [4] s, 2.3 [2] tr, J=8 Hz, 2.35–2.5 [1] m, 2.7–2.8 [2] m, 3.95–4.05 [4] m, 5.8 [1] dd, J=14 Hz, J=8 Hz, 6.2 [1] d, J=14 Hz, 6.8 [2] d, J=8 Hz, 6.85–7.0 [3] m, 7.15–7.3 [6] m, 8.0 [2] d, J=8 Hz.

EXAMPLE 90

6-(4-Carboxybenzyl)-8-[4-(4-phenoxybutoxy)phenyl]-7(Z)-octenoic acid

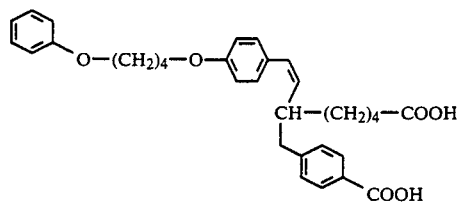

50 mg of the compound obtained in Example 88 (cisisomer) are saponified following the same procedure as in Example 68. 40 mg of the product are thus obtained.

Yield: 84.2% of theory.

NMR (CDCl$_3$, 300 MHz): 1.2–1.7 [6] m, 1.95–2.0 [4] m, 2.3 [2] tr, J=8 Hz, 2.6–2.8 [2] m, 2.85–3.0 [1] m, 3.95–4.05 [4] m, 5.3 [1] tr, J=10 Hz 6.35 [1] d, J=10 Hz, 6.75 [2] d, J=8 Hz, 6.85–7.0 [5] m, 7.2 [2] d, J=8 Hz, 7.2–7.3 [2] m, 7.95 [2] d, J=8 Hz.

EXAMPLES 91 and 92

6-(4-Methoxycarbonylbenzyl)-8-[3-(4-phenoxybutoxy)-phenyl]-7(E)-octenoic acid methylester (transisomer)

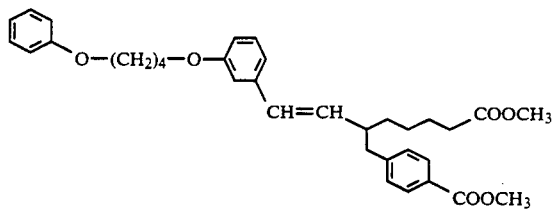

and 6-(4-Methoxycarbonylbenzyl)-8-[3-(4-phenoxybutoxy)-phenyl]-7(Z)-octenoic acid methylester (cisisomer)

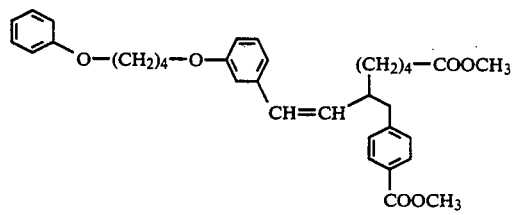

0.72 g (1.2 mmol) of 3-(4-phenoxybutoxy)benzyltriphenylphosphonium bromide are reacted with 0.31 g (1 mmol) of 6-formyl-7-(4-methoxycarbonyl)heptanoic acid methyl ester and chromatographed following the same procedure as in Examples 87 and 88, 58.8 mg of the cis-isomer and 0.32 g of the trans-isomer are thus obtained.

Yield: 10.8% of theory of the cis-isomer and 58.7% of theory of the trans-isomer.

R$_f$-value: 0.29 for the cis-isomer (n-hexane:ether 7:3) 0.25 for the trans-isomer (n-hexane:ether 7:3).

NMR (CDCl$_3$, 300 MHz) of the cis-isomer: 1.15–1.6 [6] m, 1.9–2.0 [4] m, 2.25 [2] tr, J=8 Hz, 2.6–2.8 [2] m, 2.8–3.0 [1] m, 3.65 [3] s, 3.9 [3] s, 3.95 [2] tr, J=8 Hz, 4.05 [2] tr, J=8 hz, 5.35 [1] tr, J=10 Hz, 6.4 [1] d, J=10 Hz, 6.45 [1] s, 6.55 [1] d, J=8 Hz, 6.75 [1] dd, J=8 Hz, J=1 Hz, 6.9–7.0 [3] m, 7.1–7.3 [5] m, 7.9 [2] d, J=8 Hz. of the trans-isomer: 1.25–1.7 [6] m, 1.95–2.05 [4] m, 2.25 [2] tr, J=8 Hz, 2.4–2.55 [1] m, 2.7–2.9 [2] m, 3.65 [3] s, 3.9 [3] s, 4.0–4.1 [4] m, 5.95 [1] dd, J=14 Hz, J=10 Hz, 6.15 [1] d, J=14 Hz, 6.75 [1] dd, J=8 Hz, J=1 Hz, 6.8–7.0 [5] m, 7.15–7.35 [5] m, 7.9 [2] d, J=8 Hz.

EXAMPLE 93

6-(4-Carboxybenzyl)-8-[3-(4-phenoxybutoxy)phenyl]-7(Z)-octenoic acid

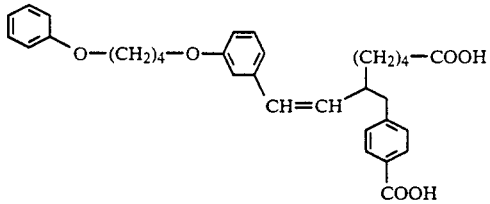

60 mg of the compound obtained in Example 92 (cis-isomer) are saponified following the same procedure as in Example 68, 30 mg of the product are thus obtained.

Yield: 52.8% of theory.

NMR (CDCl$_3$, 300 mHz): 1.15–1.6 [6] m, 1.9–2.0 [4] m, 2.2 [2] tr, J=8 Hz, 2.6–2.8 [2] m, 2.85–3.0 [1] m, 3.9 [2] s, wide, 4.05 [2] s, wide, 5.4 [1] tr, J=10 Hz, 6.4 [1] d, J=10 Hz, 6.45 [1] s, 6.55 [1] d, J=8 Hz, 6.7 [1] dd, J=8 Hz, J=1 Hz, 6.85–6.95 [3] m, 7.1–7.3 [5] m, 7.9 [2] d, J=8 Hz.

EXAMPLE 94

6-(4-Carboxybenzyl)-8-[3-(4-phenoxybutoxy)phenyl]-7(E)-octenoic acid

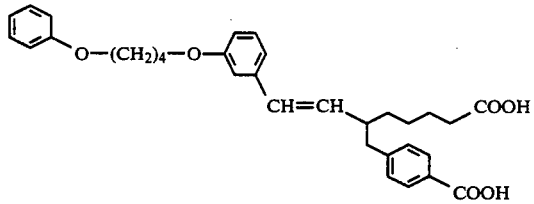

0.35 g of the compound obtained in Example 91 (trans-isomer) are saponified following the same procedure as in Example 68. 0.28 g of the product are thus obtained.

Yield: 84.3% of theory.

NMR (CDCl$_3$, 300 MHz): 1.25–1.7 [6] m, 1.95 [4] s, 2.3 [2] tr, J=8 Hz, 2.4–2.55 [1] m, 2.75 [2] d, J=8 Hz, 4.05 [4] s, 5.95 [1] dd, J=14 Hz, J=8 Hz, 6.2 [1] d, J=14 Hz, 6.7 [1] dd, J=8 Hz, J=1 Hz, 6.8–7.0 [5] m, 7.15–7.35 [5] m, 8.0 [2] d, J=8 Hz.

EXAMPLES 95 AND 96

6-(4-Methoxycarbonylbenzyl)-8-[4-(4-phenoxybutoxy)-phenyl]-5-thia-7(E)-octenoic acid methylester (transisomer)

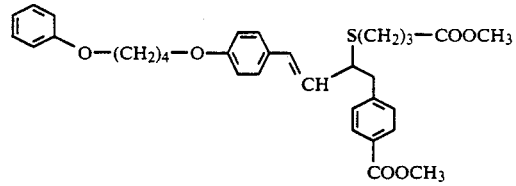

and 6-(4-Methoxycarbonylbenzyl)-8-[4-(4-phenoxybutoxy)-phenyl]-5-thia-7(Z)-octenoic acid methylester (cis-isomer)

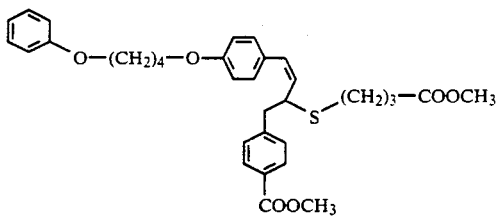

0.72 g (1.2 mmol) of 4-(4-phenoxybutoxy)benzyltriphenylphosphonium bromide are reacted with 0.32 g (1 mmol) of 6-formyl-7-(4-methoxycarbonylphenyl)-5-thiaheptanoic acid methyl ester and chromatographed following the same procedure as in Examples 87 and 88. 18.6 mg of the cis-isomer and 0.26 g of the trans-isomer are thus obtained.

Yield: 3.3% of theory of the cis-isomer, 46.2% of theory of the trans-isomer.

R$_f$-value: 0.22 for the cis-isomer (n-hexane:ether 7:3), 0.15 for the trans-isomer (n-hexane:ether 7:3).

NMR (CDCl$_3$, 300 MHz) of the cis-isomer: 1.55–17 [2] m, 1.9–2.0 [4] m, 2.25 [2] tr, J=8 Hz, 2.4 [2] tr, J=8 Hz, 2.95 [1] dd, J=14 Hz, J=10 Hz, 3.05 [1] dd, J=14 Hz, J=8 Hz, 3.6 [3] s, 3.9 [3] s, 3.95–4.15 [5] m, 5.4 [1] tr, J=10 Hz, 6.5 [1] d, J=10 Hz, 6.7–7.0 [7] m, 7.25–7.35 [4] m, 7.95 [2] d, J=8 Hz. of the trans-isomer: 1.75–2.0 [6] m, 2.3–2.6 [4] m, 2.95–3.1 [2] m, 3.6 [1] q, J=8 Hz, 3.65 [3] s, 3.9 [3] s, 4.05 [4] s wide, 5.85 [1] dd, J=14 Hz, J=8 Hz, 6.2 [1] d, J=14 Hz, 6.8 [2] d, J=8 Hz, 6.85–7.0 [3] m, 7.95 [2] d, J=8 Hz.

EXAMPLE 97

6-(4-Carboxybenzyl)-8-[4-(4-phenoxybutoxy)phenyl]-5-thia-7(E)-octenoic acid

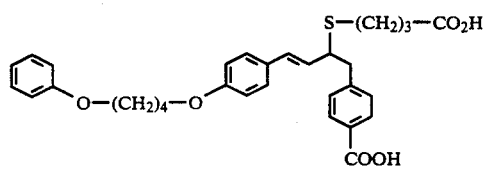

0.27 g of the compound obtained in Example 95 (trans-isomer) are saponified following the same procedure as in Example 68. 0.22 g of the product are thus obtained.

Yield: 85.7% of theory.

NMR (CDCl₃, 300 MHz): 1.75-2.05 [6] m, 2.25-2.6 [4] m, 2.9-3.1 [2] m, 3.6 [1] q, J=8 Hz, 4.0 [4] s, 5.85 [1] dd, J=14 Hz, J=8 Hz, 6.2 [1] d, J=14 Hz, 6.8-7.0 [5] m, 7.2-7.3 [6] m, 7.95 [2] d, J=8 Hz.

EXAMPLE 98

6-(4-Carboxybenzyl)-8-[4-(4-phenoxybutoxy)phenyl]-5-thia-7(Z)-octenoic acid

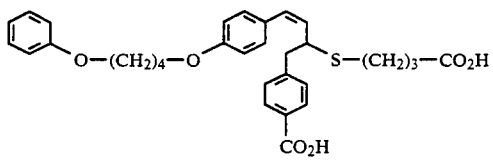

18 mg of the compound obtained in Example 96 (cis-isomer) are saponified following the same procedure as in Example 68. 15.6 mg of the product are thus obtained.

Yield: 91.2% of theory.

NMR (CDCl₃, 300 MHz): 1.6 [2] quintet, J=8 Hz, 2.9 [4] s wide, 2.3 [2] tr, J=8 Hz, 2.4 [2] tr, J=8 Hz, 2.9-3.1 [2] m, 3.9-4.15 [5] m, 5.4 [1] tr, J=10 Hz, 6.5 [1] d, J=10 Hz, 6.7-7.0 [7] m, 7.2-7.35 [4] m, 8.0 [2] d, J=8 Hz.

EXAMPLES 99 AND 100

6-(4-methoxycarbonylbenzyl)-8-[3-(4-phenoxybutoxy)-phenyl]-5-thia-7(Z)-octenoic acid methyl ester (cis-isomer)

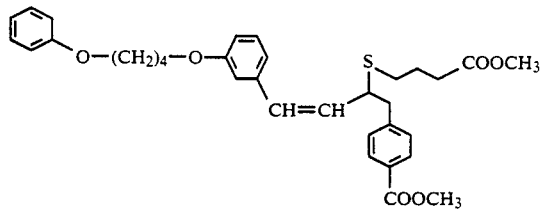

and 6-(4-methoxycarbonylbenzyl)-8-[3-(4-phenoxybutoxy)-phenyl]-5-thia-7-(E)-octenoic acid methyl ester (trans-isomer)

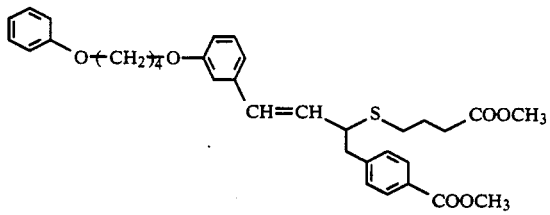

0.72 g (1.2 mmol) of 3-(4-phenoxybutoxy)benzyltriphenylphosphonium bromide, are reacted with 0.32 g (1 mmol) of 6-formyl-7-(4-methoxycarbonylphenyl)-5-thiaheptanoic acid methyl ester following the same procedure as in 87 and 88. 19.6 mg of the cis-isomer and 0.34 g of the trans-isomer are thus obtained.

Yield: 3.5% of theory of the cis-isomer and, 60.4% of theory of the trans-isomer.

R$_f$-value: 0.2 for the cis-isomer (n-hexane ether 7:3), 0.6 for the trans-isomer (n-hexane ether 7.3), NMR (CDCl₃, 300 MHz) of the cis-isomer: 1.5-1.7 [2] m, 1.9-2.0 [4] m, 2.2 [2] tr, J=8 Hz, 2.4 [2] tr, J=8 Hz, 2.9 [1] dd, J=14 Hz, J=10 Hz, 3.05 [1] dd, J=14 Hz, J=8 Hz, 3.6 [3] s, 3.9 [5] s wide, 4.0-4.15 [39 m, 5.5 [1] dr, J=10 Hz, 6.35 [1] s, 6.45 [1] d, J=8 Hz, 6.5 [1] d, J=10 Hz, 6.7 [1] dd, J=8 Hz, J=1 Hz, 6.85-7.0 [3] m, 7.1 [1] tr, J=8 Hz, 7.25-7.35 [4] m, 7.95 [2] d, J=8 Hz. of the trans-isomer: 1.75-2.05 [6] m, 2.3-2.65 [4] m, 2.95-3.1 [2] m, 3.6 [1] q, J=8 Hz, 3.65 [3] s, 3.9 [3] s, 4.05 [4] s wide, 6.0 [1] dd, J=14 Hz, J=8 Hz, 6.2 [1] d, J=14 Hz, 6.7 [1] dd, J=8 Hz, J=1 Hz, 6.8-7.0 [5] m, 7.2 [1] tr, J=8 Hz, 7.25-7.35 [4] m, 7.95 [2] d, J=8 Hz.

EXAMPLE 101

6-(4-Carboxybenzyl)-8-[3-(4-phenoxybutoxy)phenyl]-5-thia-7(Z)-octenoic acid

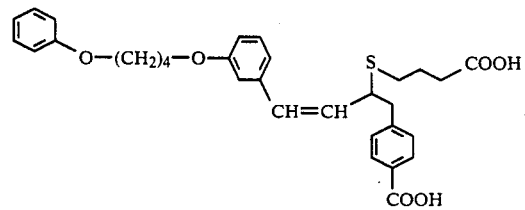

19 mg of the compound obtained in Example 99 (cis-isomer) are saponified following the same procedure as in Example 68. 18 mg of the product are thus obtained.

Yield: 99% of theory

NMR (CDCl₃, 300 MHz): 1.6 [2] quintet, J=8 Hz, 1.95 [4] s wide, 2.25 [2] tr, J=8 Hz, 2.4 [2] tr, J=8 Hz, 2.9-3.1 [2] m, 3.9 [2] s, wide, 4.0-4.1 [3] m, 5.5 [1] tr, J=10 Hz, 6.4 [1] s, 6.5 [1] d, J=8 Hz, 6.55 [1] d, J=14 Hz, 6.7 [1] dd, J=8 Hz, J=1 Hz, 6.85-7.0 [3] m, 7.15 [1] tr, J=8 Hz, 7.2-7.35 [4] m, 8.0 [2] d, J=8 Hz.

EXAMPLE 102

6-(4-Carboxybenzyl)-8-[3-(4-phenoxybutoxy)phenyl]-5-thia-7(E)-octenoic acid

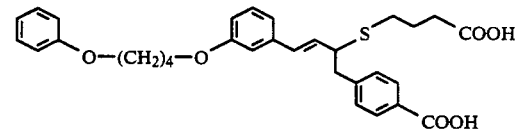

0.38 g of the compound obtained in Example 100 (trans-isomer) are saponified following the same procedure as in Example 68. 0.29 g of the product are obtained.

Yield: 80.4% of the theory.

NMR (CDCl₃, 300 MHz): 1.75-2.05 [6] m, 2.25-2.6 [4] m, 2.9-3.1 [2] m, 3.6 [1] q, J=8 Hz, 4.05 [4] s wide, 6.0 [1] dd, J=14 Hz, J=8 Hz, 6.2 [1] d, J=14 Hz, 6.75 [1] dd, J=8 Hz, J=1 Hz, 6.8-7.0 [5] m, 7.2 [1] tr, J=8 Hz, 7.25-7.35 [4] m, 7.95 [2] d, J=8 Hz.

EXAMPLE 103

6-(4-Methoxycarbonylbenzyl)-8-[2-(4-phenoxybutoxy)-phenyl]-5-thia-7(E)-octenoic acid methyl ester

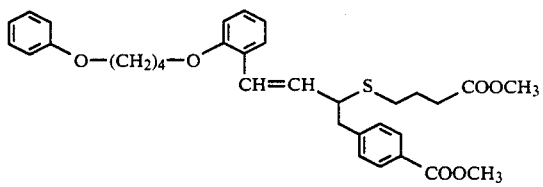

0.72 g (1.2 mmol) of 2-(4-phenoxybutoxy)benzyltriphenylphosphonium bromide are reacted with 0.32 g (1 mmol) of 6-formyl-7-(4-methoxycarbonylphenyl)-5-thiaheptanoic acid methyl ester following the same procedure as in Examples 87 and 88. 0.22 of the trans-isomer are thus obtained.

Yield: 51.5% of theory.

R$_f$-value: 0.22 (n-hexane:ether 7:3).

NMR (CDCl$_3$, 300 MHz): 1.75–2.05 [6] m, 2.3–2.65 [4] m, 3.0 [2] d, J=8 Hz, 3.6 [3] s, 3.65 [1] q, J=8 Hz, 3.9 [3] s, 4.05 [4] tr, J=7 Hz, 6.0 [1] dd, J=14 Hz, J=8 Hz, 6.55 [1] d, J=14 Hz, 6.8–7.0 [5] m, 7.1–7.35 [5] m, 7.4 [1] d, J=8 Hz, 7.95 [2] d, J=8 Hz.

EXAMPLE 104

6-(4-Carboxybenzyl)-8-[2-(4-phenoxybutoxy)phenyl]-5-thia-7(E)-octenoic acid

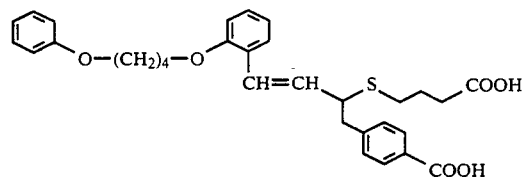

0.29 g of the compound obtained in Example 103 are saponified following the same procedure as in Example 68. 0.1 g of the product are thus obtained.

Yield: 39.9% of theory.

NMR (CDCl$_3$, 300 MHz): 1.75–2.0 [6]0 m, 2.25–2.6 [4] m, 2.95–3.05 [2] m, 3.65 [1] q, J=8 Hz, 3.95–4.05 [4] m, 6.0 [1] dd, J=14 Hz, J=8 Hz, 6.55 [1] d, J=8 Hz, 6.8–7.0 [5] m, 7.1–7.35 [5] m, 7.4 [1] d, J=8 Hz, 7.95 [2] d, J=8 Hz.

EXAMPLE 105

6-(4-Methoxycarbonylbenzyl)-8-[2-(4-phenoxybutoxy)-phenyl]-7(E)-octenoic acid methyl ester

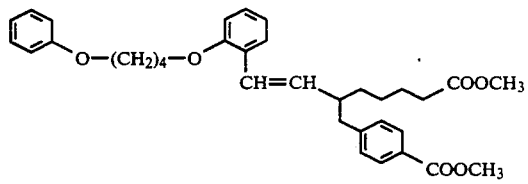

0.72 g (1.2 mmol) of 2-(4-phenoxybutoxy)benzyltriphenylphosphonium bromide are reacted with 0.31 g (1 mmol) of 6-formyl-7-(4-methoxycarbonylphenyl) heptanoic acid methyl ester following the same procedure as in Examples 87 and 88. Only the trans-isomer is isolated, of which 0.4 g are obtained.

Yield: 73.4% of theory.

R$_f$-value: 0.32 (n-hexane:ether 7:3).

NMR (CDCl$_3$, 300 MHz): 1.2–1.7 [6] m, 1.9–2.0 [4] m, 2.25 [2] tr, J=8 Hz, 2.4–2.55 [1] m, 2.7–2.9 [2] m, 3.6 [3] s, 3.9 [3], 3.95–4.05 [4] m, 6.0 [1] dd, J=14 Hz, J=8 Hz, 6.55 [1] d, J=14 Hz, 6.7–7.0 [5] m, 7.1–7.3 [5] m, 7.35 [1] d, J=8 Hz, 7.95 [2] d, J=8 Hz.

EXAMPLE 106

6-(4-Carboxybenzyl)-8-[2-(4-phenoxybutoxy)phenyl]-7(E)-octenoic acid

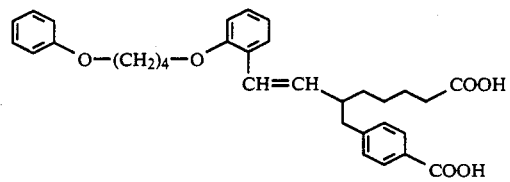

0.4 g of the compound obtained in Example 105 are saponified following of the same procedure as in Example 68. 0.35 g of the product are thus obtained.

Yield: 92.3% of theory.

NMR (CDCl$_3$, 300 MHz): 1.2–1.7 [6] m, 1.9–2.0[4] m, 2.3 [2] tr, J=8 Hz, 2.4–2.55 [1] m, 2.7–2.75 [29 m, 3.95–4.05 [4] m, 5.95 [1] dd, J=14 Hz, J=8 Hz, 6.55 [1] d, J=14 Hz, 6.7–7.0 [5] m, 7.1–7.3 [5] m, 7.35 [1] d, J=8 Hz, 8.0 [2] d, J=8 Hz.

EXAMPLE 107

6-(4-Methoxycarbonylphenyl)-9-[4-(3-phenoxypropoxy)phenyl]-7(Z)-nonenoic acid methyl ester

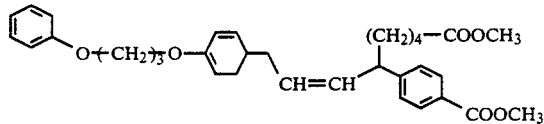

0.47 g (0.6 mmol) of 2-[4-(3-phenoxypropoxy)phenyl]ethyltriphenylphosphonium tosylate are reacted with 0.15 g (0.5 mmol) of 6-formyl-6-(4-methoxycarbonylphenyl)-hexanoic acid methyl ester following the same procedure as in Example 67. 10.7 mg of the product are thus obtained.

Yield: 4% of theory.

R$_f$-value: 0.49 (n-hexane:ether 1:1).

NMR (CDCl$_3$, 300 MHz): 1.2–1.7 [6] m, 2.2–2.4 [49 m, 3.4 [2] d, J=8 Hz, 3.65 [3] s, 3.75 [1] q, J=8 Hz, 3.9 [3] s, 4.1–4.2 [4] m, 5.55–5.65 [2] m, 6.7–7.0 [6] m, 7.2–7.35 [5, 8.0 [2] d, J=8 Hz.

EXAMPLE 108

6-(4-Carboxyphenyl)-9-[4-(3-phenoxypropoxy)phenyl]-7(Z)-nonenoic acid

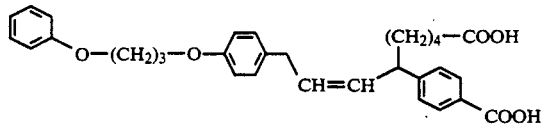

10.7 mg of the compound obtained in Example 107 are saponified following the same procedure as in Example 68. 8.6 mg of the product are thus obtained.

Yield: 85.6% of theory.

NMR (CDCl$_3$, 300 MHz): 1.2–1.7 [6] m, 2.2–2.4 [4] m, 3.4 [2] m, 3.8 [1] q, J=8 Hz, 4.1–4.2 [4] m, 5.05–5.2 [2] m, 6.7–7.0 [6] m, 7.2–7.4 [5] m, 8.0 [2] d, J=8 Hz.

EXAMPLE 109

6-(4-Ethoxycarbonylbenzyl)-7(Z), 10(Z)-hexadecadienoic acid ethyl ester

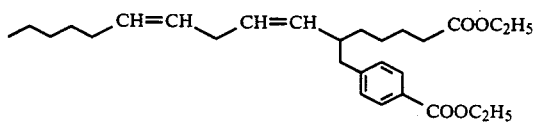

0.67 g (1.2 mmol) of 3(Z)-nonenyltriphenyl- of 7-(4-ethoxycarbonylphenyl)-6-formylheptanoiacid ethyl ester and chromatographed following the same procedure as in Example 67. 0.3 g of oily product are thus obtained.

Yield: 68% of theory.

Rf-value: 0.39 (n-hexane:ether 85:15).

NMR (CDCl$_3$, 300 MHz): 0.9 [3] tr, J=8 Hz, 1.2–1.7 [18] m, 1.9 [2] q, J=8 Hz, 2.25 [2] tr, J=8 Hz, 2.35–2.8 [5] m, 4.1 [2] q, J=8 Hz, 4.35 [2] q, J=8 Hz, 5.0–5.15 [2] m, 5.25–5.35 [2] m, 7.2 [2] d, J=8 Hz, 7.9 [2] d, J=8 Hz.

EXAMPLE 110

6-(4-Carboxybenzyl)-7(Z), 10(Z)-hexadecadienoic acid

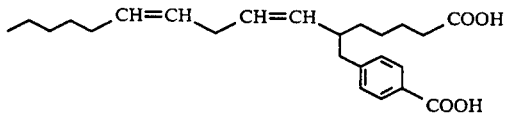

0.3 g of the compound obtained in Example 104 are saponified following the same procedure as in Example 68. 0.2 g of a solid product are thus obtained.

Yield: 76% of theory.

R$_f$-value: 0.41 (methylene chloride:methanol 95:5).

NMR (CDCl$_3$, 250 MHz): 0.9 [3] tr, J=8 Hz, 1.2–1.7 [12] m, 1.9 [2] q, J=8 Hz, 2.3–2.8 [7] m, 5.0–5.15 [2] m, 5.25–5.4 [2] m, 7.25 [2] d, J=8 Hz, 8.0 [2] d, J=8 Hz.

EXAMPLES 111 AND 112

6-(4-Methoxycarbonylbenzyl)-8-[3-(5-phenoxypentyl)-phenyl]-7(Z)-octenoic acid methyl ester (cis-isomer)

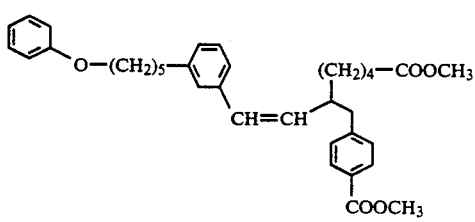

and 6-(4-methoxycarbonylbenzyl)-8-[3-(5-phenoxypentyl)-phenyl]-7(E)-octenoic acid methyl ester (trans-isomer)

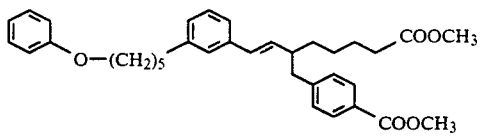

299.6 mg (0.5 mmol) of 3-(5-phenoxypent-1-yl) benzyltriphenylphosphonium bromide are reacted with 0.17 g (0.555 mmol) of 6-formyl-7-(4-methoxycarbonylphenyl)heptanoic acid methyl ester and chromatographed following the same procedure as in Examples 87 and 88. 32 mg of the cis-isomer and 134 mg of the trans-isomer are thus obtained.

Yield: 13% of theory of the cis-isomer, 53% of theory of the trans-isomer.

R$_f$-value: 0.35 for the cis-isomer (n-hexane:ethylacetate 8:2), 0.30 for the trans-isomer (n-hexane:ethylacetate 8:2).

NMR (CDCl$_3$, 300 MHz) of the cis-isomer: 1.15–1.7 [10] m, 1.7 [2] quintet, J=8 Hz, 2.2 [2] tr, J=8 Hz, 2.55 [2] tr, J=8 Hz, 2.6–2.8 [2] m, 2.8–2.95 [1] m, 3.65 [3] s, 3.9 [3] s, 3.95 [2] tr, J=8 Hz, 5.35 [1] tr, J=10 Hz, 6.4 [1] d, J=10 Hz, 6.65 [1] s, 6.8 [1] d, J=8 Hz, 6.85–7.0 [4] m, 7.1–7.2 [3] m, 7.25–7.35 [2] m, 7.9 [2] d, J=8 Hz. of the trans-isomer: 1.2–1.75 [10] m, 1.8 [2] quintet, J=8 Hz, 2.25 [2] tr, J=8 Hz, 2.4–2.55 [1] m, 2.6 [2] tr, J=8 Hz, 2.7–2.85 [2] m, 3.65 [3] s, 3.9 [3] s, 3.95 [2] tr, J=8 Hz, 5.95 [1] dd, J=14 Hz, J=8 Hz, 6.2 [1] d, J=14 Hz, 6.85–6.95 [3] m, 7.0 [1] d, J=8 Hz, 7.05–7.3 [7] m, 7.9 [2] d, J=8 Hz.

EXAMPLE 113

6-(4-Carboxybenzyl)-8-[3-(5-phenoxypentyl)phenyl]-7[E]-octenoic acid

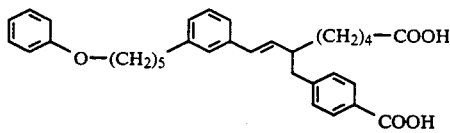

8.25 mg of the compound obtained in Example 111 (trans-isomer) are saponified following the same procedure as in Example 68. 74 mg of the product are thus obtained.

Yield: 92% of theory

R$_f$-value: 0.65(mobile solvent:organic phase of a vigorously shaken mixture of 44 ml of ethylacetate, 8 ml of glacial acetic acid, 20 ml of isooctane and 40 ml of water).

NMR (CDCl$_3$, 300 MHz): 1.2–1.7 [10] m, 1.8 [2] quintet, J=8 Hz, 2.3 [2] tr, J =8 Hz, 2.4–2.55 [1] m, 2.6 [2] tr, J=8 Hz, 2.7–2.85 [2] m, 3.95 [2] tr, J=8 Hz, 5.95 [1] dd, J=14 Hz, J=8 Hz, 6.2 [1] d, J=14 Hz, 6.8–6.95 [3] m, 7.0 [1] d, J=8 Hz, 7,1–7.3 [7] m, 8.0 [2] d, J=8 Hz.

EXAMPLE 114

6-(4-Carboxybenzyl)-8-[3-(5-phenoxypentyl)phenyl]-7(Z)-octenoic acid

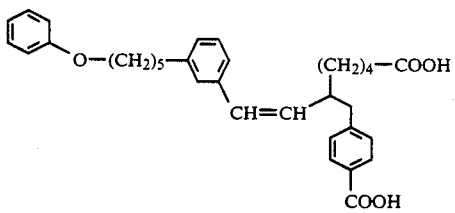

20 mg of the compound obtained in Example 112 (cis-isomer) are saponified following the same procedure as in Example 68. 16.5 mg of the product are thus obtained.

Yield: 87% of theory.

$R_f$-value: 0.67 (mobile solvent:organic phase of a vigorously shaken mixture of 44 ml of ethylacetate, 8 ml of glacial acetic acid, 20 ml of isooctane and 40 ml of water).

EXAMPLE 115

6-(4-Methoxycarbonylbenzyl)-8-[4-(5-phenoxypentyl)-phenyl]-7(E)-octenoic acid methyl ester

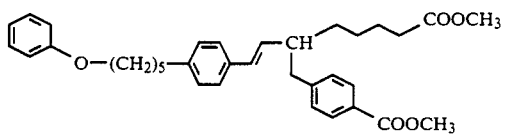

146.4 mg (0.25 mmol) of 4-(5-phenoxypent-1-yl)benzyltriphenylphosphonium bromide are reacted with 77.2 mg (0.25 mmol) of 6-formyl-7-(4-methoxycarbonylphenyl)heptanoic acid methyl ester and chromatographed following the same procedure as in Example 87 and 88. 27 mg of the trans-isomer are thus obtained as the product in addition to a very small amount of the cisisomer, which was discarded.

Yield: 21% of theory.

$R_f$-value: 0.13 (n-hexane:ethyl acetate 88:12).

NMR (CDCl$_3$, 300 MHz): 1.2–1.7 [10] m, 1.8 [2] quintet, J=8 Hz, 2.25 [2] tr, J=8 Hz, 2.35–2.5 [1] m, 2.6 [2] tr, J=8 Hz, 2.65–2.8 [2] m, 3.65 [3] s, 3.9 [3] s, 3.95 [2] tr, J=8 Hz, 5.9 [1] dd, J=14 Hz, J=8 Hz, 6.2 [1] d, J=14 Hz, 6.85–6.95 [3] m, 7.1 [2] d, J=8 Hz, 7.2–7.35 [6] m, 7.95 [2] d, J=8 Hz.

EXAMPLE 116

6-(4-Carboxybenzyl)-8-[4-(5-phenoxypentyl)phenyl]-7(E)-octenoic acid

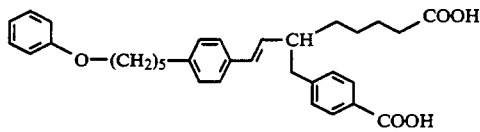

15.3 mg of the compound obtained in Example 115 are saponified following the same procedure as in Example 68. 15.4 mg of the product are thus obtained.

Yield: 100% of theory.

$R_f$-value: 0.67 (mobile solvent: organic phase of a vigorously shaken mixture of 44 ml of ethyl acetate, 8 ml of glacial acetic acid, 20 ml of isooctane and 40 ml of water).

EXAMPLE 117

6-(4-Carboxybenzyl)-5-thia-7(E), 9(E), 11(z), 14(z)-eicosatetraenoic acid 5,5-dioxide A solution of 0.37 (0.6 mmol) of oxone (2KHSO$_5$.KHSO$_4$.K$_2$SO$_4$) in 3.7 ml of water was added to a solution of 30 mg (0.06 mmol) of 6-(4-carboxybenzyl)-5-thia-7(E), 9(E), 11(z), 14(z)-eicosatetraenoic acid in 120 ml of methanol-water (1:1) as it was stirred at 0° C. The resultant solution was stirred overnight at 0° and then evaporated in vacuo to remove the methanol. The resultant aqueous residue was extracted twice with methylenechloride. The combined extracts were dried over sodium sulfate and then evaporated in vacuo. The residue was purified by preparative HPLC on a Lichrosorb RP-8 (7 μm) column using elution with acetonitrile/water/acetic acid (40:60:0.1) which had been adjusted to pH 5.6 with concentrated aqueous ammonia. The product eluent was evaporated in vacuo to remove most acetonitrile, then acidified with 1N HCl and finally extracted with toluene. The product was dried over sodiumsulfate and evaporated in vacuo to yield 3 mg of purified product.

Yield: 9.2% of theory

HPLC: 2 minutes retention time: Lichrosorb RP 18 (7 μm), 25 cm×4 mm, solvent as given above, 4.5 ml/min., detection at 280 nm.

EXAMPLE 118

1-bromo-4-phenylbutane

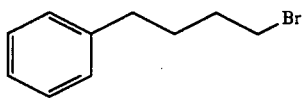

15.0 g (0.1 mol) 4-phenylbutanol and 39.8 g (0.12 mol) carbontetrabromide were dissolved in 500 ml dry dichloromethane and cooled to 0° C., 36.7 g (0.14 mol) triphenylphosphine was then added and the mixture stirred 1.5 hours under argon at 0° C. then evaporated in vacuo. The resulting mixture was stirred in ether-hexane (1:1) and filtered to remove insoluble material. The filtrate was then passed through a pad of silica gel and concentrated to give a pale yellow liquid 21.3 g.

Yield: 100% of theory.

TLC $R_f$: 0.57 (ether-hexane 1:1).

NMR (CDCl$_3$, 60 MHz): 1.6–1.8[4]m, 2.55[2] t, J=7 Hz 3.3[2], t, J=7 Hz, 7.2[5]s,

EXAMPLE 119

4-phenylbutyltriphenylphosphonium bromide

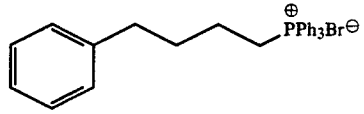

A solution of 10.65 g (50 mmol) 1-bromo-4-phenylbutane and 13.1 g (50 mmol) triphenylphosphine in 100 ml acetonitrile was refluxed for 18 hours under argon, then concentrated in vacuo. The residue was triturated with ether and the resulting solid was collected by filtration and washed with ether 20.7 g.
m.p.: 136°–138° C.
Yield: 87% of theory.
TLC R$_f$: 0.30 (CH$_2$Cl$_2$:MeOH 9:1).
NMR (CDCl$_3$ 60 MHz): 1.6–2.0[4] m, 2.6[2], t, J=7 Hz, 3.6–4.0[2] m, 7.0[5] s, 7.5–7.8[15] m.

EXAMPLE 120

1-(3-bromophenyl)-5-phenylpent-1(E)ene

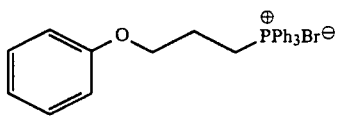

Using the procedure of example 119 and 10.75 g (50 mmol) 3-phenoxypropylbromide and 13.1 g (50 mmol) triphenylphosphine gave a white solid m.p. 179.5°–180.5° C., 22.4 g.
Yield: 93% of theory.
TLC R$_f$: 0.30 (CH$_2$Cl$_2$:MeOH 9:1).
NMR (CDCl$_3$, 60 MHz): 2.1[2] m, 3.7[2] m, 4.02[2] t, J=5 Hz, 6.7–7.2[5] m, 7.7[15] m.

EXAMPLE 121

1-(3-bromophenyl)-5-phenylpent-1(E)ene

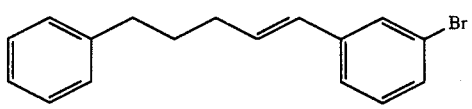

9.6 g (20 mmol) 5-phenylpentyltriphenylphosphonium bromide in 120 ml dry tetrahydrofuran was cooled to −78° C. under argon and 16.4 ml (20 mmol) n-butyllithium in hexane (content titrated) was added and the mixture allowed to warm to −20° C. until a clear (orange) solution resulted. This was cooled to −78° C. and 2.4 ml (20 mmol) 3-bromobenzaldehyde was added. This was allowed to reach room temperature then diluted with water and extracted twice with ether. The combined organic phases were washed with saturated sodium chloride solution and concentrated in vacuo. The residue was triturated with ether-hexane (1:1) and filtered to remove insoluble material. The filtrate was then filtered through a pad of silica gel and concentrated in vacuo to give a yellow liquid 4.6 g.
Yield: 76% of theory.
TLC R$_f$: 0.53 (ether-hexane 1:1).
NMR (CDCl$_3$, 60 MHz): 1.65[2] t, J=7 Hz, 2.20[2] t, J=7 Hz, 2.52[2] t, J=7 Hz, 5.56[1] dt, J=12 Hz, J=7 Hz, 6.17[1] dt, J=12 Hz, J=1.5 Jz, 6.9–7.4[9] m.

EXAMPLE 122

1-(3-bromophenyl)-4-phenoxybut-1(E)ene

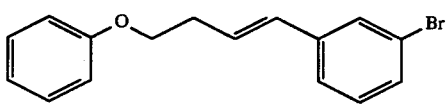

Following the procedure of example 121 using the product of Example 120 gave a pale yellow liquid 4.8 g.
Yield: 80% of theory.
TLC R$_f$: 0.50 (ether-hexane 1:1).
NMR (CDCl$_3$, 60 MHz): 2.7[2] dd, J=6 Hz, J 1.5 Hz, 3.95[2] t, J=6 Hz, 5.77[1] dt, J=12 Hz, J=6 Hz, 6.46[1] dt, J=12 Hz, J=1.5 Hz, 6.9–7.5[9] m.

EXAMPLE 123

2-(3-[5-phenylpent-1(E)enyl]phenyl)ethanol

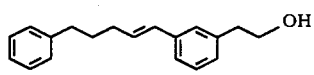

2.8 g (8.3 mmol) 1-(3-bromophenyl)-5-phenylpentene was dissolved in 30 ml dry tetrahydrofuran and cooled to −78° C. under argon. 5 ml (8.3 mmol) t-butyllithium solution in pentane was added. After 15 minutes 2 ml ethyleneoxide was added and the solution was allowed to reach room temperature. It was poured into ammonium chloride solution and extracted twice with ether. The combined extracts were washed with saturated sodium chloride solution then concentrated in vacuo. The residue was chromatographed on 80 g of silica gel (Merck Si60, 0.063–0.200 mm) to give a fraction which on concentration in vacuo gave a colourless liquid 1.4 g.
Yield: 53% of theory,
TLC R$_f$: 0.18 (ether-hexane 1:1).
NMR (CDCl$_3$, 60 MHz): 1.4–1.8[6] m, 2.1[1] s, 2.60[2] t, J=7 Hz, 2.80[2] t, J=7 Hz, 3.80[2] t, J=7 Hz, 5.6–6.0[1] m, 6.3[1] d, J=4 Hz, 6.7–7.3[9] m.

EXAMPLE 124

2-(3-[4-phenoxybut-1(E)enyl]phenyl)ethanol

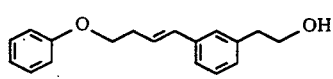

Following the procedure of example 123 but using 1.22 g (4 mmol) 1-(3-bromophenyl)-4-phenoxybutene gave an oily product after chromatography 0.44 g.
Yield: 40% of theory.
TLC R$_f$: 0.12 (ether-hexane 1:1).
NMR (CDCl$_3$, 60 MHz): 1.6–1.8[2] m, 2.75[2] t, J=7 Hz, 3.75[2] t, J=7 Hz, 3.99[2] dt, J=7 Hz, 1.5 Hz, 5.6–6.0[1] m, 6.3[1] d, J=4 Hz, 6.7–7.3[9] m.

EXAMPLE 125

2-(3-[5-phenylpentyl]phenyl)ethanol

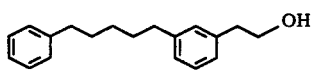

1.4 g (2-3-[5-phenylpentenyl]phenyl)ethanol in 100 ml ethyl acetate was treated with 200 mg 10% palladium on charcoal and hydrogen at 1 bar for 1 hour. The mixture was filtered through celite and concentrated in vacuo to give a colorless oil 1.42 g.
Yield: 99% of theory.
TLC R$_f$: 0.18 (ether-hexane 1:1).
NMR (CDCl$_3$, 60 MHz): 1.4–1.8[6] m, 2.1[1] s, 2.6[4] t, J=7 Hz, 2.80[2] t, J=7 Hz, 3.8[2] t, J=7 Hz, 7.1[4] s, 7.2[5] s.

EXAMPLE 126

2-(3-[4-phenoxybutyl]phenyl)ethanol

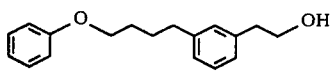

0.44 g 2-(3-[4-phenoxybutenyl]phenylethanol was hydrogenated following the procedure of Example 125 to give a colorless oil 0.44 g.
Yield: 99% of theory.
TLC $R_f$: 0.12 (ether-hexane 1:1).
NMR (CDCl$_3$, 60 MHz): 1.6–1.9[4] m, 2.1[1] s, 2.5–2.8[2] m, 2.73[2] t, J=7 Hz, 3.72[2] t, J=7 Hz, 3.8–4.0[2] m, 6.8–7.4[9] m.

EXAMPLE 127

1-(3-[2-bromoethyl]phenyl)-5-phenylpentane

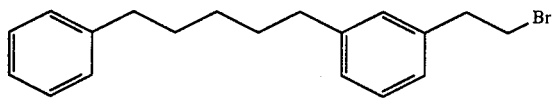

Following the procedure of Example 118 1.4 g (5.3 mmol) of 2.(3-[5-phenylpentyl]phenyl)ethanol gave an oily product 1.62 g.
Yield: 96% of theory.
TLC $R_f$: 0.62 (ether-hexane 1:1).
NMR (CDCl$_3$, 60 MHz): 1.4–1.7[6] m, 2.53[4] t, J=7 Hz, 3.2–3.3[4] m, 6.85–6.96[4] m, 7.06[5] s.

EXAMPLE 128

1-(3-[2-bromoethyl]phenyl)-4-phenoxybutane

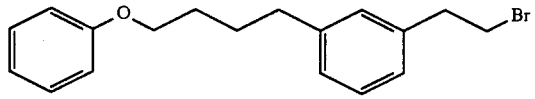

Following the procedure for Example 118 0.44 g (1.6 mmol) 2-(3-[4-phenoxybutyl]phenyl)ethanol gave an oily product 0.38 g.
Yield 70% of theory.
TLC RF 0.55 (ether-hexane 1:1).
NMR (CDCl$_3$, 60 MHz): 1.6–1.8[4] m, 2.5–2.8[2] m, 2.9–3.6 [4] m, 3.8–4.0[2] m, 6.7–7.4[9] m.

EXAMPLE 129

2-(3-[5-phenylpentyl]phenyl)ethyltriphenylphosphonium bromide

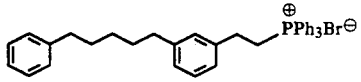

0.99 g (3 mmol) 1-(3-[2-bromoethyl]phenyl)-5-phenylpentane was heated with 0.78 g (3 mmol) triphenylphosphine at 90° C. for 2 days in the absence of solvent. The glassy solid was dissolved in dichloromethane and chromatographed on 50 g silica gel eluting initially with dichloromethane than with 10% methanol in dichloromethane. Removal of solvent in vacuo gave a glassy solid 1.62 g.
Yield: 91% of theory.
TLC $R_f$: 0.20 (dichloromethane:methanol 10:1).
NMR (CDCl$_3$, 60 MHz): 1.2–1.7[6] m, 2.2–2.6[4] m, 2.7–3.1[2] m, 3.7–4.0[2] m, 6.4–6.7[4] m, 6.5–6.8[5] m, 7.2–7.6[15] m.

EXAMPLE 130

2-(3-[4-phenoxybutyl]-phenyl)ethyl triphenylphosphonium bromide

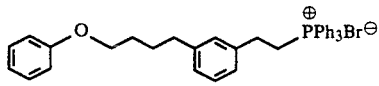

0.37 g (1.1 mmol) 1-(3-[2-bromoethyl]phenyl)-4-phenoxybutane and 0.29 g (1.1 mmol) triphenylphosphine were refluxed for 6 days in 10 ml ethanol. The solution was concentrated in and chromatographed on 40 g silica gel with dichloromethane and then 10% methanol-dichloromethane. The fractions were concentrated in vacuo to give a colorless glass 0.50 g.
Yield: 76% of theory.
TLC $R_f$: 0.22 (dichloromethane:methanol 9:1).
NMR (CDCl$_3$, 60 MHz): 1.7–1.9[4] m, 2.5–2.9[4] m, 2.7–3.1[2] m, 3.7–4.0[4] m, 6.8–7.4[9] m, 7.5–8.0[15] m,

EXAMPLE 131

Ethyl 6-(4-carbethoxybenzyl)-9-(3-[5-phenylpentyl]phenyl)-non-7(Z)enoate

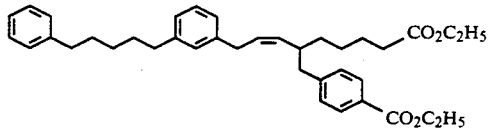

Following the procedure of Example 121 0.81 g (1.4 mmol) 2-(3-[5-phenylpentyl]phenyl)ethyltriphenylphosphonium bromide and 0.42 g (1.4 mmol) ethyl 7-(4-carbethoxyphenyl)-6-formylheptenoate gave an oily product which was chromatographed on 40 g silica gel (Woelm 0.040–0.063 mm) with ether:hexane (3.17) to give a fraction which on concentration in vacuo gave a colourless oil 213 mg.
Yield: 28% of theory.
TLC $R_f$: 0.28 (ether:hexane 1:4).
NMR (CDCl$_3$, 60 MHz): 1.33[6] t, J=7 Hz, 1.5–1.8[13] m, 2.17[2] t, J=7 Hz, 2.3–2.7[6] m, 2.96[2] d, J=6 Hz, 3.95[2] q, J=7 Hz, 4.23[2] q, J=7 Hz, 5.05[1] d, J=10 Hz, 5.35[1] dt, J=10 Hz, J=6 Hz, 6.6[2] m, 6.8[2] m, 6.95–7.05[7] m, 7.74[2] d, J=7 Hz.

EXAMPLE 132

6-(4-carboxybenzyl)-9-(3-[5-phenylpentyl]phenyl)-7(Z)nonenoic acid

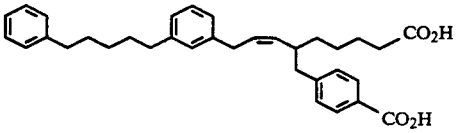

The product of example 131 was saponified by dissolving in 2 ml THF and refluxing for 24 hours with 2 ml 1M dosium hydroxide solution. The solution was acidified with 1M hydrochlorid acid and extracted twice with ethyl acetate. The combined organic phases were washed with saturated sodium chloride solution, dried with magnesium sulphate then concentrated in vacuo to give a waxy whit solid 180 mg.

Recrystallization from ether-hexane gave a powder m.p. 123°-124° C.

Yield: 94% of theory.

HPLC Lichrosorb RP-18 (7 μM) column MeCN:-H2O AcOH 90:10; 0.1 pH 5.6 at 1 ml/minute $t_R$ 5.7 min.

NMR (CDCl3, 60 MHz): 1.4-1.8[13] m, 2.1-2.7[9] m, 3.05[2] d, J=6 Hz, 5.0-5.6[2] m, 6.7[2] s, 6.9[2] s, 7.0-7.3[7] m, 7.92[2] d, J=8 Hz.

EXAMPLE 133

Ethyl 6-(4-carbethoxybenzyl)-9-(3-[4-phenoxybutyl]phenyl)-non-7(Z)enoate

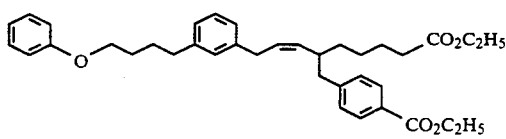

Following the procedure of Example 121 0.43 g (0.7 mmol) 2-(3-[4-phenoxybutoxy]phenyl)ethyl triphenylphosphonium bromide and 0.23 g (0.7 mmol) ethyl 7-(4-carbethoxyphenyl)-6-formyl heptanoate gave an oily product which was chromatographed on 25 g silica gel (Woelm 0.040-0.063 mm) with ether-hexane 1:4 to give a fraction which on concentration in vacuo gave an oil 154 mg.

Yield: 38% of theory.

TLC $R_f$: 0.28 (ether:hexane 1:4).

NMR (CDCl3, 60 MHz): 1.20[3] t, J=7 Hz, 1.35[3] t, J=7 Hz, 1.3-1.6[4] m, 1.6-1.9[6] m, 2.20[2] t, J=7 Hz, 2.5-2.7[5] m, 3.0[2] d, J=6 Hz, 3.85[2] m, 4.05[2] q, J=7 Hz, 4.25[2] q, J=7 Hz, 5.05[1] m, 5.35[1] dt, J=9 Hz, J=4 Hz, 6.82[2] d, J=8 Hz, 6.6-7.0[5] m, 7.06 d, J=8 Hz, 7.0-7.3[2] m, 7.87[2] d, J=8 Hz.

EXAMPLE 134

6-(4-carboxybenzyl)-9-(3-[4-phenoxybutyl]phenyl)non-7(Z)enoic acid

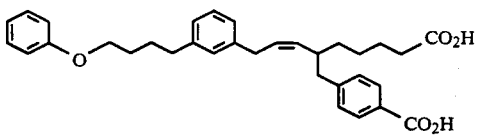

The product of example 133 was saponified by dissolving in 3 ml tetrahydrofuran and refluxing for 18 hours with 3 ml aqueous lithium hydroxide solution (10 mg/ml). The solution was then acidified with 1M hydrochlorid acid and extracted twice with ethyl acetate. The combined organic phases were washed with saturated sodium chloride solution, dried with magnesium sulphate then concentrated in vacuo giving a white solid 80 mg m.p. 93°-95° C.

Yield: 58% of theory.

HPLC Lichrosorb RP-18 (7 μM) column. MeCN:-H2O: AcOH 70:30:0.1, pH 5.6 at 1 ml/minute $t_R$ 12.7 minutes.

NMR (CDCl3, 60 MHz): 1.25-1.9[12] m, 2.25[2] t, J=7 Hz, 2.3-2.7[5] m, 3.05[2] d, J=6 Hz, 3.85[2] t, J=6 Hz, 5.05[1] m, 5.35[1] dt, J=9 Hz, J=4 Hz, 6.65[3] s, 6.80[2] d, J=8 Hz, 6.75-7.0[2] m, 7.07[4] d, J=8 Hz, 7.85[2] d, J=8 Hz.

EXAMPLE 135

Methyl 4-hydroxybutanoate

8.61 g (0.1 mol) ν-butyrolactone in 100 ml dry methanol was stirred for 1 hour with 1.0 g (0.02 mol) sodium methoxide, under argon, 1.1 g (0.02 mol) ammonium chloride was added and the solvent removed in vacuo. The resulting liquid was dissolved in dichloromethane and washed with saturated sodium chloride solution. The organic phase was dried with magnesium sulphate and concentrated in vacuo to give a colorless oil 10.3 g.

Yield: 87% of theory.

NMR (CDCl3, 60 MHz): 1.85[2] t, J=7 Hz, 2.40[2] t, J=7 Hz, 3.57[2] t, J=7 Hz, 3.67[3] s, 4.1[1] s.

EXAMPLE 136

Methyl-4-oxobutanoate

To 10.3 g (86 mmol) methyl 4-hydroxybutanoate in 100 ml dry dichloromethane was added 20 g (93 mmol) pyridinium chlorochromate. After 4 hours this was filtered through a pad of florisil and concentrated in vacuo. Kugelrohr distillation gave 3.95 g colourless liquid.

Boiling point: 50° C. 0.5 mbar.

Yield: 39% of theory.

NMR (CDCl3, 60 MHz): 2.4[2] m, 2.6[2] m, 3.65[3] s, 9.72[1] s.

EXAMPLE 137

Methyl 4-trimethylsilyloxy-but-3enoate

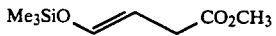

Following the procedure of example 57 1.9 g (17 mmol) methyl 4-oxobutenoate gave an oily residue which was purified by Kugelrohr distillation as a colorless liquid 1.8 g.

Boiling point: 40° C. 0.5 mbar.

Yield: 56% of theory.

NMR (CDCl3, 60 MHz): 0.18[9] s, 2.8-3.2[2] m, 3.63[3] s, 4.64[1] m, 6.35[1] m.

EXAMPLE 138

Methyl 3-(4-carbomethoxyphenylthio)-4-oxobutanoate

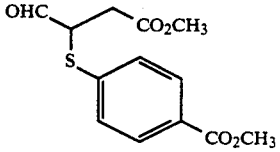

A solution of 2.0 g (10 mmol) 4-methoxycarbonylphenylsulphenic acid chloride in 25 ml carbon tetrachloride was slowly added to a solution of 0.94 g (5 mmol) methyl 4-trimethylsilyloxybutene in 20 ml dichloromethane at −20° C. After 1 hour 2 ml methanol was added and the solvent removed at reduced pressure to give a semi-solid. This was triturated with ether filtered and concentrated in vacuo to give an oily residue which was chromatographed on 50 g silica gel with ethylacetate-hexane 1:4 to give a pale yellow oil 0.30 g.

Yield: 21% of theory.

NMR (CDCl3, 60MHz): 2.83[2] m, 3.71[3] s, 3.75[1] m, 3.90[3] s, 7.48[2] d, J=9 Hz, 7.94[2] d, J=9 Hz, 9.62[1] d, J=1.5 Hz.

EXAMPLE 139

3-(4-Fluorophenoxy)propyl bromide

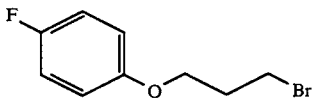

A mixture of 11.2 g (0.1 mol) of 4-fluorophenol, 16.5 g (0.12 mol) of pulverized potassium carbonate, 20.2 g (0.1 mol) of 1,3-dibromopropane and 100 ml of anhydrous dimethoxyethane was refluxed under nitrogen for 6 hours and then cooled. The mixture was diluted with methylene chloride and washed with water. The resultant organic product solution was dried over Na2SO4 and evaporated in vacuo. The residue was chromatographed on silica gel using cyclohexane elution to give pure product.

Yield: 29% of theory.

NMR (CDCl3, 60 MHz): 2.29[2] q, J=8 Hz, 3.59[2] t, J=8 Hz, 4.06[2] t, J=8 Hz, 6.8-7.0[4] m.

EXAMPLE 140

2-{3-[3-(4-Fluorophenoxy)propoxy]phenyl}ethanol

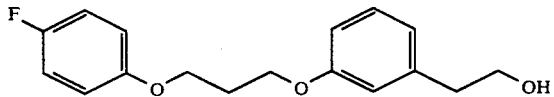

By following the procedure of example 9 and using 3-(4-fluorophenoxy)propyl bromide rather than 4-phenoxybutyl bromide and 2-(3-hydroxyphenyl)ethanol rather than 2-(4-hydroxyphenyl)ethanol, the title compound was prepared.

Yield: 95% of theory.

NMR (CDCl3, 250 MHz): 1.44[1] d, J=8 Hz, OH, 2.24[2]q, J=8 Hz, 2.83[2] t, J=8 Hz, 3.85[2] q, J=8 Hz, 4.11[2] t, J=8 Hz, 4.15[2] t, J=8 Hz, 6.75-7.25[8] m.

EXAMPLE 141

2-{3-[3-(4-Fluorophenoxy)propoxy]phenyl}-ethyl bromide

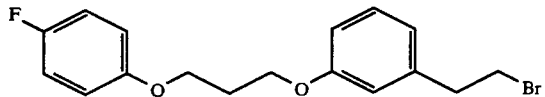

By following the procedure of example 8 and using the product of Example 140 as starting material the title bromide was prepared.

Yield: 74% of theory.

NMR (CDCl3, 300 MHz): 2.25[2] q, J=8 Hz, 3.13[2] t, J=8 Hz, 3.55[2] t, J=8 Hz, 4.12[2] t, J=8 Hz, 4.16[2] t, J=8 Hz, 6.75-7.26[8] m.

EXAMPLE 142

2-{3-[3-(4-Fluorophenoxy)propoxy]phenyl}-ethyl triphenylphosphonium bromide

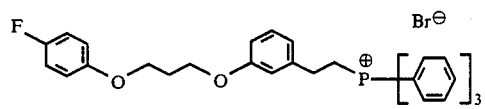

A solution of 20 mmol of bromide (example 141) and 30 mmol of triphenyl phosphine in 60 ml of ethanol was refluxed 20 hours under nitrogen and then cooled and evaporated in vacuo. The residue was chromatographed on silica gel using first CHCl3 to elute starting material residues and then 5% CH3OH in CHCl3 to elute the product. Evaporation of pure fractions yielded the title compound as a viscous oil.

Yield: 50% of theory

NMR (CDCl3, 300 MHz): 2.15-2.27[2] m, 2.95-3.1[2] m, 4.04-4.24[6] m, 6.7-7.15[8] m, 7.65-7.0[15] m.

EXAMPLE 143

6-(4-Methoxycarbonylbenzyl)-9-{3-[3-(4-fluorophenoxy)propoxy]benzyl}-7(Z)-nonenoic acid methyl ester

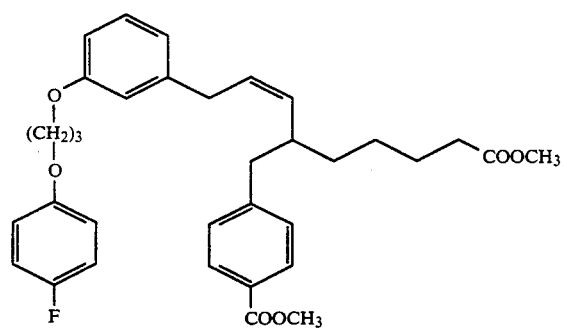

1.24 g (2 mmol) of the product of example 142 was dissolved in 25 ml of anhydrous tetrahydrofuran under argon and then 140 mg (4 mmol) of sodium hydride (80% in mineral oil) was added. The resultant mixture was refluxed under argon for 30 minutes and then cooled to 0° C. Then a solution of 450 mg (1.5 mmol) of 6-formyl-7-(4-methoxycarbonylphenyl)heptanoic acid methyl ester in 1.5 ml anhydrous tetrahydrofuran was added quickly dropwise. The resultant mixture was stirred 15 min. at 0° C. and then 15 minutes at room temperature and then 1 hour at reflux. The product was isolated as in example 67 to give 0.35 g of pure product.

Yield: 41% of theory.

NMR (CDCl3, 300 MHz): 1.2-1.7[6] m, 2.2-2.3[4] m, 2.5-2.6[1] m, 2.65-2.8[2] m, 3.0[1] dd, J=14.8 Hz, 3.13[1] dd, J=14.8 Hz, 3.65[3] s, 3.9[3] s, 4.07-4.17[4] m, 5.21[1] t, J=10 Hz, 5.51[1] dt, J=10.7 Hz, 6.45-7.23[10] m, 7.93[2] d, J=8 Hz,

EXAMPLE 144

6-(4-Carboxybenzyl)-9-{3-[3-(4-fluorophenoxy)-propoxy]benzyl}-7-(Z)-nonenoic acid

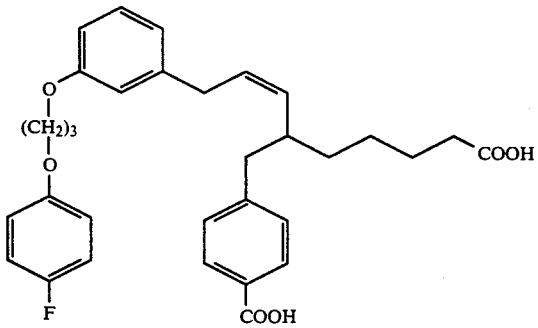

Using the ester product of Example 143 and the procedure of example 68 the title compound was prepared. Yield: 85% of theory.

NMR (CDCl$_3$, 300 MHz): 1.2–1.7[6] m, 2.23[2] q, J=8 Hz, 2.33[2] t, J=8 Hz, 2.5–2.8[3] m, 3.03[1] dd, J=14.8 Hz, 3.14[1] dd, J=14.8 Hz, 4.04–4.15[4] m, 5.22[1] t, J=10 Hz, 5.54[1] dt, J=10.7 Hz, 6.5–7.3[10] m, 7.97[2] d, J=8 Hz.

EXAMPLE 145

Animals-Male Dunkin Hartley 350–400 g (Interfauna).

1. Preparation

A guinea-pig was killed by a blow to the head and the trachea placed in Tyrodes solution plus indomethacin (3×10$^{-6}$M). The trachea was cut open longitudinally opposite the trachealis muscle and alternating transverse cuts made across three quarters of the tissue width. The preparation was opened out as a zig-zag-chain and suspended in a 10 ml tissue-bath containing Tyrodes solution with indomethacin (3×10$^{-6}$M) at 37° C. gassed with 5% CO$_2$ in oxygen. Tissue movement was monitored with a Hugo Sachs isotonic transducer with a load of 250–500 mg.

2. Experimental Procedure

Upon equilibration maximal response was determined using 10$^{-4}$ and 3×10$^{-4}$M histamine. The histamine was washed out and Tyrodes exchanged for Tyrodes plus indomethacin, L-serine borate (45 mM) and L-cysteine (10 mM). When the tissues had re-equilibrated one of each set of four preparations was treated with a series of 10 μl volumes of the vehicle control EtOH. The other three were each treated with cumulative additions of the test drug to give a tissue-bath concentration from 10$^{-11}$–10$^{-5}$M. Fifteen minutes after the final addition of test drug of EtOH a cumulative concentration response curve for LTD$_4$ (10$^{-10}$–10$^{-6}$M) was applied. When maximal LTD$_4$-concentration was reached the tissues were discarded.

3. Materials

Indomethacin, LTD$_4$ (Leukotrien D$_4$), boric acid, L-cysteine and L-serine.

Tyrodes solution consisted of the following ANALAR grade substances (mM) dissolved in distilled water: NaCl 137, MgCl$_2$ 2.1, KCl 2.7, NaH$_2$DO$_4$ 0.5, CaCl$_2$ 2.4, NaHCO$_3$ 11.9, D-glucose 9.2.

RESULTS

Contractions were normalised to the histamine-induced maximum for each preparation. The responses to analogue, LTD$_4$ and LTD$_4$ plus analogue were then expressed as a percentage of the maximum LTD$_4$ response in the appropriate control preparation. EC$_{50}$ (that concentration required to induce a 50% maximal LTD$_4$ response) values for 'test' and control tissues were calculated using a least squares linear regression program. These values were used to calculate a pK$_B$ to quantify the degree of antagonism where appropriate.

It will be appreciated that the instant specification and claims are set forth by way of illustration and not limitation, and that various modifications and changes may be made without departing from the spirit and scope of the present invention.

What is claimed is:

1. A compound having the formula:

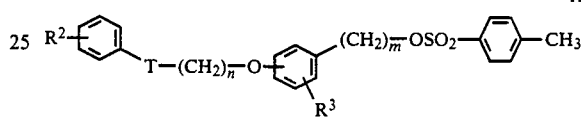

XIV in which

R$^2$ represents hydrogen, alkyl, alkoxy, halogen, trifluoromethyl, trifluoromethoxy, cyano or nitro;

T represent oxygen or a direct bond;

n represents a number 1 to 10;

R$^3$ represents hydrogen, alkyl, alkoxy, halogen, trifluoromethyl, trifluoromethoxy, cyano or nitro; and m represents a number 0 to 7.

2. The compound according to claim 1, having the formula:

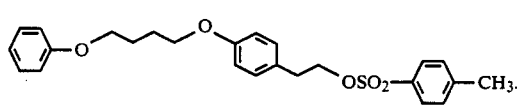

3. A leucotriene disease antagonist composition comprising a leucotriene disease antagonistic effective amount of an alkenoic acid derivative according to claim 1 in admixture with a pharmaceutically acceptable carrier.

4. A composition according to claim 3 comprising 0.5 to 98 weight % of the alkenoic acid.

5. A unit dose of a composition according to claim 3 in the form of a tablet or a capsule.

6. A method of treating a patient suffering from a leucotriene disease comprising administering to said patient a leucotriene disease antagonistic effective amount of an alkenoic acid derivative according to claim 1.

7. A method according to claim 6 wherein the leucotriene disease is a circulatory disease.

8. A method according to claim 6, wherein the leucotriene disease is a respiratory disease.

* * * * *